United States Patent [19]

Hagiwara et al.

[11] Patent Number: 4,812,161

[45] Date of Patent: Mar. 14, 1989

[54] THIA (OXA) DIAZOLE DERIVATIVES

[75] Inventors: Kenji Hagiwara; Hisao Ishikawa, both of Odawara; Hideo Hosaka, Kanagawa; Hideo Inaba, Shizuoka, all of Japan

[73] Assignee: Nippon Soda Co., Ltd., Tokyo, Japan

[21] Appl. No.: 760,158

[22] Filed: Jul. 29, 1985

[30] Foreign Application Priority Data

Aug. 8, 1984 [JP] Japan ................... 59-164855
Jan. 10, 1985 [JP] Japan ..................... 60-1446

[51] Int. Cl.$^4$ ................... A01N 43/82; C07D 285/14; C07D 251/24; C07D 401/04
[52] U.S. Cl. ............................. 71/90; 71/86; 71/87; 544/69; 544/70; 544/113; 544/124; 544/134; 544/216; 544/214; 544/353; 544/356; 546/256; 546/271; 548/126; 548/113; 548/110
[58] Field of Search ............... 71/90, 86, 87; 544/124, 544/69, 70, 134, 216; 548/126

[56] References Cited

PUBLICATIONS

Hagiwara et al, Chemical Abstract, vol. 105, entry 60608(a) (1986).

*Primary Examiner*—John M. Ford
*Attorney, Agent, or Firm*—George B. Oujevolk

[57] ABSTRACT

Thia-diazole derivatives having the following partial structural formula had selective herbicidal activity on some crops. A process for producing these compounds is also disclosed:

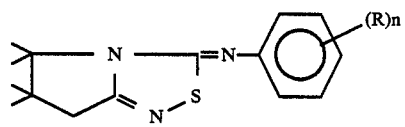

3 Claims, No Drawings

THIA (OXA) DIAZOLE DERIVATIVES

The present invention relates to thia (oxa) diazole derivatives, herbicidal compositions in the form of mixture of such compound(s) with inert carrier(s), and processes for the production of such compounds.

In many cases of agricultural or horticultural cultivation, many kinds and amount of herbicides have come to be used for weed control in order to save the labor of removing weeds in the fields, however, in some occasion, phytotoxicity of herbicides may injure crops, or herbicides remaining in the field may cause environmental pollution.

Consequently, chemicals possessing greater efficacy and higher safty to mammal have been awaited to be developed.

3H-thiazolo-(2,3-c)-1,2,4-thiadiazole having the following formula:

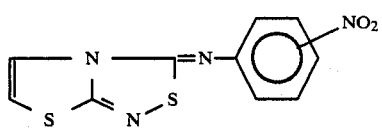

which are similar to but different from the compounds of the present invention at the point that it has double bond on thiazole ring have been reported on J. Org. Chem. 1975 40 (18) 2600–2604.

Also, compounds having the following formula and a process for the preparation thereof:

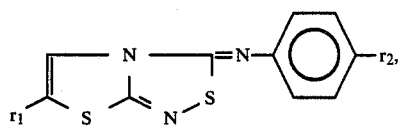

wherein $r_1$ is H, CH$_3$S— or CH$_3$SO—, and $r_2$ is H, or Cl, are described together with their medical fungicidal activity in J. Pharm. Sci. 1979, 68 (2) 182–185.

The Inventors of this invention, studied many thiadiazole derivatives in order to find a compound having herbicidal activity. As a result, they found that a group of compounds having the following partial structure formula:

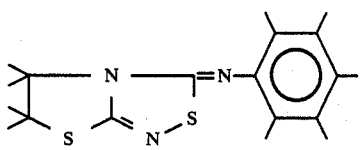

had herbicidal activity and exhibited selectivity on some crops, though said known compounds having doble bond(s) on the thiazole ring contained in the thiazolo (2,3-C) 1,2,4-thiadiazole ring do not have herbicidal activity.

The inventors, further, carried out investigation about the relation between the structure of the condensed ring of the compounds having the following partial structure formula:

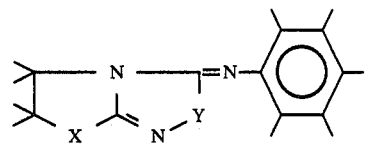

and the herbicidal activity thereof.

As the results, they found that almost all of the compounds having the condensed ring in the formula (II) wherein X represents

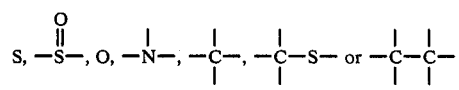

and Y represents S, or O exhibited the excellent herbicidal activity.

On said condensed ring, substituent(s) of hydroxy, $C_{1-8}$ hydrocarbon which may be substituted by halogen, $C_{1-8}$ hydrocarbon-oxy or $C_{1-8}$ hydrocarbon-thio, $C_{1-8}$ hydrocarbon-carbonyloxy, $C_{1-8}$ hydrocarbon-oxycarbonyl or $C_{1-8}$ alkylidene, wherein hydrocarbon means and includes linear, branched or cyclic alkyl, alkenyl or alkynyl; or aryl aralkyl or alkylaryl, are preferred. For the substituents, it looks like the too bulky ones tend to decrease the herbicidal activity.

The inventors conducted further extensive investigation on the relation between the substituent(s) on the phenyl radical (right part of the formula (II) and herbicidal activity and selectivity thereof.

In order to easily explain in detail of said substituents, said substituted phenyl radical is shown as

As the results of the investigation, they found that a substituted phenyl radical of the formula

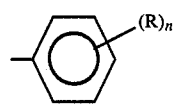

which is explained in detail in the followings, exhibited herbicidal activity and selectivity by joining with the residue of the condensed ring of formula (III) as below:

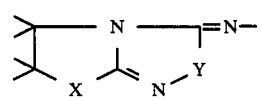

wherein

R represents same or different substituent(s) selected from the group consisting of halogen, nitro, cyano, —G—R$^1$, $$-\underset{\underset{O}{\|}}{C}-K-R^2, \quad -\underset{\underset{O}{\|}}{C}N\underset{R^4}{\overset{R^3}{\diagup}}, \quad -\underset{\underset{O}{\|}}{C}R^5, \quad -C=NOR^6,$$

di-$C_{1-8}$ hydrocarbon-sulfamoyl and —L; and n represents an integer of 1 to 5; and wherein G represents $$-O-, \quad -S-, \quad -\underset{\underset{}{|}}{\overset{r^{10}}{N}}-,$$

in which $r^{10}$ represents hydrogen or $C_{1-8}$ hydrocarbon radical; and $R^1$ represents hydrogen, $$COr^{11}, \quad -\underset{\underset{Or^{13}}{\diagdown}}{\overset{S \diagup Or^{12}}{P}}, \quad -SO_2r^{14}, \quad -\underset{\underset{O}{\|}}{C}r^{15}, \quad -\underset{\underset{O}{\|}}{C}N\underset{r^{17}}{\overset{r^{16}}{\diagup}},$$

heterocyclic radical containing oxygen or nitrogen or —T; and

K represents oxygen or sulfur; and $R^2$ represents hydrogen, metal corresponding to one valency, $C_{1-8}$ alkylidene amino or —U; and each of $R^3$ and $R^4$ represents hydrogen, $C_{1-8}$ hydrocarbon radical, or $C_{1-8}$ hydrocarbon-oxy; and $R^5$ represents $C_{1-8}$ hydrocarbon radical which may be substituted by hydrocabon-oxy; and $R^6$ represents hydrogen, or $C_{1-8}$ hydrocarbon radical, which may be substituted by $C_{1-8}$ hydrocarbon-oxycarbonyl; and $R^7$ represents hydrogen or $C_{1-8}$ hydrocarbon radical; and —L represents $C_{1-8}$ hydrocarbon radical which may be substituted by halogen, hydroxy, cyano, $$-\underset{\underset{O}{\|}}{C}Or^{18},$$

$C_{1-8}$ hydrocarbon-oxy, $C_{1-8}$ hydrocarbon-carbonyloxy or $$-\underset{\underset{Or^{20}}{\diagdown}}{\overset{O \diagup Or^{19}}{P}};$$

and wherein each of $r^{11}$, $r^{12}$ and $r^{13}$ represents $C_{1-8}$ hydrocarbon radical; and $r^{14}$ represents $C_{1-12}$ hydrocarbon radical; and $r^{15}$ represents $C_{1-12}$ hydrocarbon radical which may be substituted by halogen or $C_{1-8}$ hydrocarbon-oxycarbonyl; and each of $r^{16}$ and $r^{17}$ represents hydrogen or $C_{1-8}$ hydrocarbon radical; and —T represents $C_{1-16}$ hydrocarbon radical which may be substituted by halogen, nitro, cyano, —Q—$r^{21}$, $C_{1-8}$ hydrocarbon-carbonyloxy, tri-$C_{1-8}$ alkylsilyl, $$-\underset{\underset{O}{\|}}{C}Wr^{22}, \quad -\underset{\underset{Z}{\|}}{C}N\underset{r^{24}}{\overset{r^{23}}{\diagup}}, \quad -\underset{\underset{O}{\|}}{C}-r^{25}, \quad -C=NOr^{26}$$

or heterocyclic radical containing nitrogen; and

—U represents $C_{1-12}$ hydrocarbon which may be substituted by cyano, $C_{1-8}$ hydrocarbon-oxycarbonyl, $C_{1-8}$ hydrocarbon-oxy, $C_{1-8}$ hydrocarbon-thio, tri-$C_{1-8}$ alkylsilyl or —O($CH_2$)$_g$—$_h$O$r^{28}$; and $r^{18}$ represents hydrogen, metal corresponding to one valency or $C_{1-10}$ hydrocarbon radical; and each of $r^{19}$ and $r^{20}$ represents $C_{1-8}$ hydrocarbon radical:

wherein

Q represents —O— or —S(O)$_k$— (k=0, 1 or 2); and $r^{21}$ represents hydrogen or $C_{1-12}$ hydrocarbon radical, which may be substituted by $C_{1-8}$ hydrocarbon-oxy, $C_{1-8}$ hydrocarbon-oxycarbonyl, halogen, nitro or methylendioxy, or $C_{1-8}$ hydrocarbon-carbamoyl; and W represents oxygen or sulfur; and $r^{22}$ represents hydrogen, metal corresponding to one valency, $C_{1-8}$ alkylidene amino, or $C_{1-16}$ hydrocarbon radical which may be substituted by halogen, $C_{1-12}$ hydrocarbon-oxy, $C_{1-12}$ hydrocarbon-thio, $C_{1-8}$ hydrocarbon-carbonyl, $C_{1-8}$ hydrocarbon-oxy-carbonyl-$C_{1-8}$ hydrocarbon-thio, heterocyclic radical containing oxygen (which may be substituted by $C_{1-8}$ hydrocarbon radical) tri-$C_{1-8}$ alkylsilyl or cyano; and Z represents oxygen or sulfur; and each of $r^{23}$ and $r^{24}$ represents hydrogen, $C_{1-8}$ hydrocarbon-oxy, $C_{1-8}$ hydrocarbon-carbamoyl, $C_{1-12}$ hydrocarbon radical, which may be substituted by $C_{1-8}$ hydrocarbon-oxy or $C_{1-8}$ hydrocarbon-oxycarbonyl; and $r^{25}$ represents $C_{1-8}$ hydrocarbon radical; or heterocyclic radical containing nitrogen; and $r^{26}$ represents hydrogen, $C_{1-8}$ hydrocarbon radical or $C_{1-8}$ hydrocarbon-carbonyl which may be substituted by halogen; and $r^{27}$ represents amino, or $C_{1-8}$ hydrocarbon radical; and g represents an integer of 1 to 5; and h represents an integer of 2 to 10, and $r^{28}$ represents $C_{1-8}$ hydrocarbon radical:

In the course of said investigation, the inventors found that the phenyl radical substituted by halogen at 4-position gave high herbicidal activity to the compound and said phenyl radical substituted by halogen having —O(or S)—T or —COK—U (T, K and U have the same meaning as above-mentioned) at 3 or 5-position gave higher herbicidal activity, and further 2—F—4—Cl—5—O(or S)—T or 2—F—4—Cl—5—COK—U phenyl radical created the highest grade herbicidal activity within this invention, by joining with said condensed ring (III).

According to the first aspect of the present invention, there is provided a compound having the formula:

(IV)

wherein X represents —D—E—; and

D represents $-(C)_{\overline{a}}-$ (a = 0 or 1); and with $r^5$ above and $r^6$ below the C; and

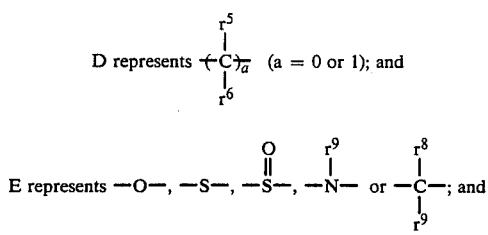

E represents $-O-$, $-S-$, $-\overset{O}{\underset{\|}{S}}-$, $-\overset{r^9}{\underset{|}{N}}-$ or $-\overset{r^8}{\underset{|}{\underset{r^9}{C}}}-$; and each of $r^1$ to $r^9$: hydroxy, $C_{1-8}$ hydrocarbon radical which may be substituted by halogen, $C_{1-8}$ hydrocarbon-oxy or $C_{1-8}$ hydrocarbon-thio, $C_{1-8}$ hydrocarbon-carbonyloxy or $C_{1-8}$ hydrocarbon-oxycarbonyl, and $r^1$, $r^2$, $r^3$, $r^4$, $r^5$, $r^6$, $r^7$, $r^8$ and $r^9$ may form ring(s) or $C_{1-8}$ alkylidene(s) by joining each other.

Y represents $$-O- \text{ or } -S- \text{ or } -\overset{O}{\underset{\|}{S}}-;$$

and each of R and n represents as same as above-mentioned.

In this invention and in the claims of this invention, the word "hydorcarbon" or "hydrocarbon radical" means and includes linear, branched or cyclic alkyl, alkenyl or alkynyl; or aryl, aralkyl or alkylaryl. And "heterocyclic radical containing nitrogen means heterocyclic radical containing nitrogen in which oxygen and/or sulfur atom(s) may be contained, and "heterocyclic radical containing oxygen" means hetrocyclic radical containing oxygen in which nitrogen atom(s) may be contained.

According to the second aspect of the present invention there is provided a herbicidal composition comprising an inert carrier and an effective amount of the compound having the formula (IV).

The compounds of the present invention have little phytotoxicities to the crops such as corn, wheat, soybeans, peanuts, alfalfa, etc., while they possesses superior herbicidal activity against wide varieties of weeds such as common lambsquater, redroot pigweed, flatsedge, etc., irrespective of their growth stage. Particularly, the compounds show higher herbicidal activity in post emergence treatment.

The group of compounds having the formula (IV), in which X represents $-CH_2-$ and Y represents S and (R)n represents 2—F—4—Cl 5-substituted by alkoxycarbonylalkoxy, alkoxycarbonylalkoxylcarbonyl or alkoxycarbonylalkylthio, exhibited the highest herbicidal activity and selectivity for soybeans in post emergence treatment.

The compounds also exhibit high selectivity on rice plant and high herbicidal activity against barnyardgrass, monochoria, smallflower unbrella sedge, etc., regardless of their growth stage. Particularly, compounds having 2—F—4—Cl—5—$C_{1-8}$ alkynyloxyphenyl radical exhibit higher selectivity and activity.

Further, they can be applied for the control of the weeds in orchards, lawn, roadway sides, vacant lots, etc.

According to a third aspect of the present invention, there is provided a process for the preparation of the compound of the formula (IV), comprising the step of reaction is illustrated by the following equation.

1. in case Y being sulfur and X being E (5 membered ring):

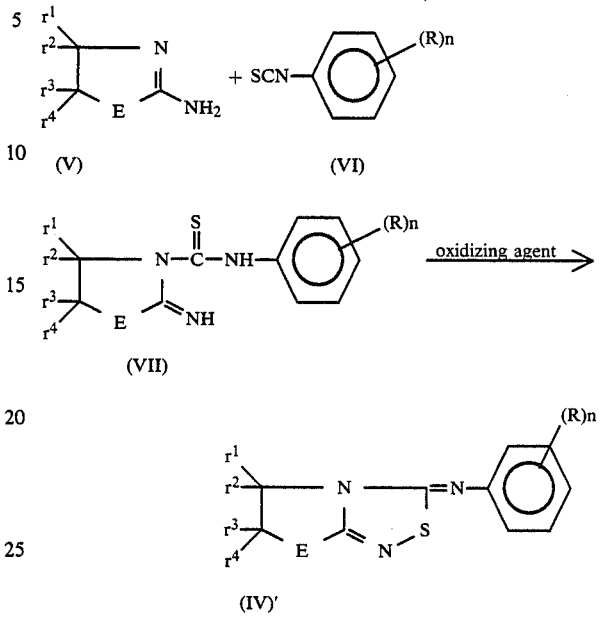

A compound having the formula (V) is reacted with a compound having the formula (VI) in an inert solvent, for example, ether, methylene dichloride, chloroform, ethyl acetate, for 0.5–10 hours at a temperature from $-50°$ C. to 50° C. The obtained compound having the formula (VII) rearranges comparatively easily into the thio urea derivative having the formula

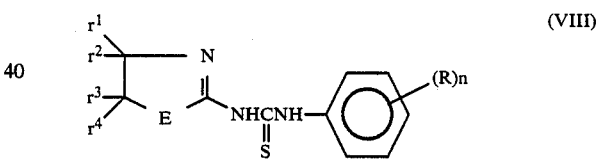

when heated in the solvent.

Because of such unstability, it is desirable to be subjected to the following reaction without isolation.

Ring formation is carried out by using oxidizing agent in an organic solvent. As the organic solvent, a general inert solvent such as methylene dichloride, chloroform, N,N-dimethylformamide, ethyl acetate can be used.

At the condensation reaction of ring formation, acid binder(s) may be effectively used according to the kind of oxidizing agent. As the acid binder, an organic base such as triethylamine, pyridine, dimethyl aniline, or an inorganic base such as caustic soda, sodium carbonate, can be use. As the oxidizing agent, bromine, chlorine, sodium hypochlorite or the like are used. In case at least one of R being hydroxy, iodine is preberable as the oxidizing agent.

The compound having the formula (IV)' thus produced may be obtained by a usual procedure of separation and then purified by a conventional purifying procedure such as recrystallization, column chromatography etc.

2. in case Y being oxygen:

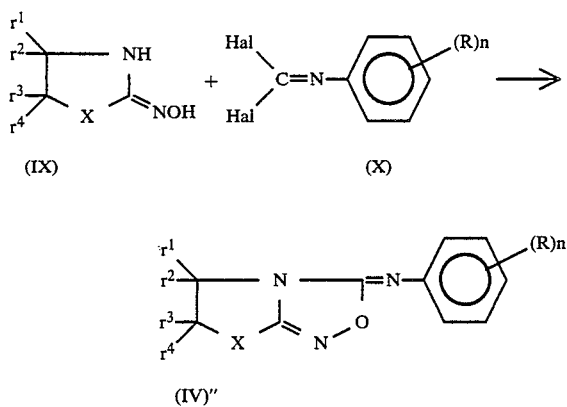

(IX)   (X)

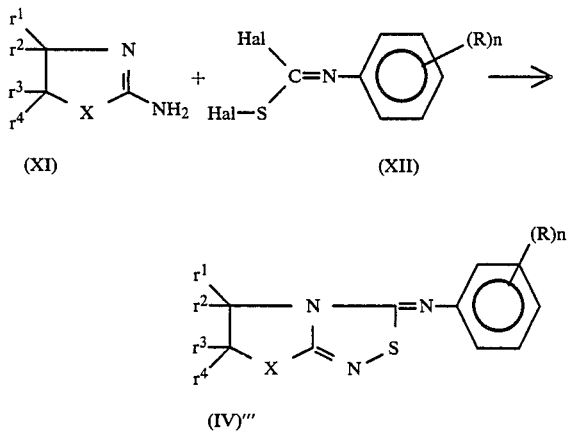

(IV)″

The reaction is carried out in the presence of organic or inorganic base in an inert solvent for one (1) to several tens of hours at a temperature from −20° C. to 50° C. As the base, triethylamine, pyridine, sodium carbonate etc. can be used, and as the solvent, methylene dichoride, chloroform etc. can be used.

The compound having the formula (IV)″ thus produced may be obtained by a usual procedure of separation and then purified by a conventional purifying procedure such as recrystallization, column chromatography etc.

3. in case Y being sulfur:

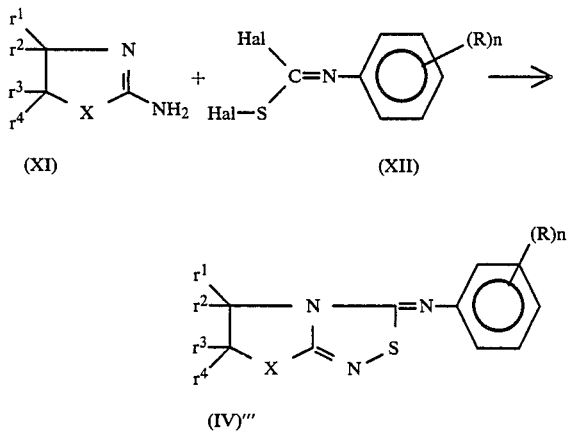

(XI)   (XII)

(IV)‴

The reaction is carried out in the presence of organic or inorganic base in an inert solvent for one (1) to 10 hours at a temperature from −20° C. to 50° C. As the base, triethylamine, sodium carbonate, etc. can be used, and as the solvent methylene dichloride, chloroform, etc. can be used. The compound obtained having the formula (IV)‴ thus produced may be obtained by a usual procedure of separation and then purified by a conventional purifying procedure such as recrystallization, column chromatography, etc.

The starting material having the formula (XII) can be prepared by chlorination of the corresponding isothiocyanate, and normally, the obtained compound is used to the following reaction without being isolated.

4. in case Y or E being SO, the compound is obtained by oxidation of the corresponding sulfur compound.

And the present compound is also obtainable by the following equation:

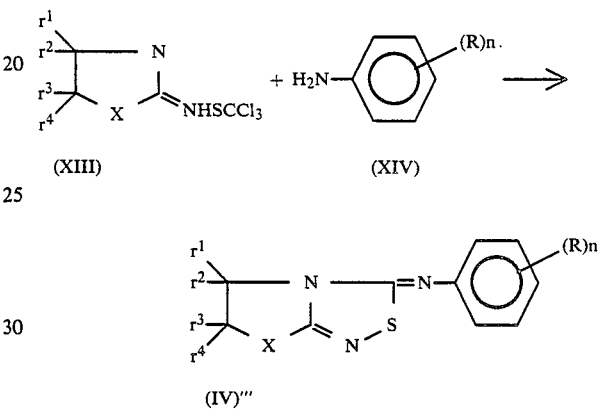

(XIII)   (XIV)

(IV)‴

Further, owing to the difference of substituent(s) shown by —(R)n, a proper reaction is selected from following equations to prepare the compounds of this invention:

a. in case —GR$^1$ type (R$^1$ is not hydrogen):

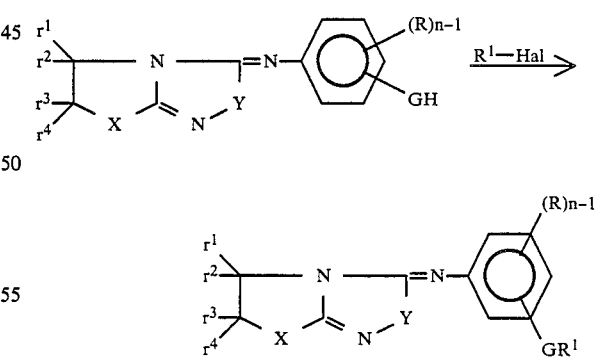

b. in case

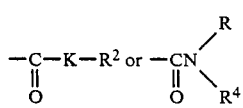

type (R$^2$ is not hydrogen):

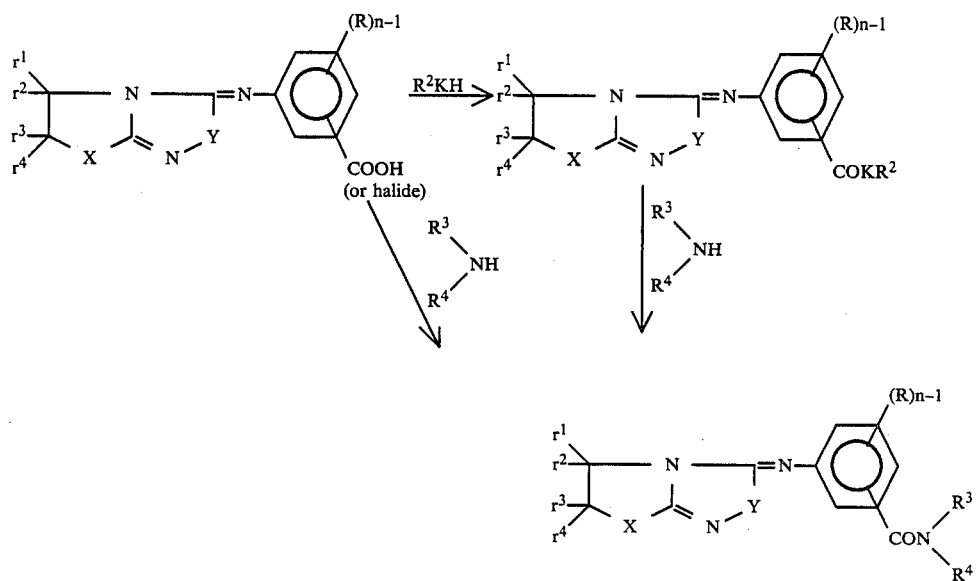
c. in case —NH$_2$ type (G: nitrogen, and r$^{10}$ and R$^1$: hydrogen):
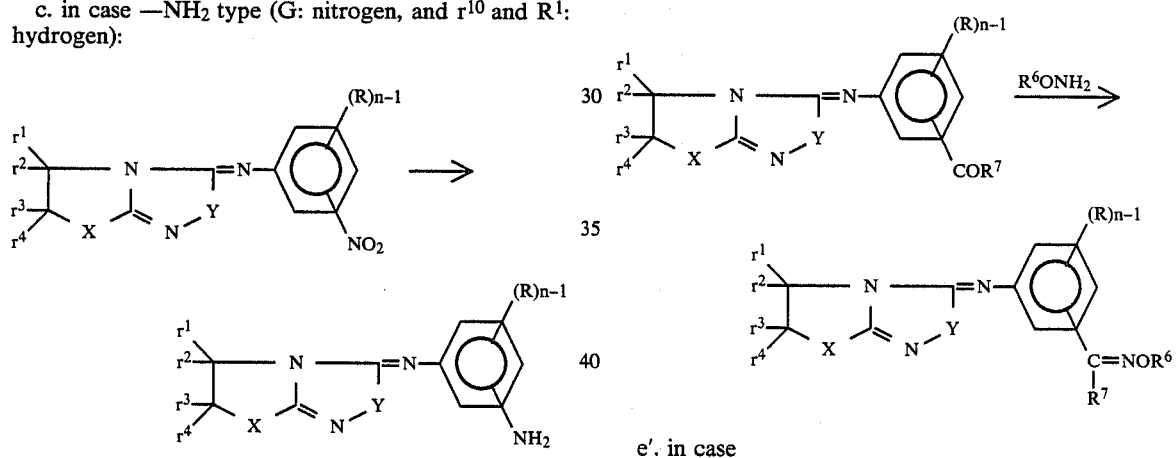
d. in case —SR$^1$ type (—G: S):
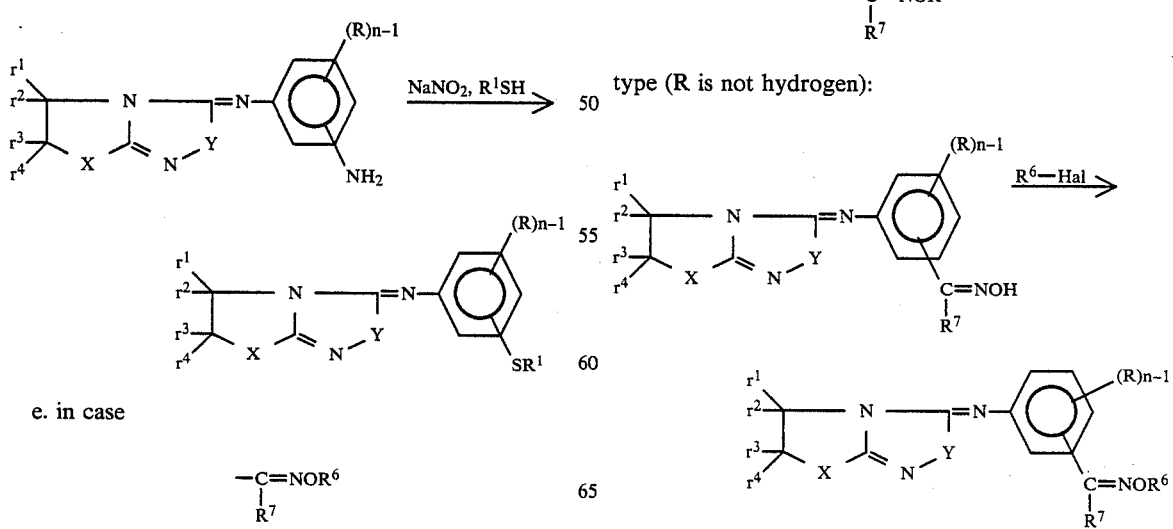
e. in case
$$-\underset{R^7}{\overset{}{C}}=NOR^6$$
type:
e'. in case
$$-\underset{R^7}{\overset{}{C}}=NOR$$
type (R is not hydrogen):
f. in case

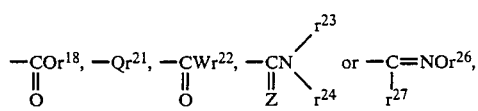

the compound is obtainable by similar reaction to the above.

The chemical structure of the compound obtained was determined by means of NMR spectrum, Mass spectrum and IR spectrum.

The following Examples illustrate the invention.

EXAMPLE 1

3-(5-acetonyloxy-4-chloro-2-fluorophenylimino)-5,6-dihydro-6,6-dimethyl-3H-thiazolo(2,3-C)(1,2,4)thiadiazole (Compound No. 232)

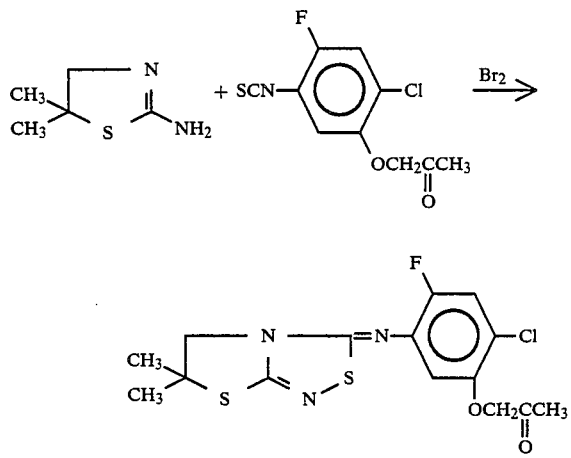

1.5 g of 2-amino-5,5-dimethyl-2-thiazoline was dissolved in 15 ml of methylene dichloride. To this was then added dropwise, under stirring at 0° C., a solution of 3.0 g of 2-fluoro-4-chloro-5-acetonyloxyphenylisothiocyanate in 15 ml of methylene dichloride. After it was then stirred for one hour, the reaction solution was fed with 0.72 g pyridine, and while being ice-cooled, to the solution was added dropwise a solution of 1.7 g of bromine in 10 ml of methylene dichloride. The reaction solution was further stirred for 30 minutes, at the end of which the solution was washed with 30 ml of water, with 30 ml of 5% NaOH solution, and with 30 ml of water, in the order given. The methylene dichloride layer was dried over anhydrous magnesium sulfate. The same layer was filtered and then concentrated. The residue was purified by silica gel column chromatography to give 2.5 g of the objective product. (m.p. 107°–108° C.)

EXAMPLE 2

3-((4-chloro-2-fluoro-5-(1-ethoxycarbonylethoxy)-phenylimino))-5,6-dihydro-6-methyl-3H-oxazolo(2,3-C)(1,2,4)thiadiazole (Compound No. 359)

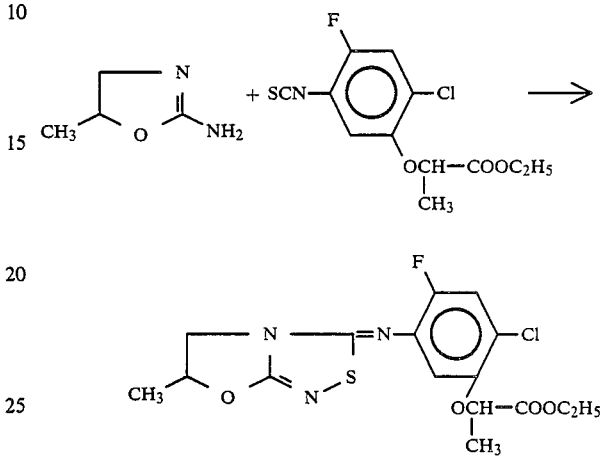

9.60 g of 4-chloro-2-fluoro-5-(1-ethoxycarbonylethoxy)phenyl isothiocyanate was dissolved in 100 ml of chloroform. The solution was then cooled to −10° C. and was fed with 3.80 g of 5-methyl-2-amino-2-oxazoline. The reaction solution was stirred for five hours at 0° C., and then a solution of 5.06 g of bromine in 30 ml of chloroform was added dropwise at −10°–0° C. After the dropwise addition ended, the reaction solution was washed with a 50 ml aqueous solution of 1N-NaOH, then with 50 ml water, and was dried over anhydrous magnesium sulfate. After magnesium sulfate was filtered off, chloroform was removed in vacuo. The residue obtained was purified by column chromatography to give 10.04 g of objective product. ($n_D^{26}$ 1.5870)

EXAMPLE 3

3-(4-chloro-5-(1-cyanoethoxy)-2-fluorophenylimino)-6,7-dihydro-6-methyl-3H,5H-pyrrolo(2,1-C)(1,2,4)thiadiazole (Compound No. 587)

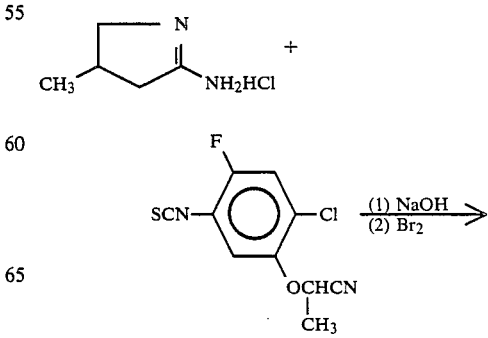

-continued

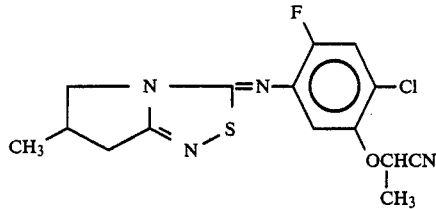

3.25 g of 2-amino-4-methyl-1-pyrroline hydrochloride was suspended to 20 ml of chloroform. While it was ice-cooled, to the suspension was add dropwise a solution of 1 g of caustic soda in 60 ml of water. After 10 minutes of stirring, the reaction mixture, while it was ice-cooled, was further fed dropwise with a solution of 5.6 g of 2-fluoro-4-chloro-5-(1-cyanoethoxy)phenylisothiocyanate in 20 ml of chloroform. After stirring it for three hours at room temperature, the reaction solution was fed dropwise with a solution of 3.15 g of bromine in 10 ml of chloroform under ice-cooling. After stirring at room temperature for one hour, the reaction solution was washed with 30 ml of water. The chloroform layer was dried over anhydrous magnesium sulfate and was then filtered. The filtrate was concentrated and the residue was purified by silica gel column chromatography to give 5.0 g of the objective product. (m.p. 93°–95° C.)

EXAMPLE 4

3-(4-chloro-5-(1-ethoxycarbonylethoxy)-2-fluorophenylimino)-5,6-dihydro-7-methyl-3H-imidazo(2,1-C)(1,2,4)thiadiazole (Compound No. 675)

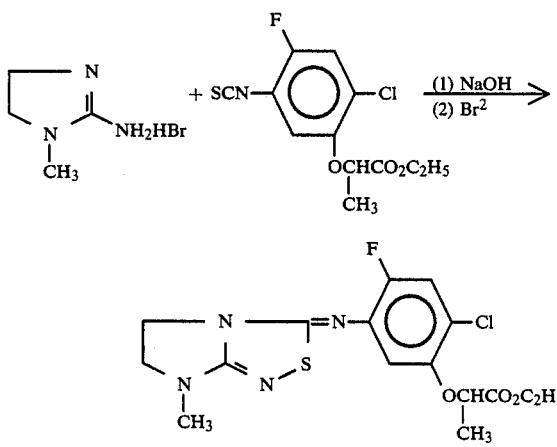

1.56 g of 2-amino-3-methyl-1-imidazoline hydrobromide was suspended in 10 ml of chloroform. To this suspension was then added dropwise, under ice-cooled conditions, a solution of 0.37 g of caustic soda in 2 ml of water. After cooling it down to −15° C., the reaction solution was fed dropwise with a solution of 2.31 g of 2-fluoro-4-chloro-5-(1-ethoxycarbonylethoxy)-phenylisothiocyanate in 10 ml of chloroform. After stirring it for one hour at −15° C., the reaction solution was again fed dropwise with a solution of 1.2 g of bromine in 10 ml of chloroform. After another hour of stirring the reaction solution was washed with 30 ml of water and the chloroform layer was dried over anhydrous magnesium sulfate before it was concentrated. The residue obtained was purified by silica gel column chromatography to give 1.48 g of the objective product. (m.p. 75°–78° C.)

EXAMPLE 5

3-(4-chloro-2-fluoro-5-isopropoxyphenylimino)-5,6-dihydro-6,6-dimethyl-3H-thiazolo(2,3-C)(1,2,4)oxadiazole (Compound No. 129)

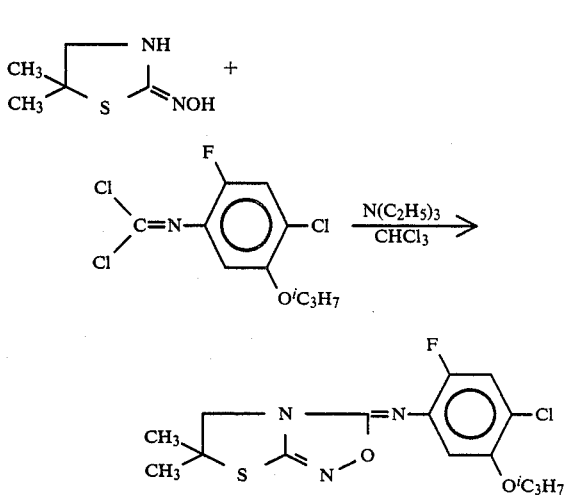

To a solution of 5,5-dimethyl-2-hydroxyiminothiazolidine (1.5 g) and triethylamine (3 g) in chloroform (30 ml) was added dropwise a solution of 4-chloro-2-fluoro-5-isopropoxyphenylisocyanide dichloride (2.8 g) in chloroform (10 ml) at 5°–10° C., and the mixture was stirred at room temperature overnight. The reaction mixture was washed with water, dried over anhydrous magnesium sulfate. Chloroform was removed in vacuo, and the residue was purified by silica gel column chromatography to give 0.8 g of the objective product. ($n_D^{20}$ 1.5760)

EXAMPLE 6

3-(4-chloro-5-(1-ethoxycarbonyl ethoxy)-2-fluorophenylimino)-5,6,7,8-tetrahydro-(1,2,4)thiadiazole-(4,3-a)pyridine (Compound No. 679)

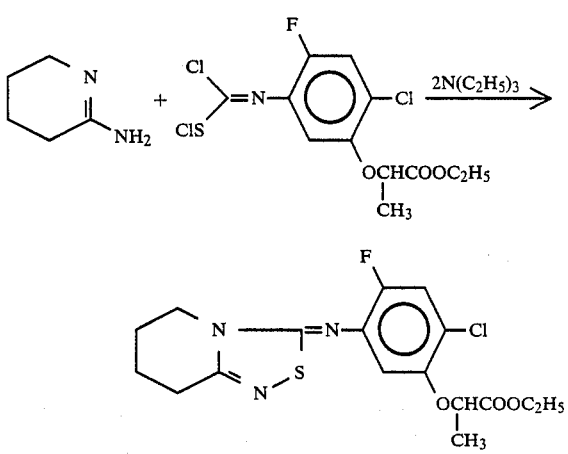

The solution of 4-chloro-5-(1-ethoxycarbonylethoxy)-2-fluoro phenyl isothiocyanate (2.0 g) in carbon tetrachloride (10 ml) was added dropwise at 0° C. with stirring to chlorine (0.9 g) in carbon tetrachloride (25 ml).

After stirring at room temperature for 16 hours, the reaction mixture was concentrated under a reduced pressure.

The residue was dissolved in chloroform, and 2-amino-3,4,5,6-tetrahydropyridine (0.51 g) and triethylamine (1.10 g) was added and stirred at 0° C. for 2 hours.

Water was added, and the mixture was extracted with chloroform, dried over anhydrous magnesium sulfate, and concentrated.

The residue was purified by silica gel column chromatography (hexane-ethyl acetate 2:1) to give 0.18 g of the objective product. (m.p. 79°-80.5° C.)

EXAMPLE 7

3-(4-chloro-2-fluoro-5-(0,0-dimethylthio phosphoryloxy)phenylimino)-5,6-dihydro-6-methyl-3H-oxazolo(2,3-C)(1,2,4)thiadiazole (compound No. 518)

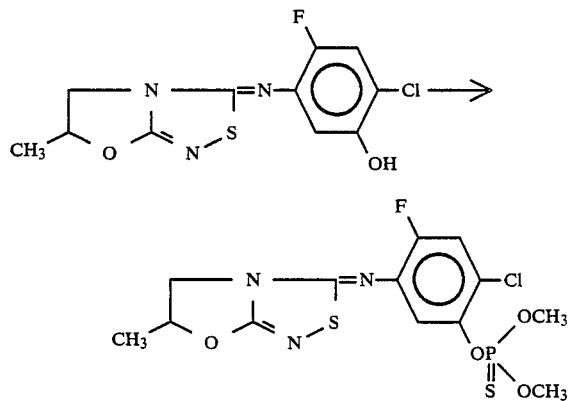

0.6 g of 3-(4-chloro-2-fluoro-5-hydroxyphenylimino)-5,6-dihydro-6-methyl-3H-oxazolo(2,3-C)(1,2,4)thiadiazole and 0.27 g of anhydrous potassium carbonate were added to 40 ml of acetone. At room temperature, the reaction solution was fed dropwise with 0.32 g of 0,0-dimethylthiophosphoryl chloride. The solution was heated under reflux for four hours, and was then cooled, thereupon solid matter was filtered off and the filtrate was concentrated under reduced pressure. The residue was purified by column chromatography to give 0.3 g of the objective product. (m.p. 77°-80° C.)

EXAMPLE 8

3-(4-chloro-2-fluoro-5-(1-ethylthiocarbonylethoxy)-phenylimino)-5,6-dihydro-6-methyl-3H-oxazolo(2,3-C)(1,2,4)thiadiazole (Compound No. 410)

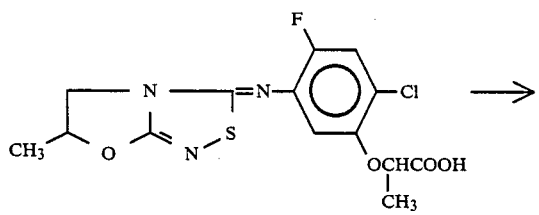

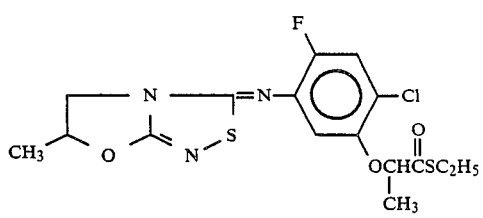

1.00 g of 3-(4-chloro-2-fluoro-5-(1-carboxyethoxy)-phenylimino)-5,6-dihydro-6-methyl-3H-oxazolo(2,3-C)(1,2,4)thiadiazole was dissolved in 30 ml of chloroform. Under stirring at −10° C., the solution was fed with 0.30 g of triethylamine and 0.3 g of methyl chlorocarbonate. After five minutes elapsed, the solution was further fed with 0.20 g of ethyl mercaptan and was stirred for three hours at 0° C. The reaction solution was poured into 50 ml dilute hydrochloric acid to separate the chloroform layer out. The chloroform layer was washed with 30 ml of 1N-NaOH, then with 30 ml of water, and was dried over anhydrous magnesium sulfate. When this was accomplished, magnesium sulfate was filtered off, and the filtrate was concentrated. The residue was purified by column chromatography and the objective product was obtained as an oil in an amount of 0.5 g.

($n_D^{26}$ 1.6080)

EXAMPLE 9

3-(4-chloro-2-fluoro-5-(2-hydroxyimino-propoxy)-phenylimino)-5,6-dihydro-6,6-dimethyl-3H-thiazolo(2,3-C)(1,2,4)thiadiazole (Compound No. 191)

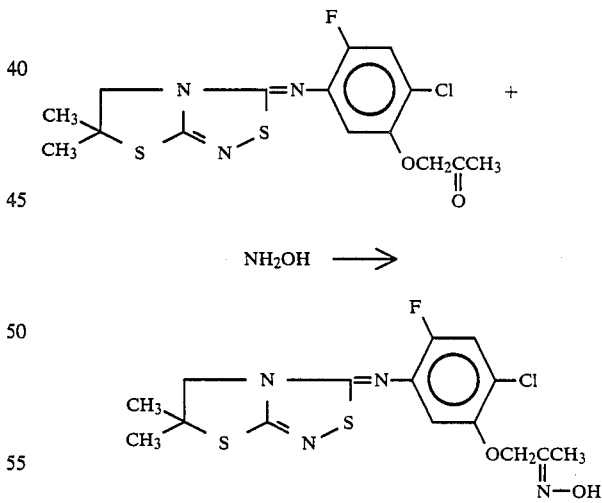

0.9 g of 3-(5-acetonyloxy-4-chloro-2-fluoro-phenylimino)-5,6-dihydro-6,6-dimethyl-3H-thiazolo(2,3-C)(1,2,4)thiadiazole and 0.25 g of hydroxyamine hydrochloride were dissolved in 10 ml of ethanol. The solution obtained was fed dropwise under stirring at room temperature with a solution of 0.14 g of caustic soda in 10 ml of water. After one hour of stirring at room temperature, the reaction solution was poured into 60 ml of water and the crystals that precipitated were filtered and washed with water to give 0.8 g of the objective product. (m.p. 152°-156° C.)

EXAMPLE 10

3-(4-chloro-5-fluoro-5-(1-(1-phenyl-2-propynyloxycarbonyl)ethoxy
phenylimino)-6,7-dihydro-6-methyl-3H,5-pyrrolo(2,1-C)(1,2,4)thiadiazole (Compound No. 610)

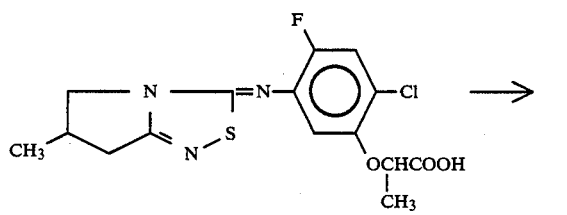

→

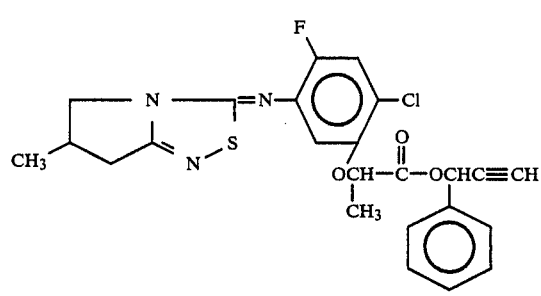

1.00 g of 3-(4-chloro-2-fluoro-5-(1-carboxyethoxy)-phenylimino)-6,7-dihydro-6-methyl-3H,5H-pyrrolo(2,1-C)(1,2,4)thiadiazole was added to 10 ml of benzene, to which were then added under stirring at room temperature 0.83 g of thionyl chloride and a drop of pyridine. 20 hours of heating under reflux produced a corresponding acid chloride. The low-boiling component was distilled off under reduced pressure. The residue was again fed with 10 ml of benzene, and further at room temperature with 0.73 g of 1-phenyl-2-propyne-1-ol and with 0.44 g of pyridine, and was stirred for four hours. The reaction solution was poured into water to separate the benzene layer. The water layer was extracted with 30 ml of ethyl acetate. The organic layer, was combined, washed with 20 ml of 5% hydrochloric acid water, with 20 ml of 5% sodium hydrogen carbonate, and with 20 ml of saline solution in this order. After it was dried over anhydrous magnesium sulfate, the solvent was distilled off under reduced pressure and the residue was purified by column chromatography to give 0.4 g of the objective product.
($n_D^{21}$1.5957)

EXAMPLE 11

3-(4-chloro-5-(1-thiocarbamoylethoxy)-2-fluoro-phenylimino)-6-6,7-dihydro-6-methyl-3H,5H-pyrrolo(2,1-C)(1,2,4)thiadiazole (Compound No. 614)

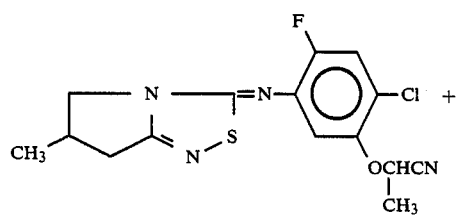

+

-continued

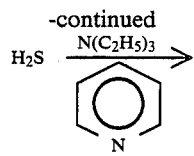

$\xrightarrow{H_2S \quad N(C_2H_5)_3}$

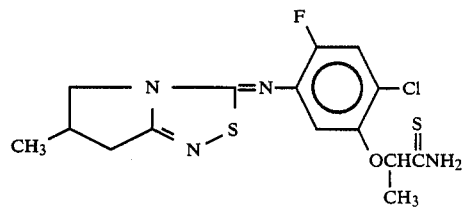

1 g of 3-(4-chloro-5-(1-cyanoethoxy)-2-fluorophenylimino)-6,7-dihydro-6-methyl-3H,5H-pyrrolo(2,1-C)(1,2,4)thiadiazole and 0.3 g of triethylamine were dissolved in 2 ml of pyridine. To the solution, while it was ice-cooled, was gradually introduced hydrogen sulfide. The reaction mixture was TLC-analyzed with the progress of time and the reaction stopped as soon as raw material spot disappeared. The reaction liquid was fed with 10 ml of ethyl acetate and was washed with dilute hydrochloric acid. The ethylacetate layer was rinsed, dried over anhydrous magnesium sulfate filtered, and, concentrated under reduced pressure. The residue was purified by silicagel column chromatography to give 0.5 g of the objective product. (m.p. 134.5°–135° C.)

EXAMPLE 12

3-(4-chloro-5-(1-(N-chloroacetoxyamidino)ethoxy)-2-fluorophenylimino)-6,7-dihydro-6-methyl-3H,5H-pyrrolo(2,1-C)(1,2,4)thiadiazole (Compound No. 577)

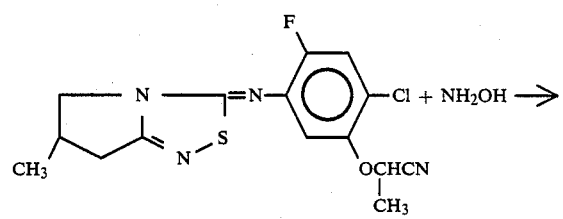

+ NH₂OH →

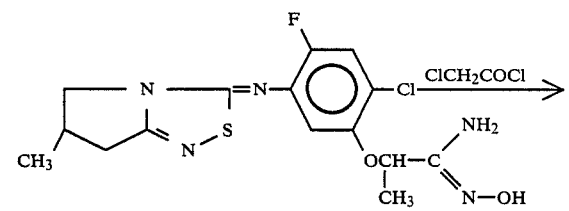

$\xrightarrow{ClCH_2COCl}$

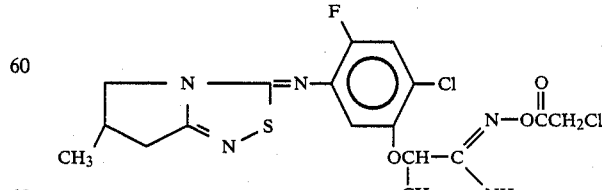

1 g of 3-(4-chloro-5-(1-cyanoethoxy)-2-fluorophenylimino)-6,7-dihydro-methyl-3H,5H-pyrrolo(2,1-

C)(1,2,4)thiadiazole was dissolved in ethanol, to which was then added dropwise under stirring at room temperature a solution of 0.23 g hydroxylamine hydrochloride and 0.23 g anhydrous potassium carbonate in 3 ml of water. This reaction mixture was heated under reflux for two hours, at the end of which it was poured into ice-cooled water. The crystals that precipitated out were filtered, rinsed, and then dried, and 0.9 g of crude amidoxime was obtained. 0.9 g of crude amidoxime and 0.25 g of triethylamine were dissolved in 10 ml of THF, to which was then added dropwise, under ice-cooled conditions, a solution of 0.27 g of chloroacetyl chloride in 5 ml of THF. After it was stirred for one hour at 50° C., the reaction solution was charged with 40 ml of water and 40 ml of chloroform. The chloroform layer was dried over anhydrous magnesium sulfate, and concentrated under reduced pressure. The residue obtained was then recrystallized from benzene to give 0.4 g of the objective product. (d.p. 128°–129° C.)

EXAMPLE 13

3-(5-carboxy-4-chloro-2-fluorophenylimino)-6,7-dihydro-6-methyl-3H,5H-pyrrolo(2,1-C)(1,2,4)thiadiazole (Compound No. 561)

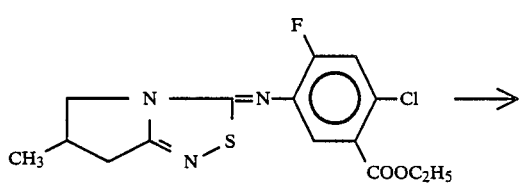

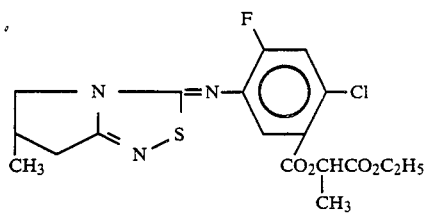

-continued

To a solution of 3-(4-chloro-2-fluoro-5-ethoxycarboxylphenylimino)-6,7-dihydro-6-methyl-3H,5H-pyrrolo(2,1-C)(1,2,4)thiadiazole (8.5 g) in tetrahydrofuran (60 ml) and methanol (30 ml) was added a aqueous solution (50 ml) of sodium hydroxide (2.9 g) at room temperature, and the mixture was stirred at 50° C. for 0.5 hour. The reaction mixture was acidified with 1N hydrochloric acid, and concentrated to half volume. The residue was extracted with ethylacetate, washed with water, dried over anhydrous magnesium sulfate, and concentrated. The residue was crystallized from ether-n-hexane to give 7.5 g of the objective compound. (m.p. 210°–213° C.)

EXAMPLE 14

3-(4-chloro-5-(1-ethoxycarbonylethoxycarbonyl)-2-fluorophenylimino)-6,7-dihydro-6-methyl-3H,5H-pyrrolo(2,1-C)(1,2,4)thiadiazole (Compound No. 683)

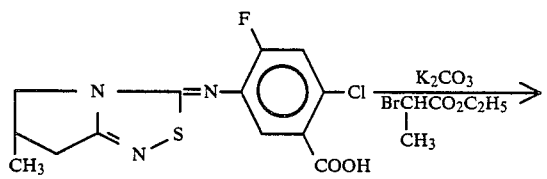

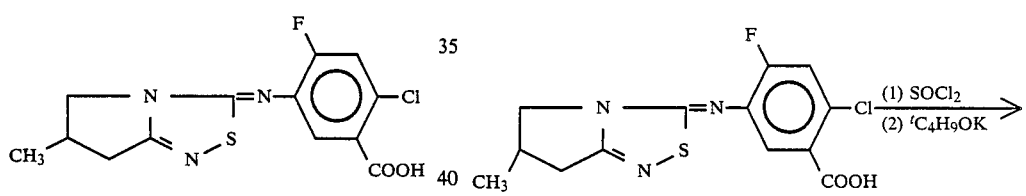

To a solution of 3-(5-carboxy-4-chloro-2-fluorophenylimino)-6,7-dihydro-6-methyl-3H,5H-pyrrolo(2,1-C)(1,2,4)thiadiazole (0.7 g) in acetonitrile (10 ml), there were added anhydrous potassium carbonate (0.3 g) and 2-bromopropionic acid ethyl ester (0.4 g) and the mixture was heated at reflux for 4 hours. After being allowed to cool to room temperature, the reaction mixture was filtered, and the filtrate was concentrated under reduced pressure. The residue was recrystallized from ether-hexane to give 0.8 g of the objective product. (m.p. 83°–84° C.)

EXAMPLE 15

3-(4-chloro-2-fluoro-5-tert-butoxycarbonyl phenylimino)-6,7-dihydro-6-methyl-3H,5H-pyrrolo(2,1-C)(1,2,4)thiadiazole (Compound No. 537)

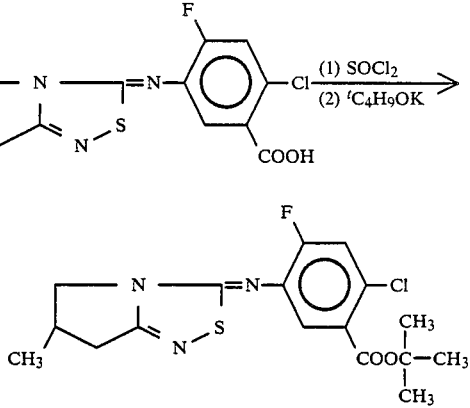

To a solution of 3-(5-carboxy-4-chloro-2-fluorophenylimino)-6,7-dihydro-6-methyl-3H,5H-pyrrolo(2,1-C)(1,2,4)thiadiazole (3 g) in benzene (20 ml), there was added thionyl chloride 3.3 g), and the mixture was heated at reflux for 0.5 hour. The reaction mixture was concentrated under reduced pressure, the residue, which was dissolved in benzene (20 ml), was dropwise added to the suspension of potassium test-butoxide (2.1 g) in benzene (20 ml) at 5°–10° C. After stirring at room temperature for 2 hours, cold water was added to this reaction mixture. The benzene layer was washed with water, and dried over anhydrous magnesium sulfate. Benzene was removed in vacuo, and the residue was recrystallized from ether-n-hexane to give 1.5 g of the objective product. (m.p. 89°–90° C.)

EXAMPLE 16

3-(4-chloro-2-fluoro-5-(2-propynylamino)phenylimino)-5,6-dihydro-6,6-dimethyl-3H-thiazolo(2,3-C)(1,2,4)thiadiazole (Compound No. 108)

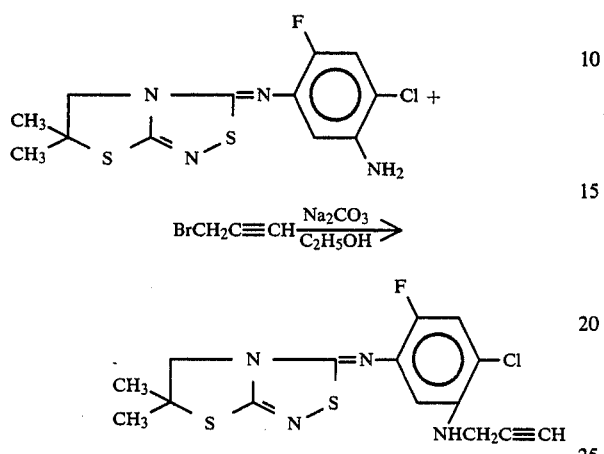

To 3-(5-amino-4-chloro-2-fluorophenylimino)-5,6-dihydro-6,6-dimethyl-3H-thiazolo-(2,3-C)(1,2,4)thiadiazole (1.69 g) in ethanol (20 ml) was added anhydrous sodium carbonate (0.82 g) and 2-propynyl bromide (0.77 g).

The resultant mixture was refluxed for 19 hours. After being allowed to cool, water was added, and the mixture was extracted with chloroform, dried over anhydrous magnesium sulfate, and concentrated.

The residue was purified by silicagel column chromatography (benzenechloroform 2:1) to give 1.17 g of the objective product. (m.p. 117°–117.5° C.)

EXAMPLE 17

3-(5-amino-4-chloro-2-fluorophenylimino)-5,6-dihydro-6,6-dimethyl-3H-thiazolo-(2,3-C)(1,2,4)thiadiazole (Compound No. 105)

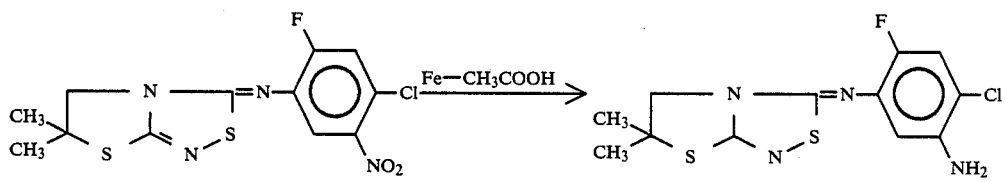

3-(4-chloro-2-fluoro-5-nitrophenylimino)-5,6-dihydro-6,6-dimethyl-3H-thiazolo-(2,3-C)(1,2,4)thiadiazole (5.28 g) was dissolved in methyl ethyl ketone (40 ml), and acetic acid (1.96 g), iron powder (3.86 g), water (20 ml) was added.

The resultant mixture was stirred at room temperature for 30 minutes, and 70° C. for 1.5 hours. After being allowed to cool 20% aqueous sodium hydroxide (20 ml) and ethyl acetate (40 ml) was added to the resultant mixture, followed by filtration on celite.

The organic layer was separated and the aqueous layer was extracted with chloroform, and the extracts were combined, dried over anhydrous magnesium sulfate and concentrated.

The residue was purified by silicagel column chromatography (benzene-CHCl₃ 1:6) to give 2.02 g of the objective product. (m.p. 141°–142° C.)

EXAMPLE 18

3-(4-chloro-2-fluoro-5-carboxymethylthiophenylimino)-6,7-dihydro-6-methyl-3H,5H-pyrrolo(2,1-C)(1,2,4)thiadiazole (Compound No. 740)

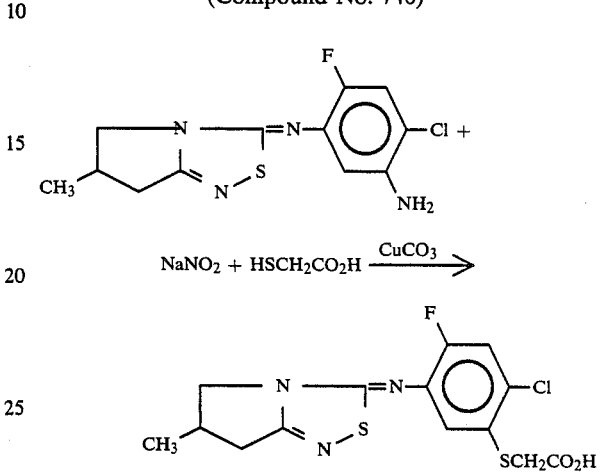

To the solution of 2.0 g of 3-(4-chloro-2-fluoro-5-aminophenylimino-6,7-dihydro-6-methyl-3H,5H-pyrrolo(2,1-C)(1,2,4)thiadiazole in 5 ml of concentrated sulfuric acid and 50 ml of water was added 0.56 g of sodium nitrate in 5 ml of water at −5°–0° C. The reaction mixture was stirred for 30 minutes, then 0.1 g of urea was added to destroy excess sodium nitrite. 0.8 g of thiogycolic acid and 0.5 g of cupric carbonate in 10 ml of water was added to the reaction mixture at room temperature and stirred for one hour. The reaction mixture was extracted with ethyl acetate, organic layer was washed with water, dried over anhydrous magnesium sulfate and concentrated.

The residue was purified by silicagel column chromatography to obtain 0.5 g of the objective compound.

EXAMPLE 19

3-(4-chloro-2-fluoro-5-isopropoxycarbonylmethylthiophenylimino)-6-methyl-5,6,7,7a-tetrahydro-3H-pyrrolo(2,1-C)(1,2,4)thiadiazole (Compound No. 707)

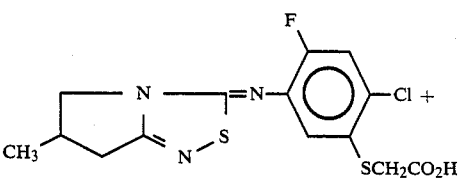

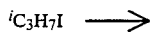

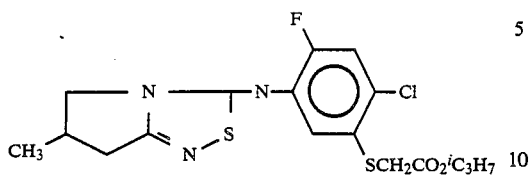

0.4 g of 3-(4-chloro-2-fluoro-5-carboxymethylthio-phenylimino)-6-methyl-5,6,7,7a-tetrahydro-3H-pyr-rolo(2,1-C)(1,2,4)thiadiazole, 0.22 g of isopropyl iodide, 0.15 g of anhydrous potassium carbonate and 10 ml of acetonitrile were mixed together and heated to reflux for 3 hours. After being allowed to cool the precipitate was filtered off. The filtrate was concentrated under reduced pressure. The residue was purified by silicagel column chromatography to obtain 0.2 g of the objective product. (m.p. 79°–82° C.)

EXAMPLE 20

Oxidation of 3-(4-chlorophenylimino)-6,6-dimethyl-5,6-dihydro-3H-thiazolo(2,3-C)(1,2,4)thiadiazole (Compound No. 36 and 81)

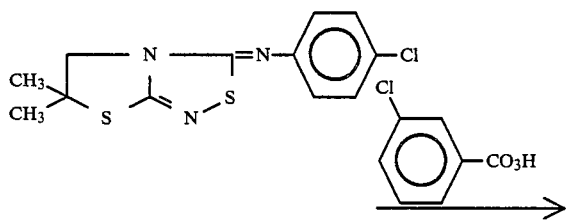

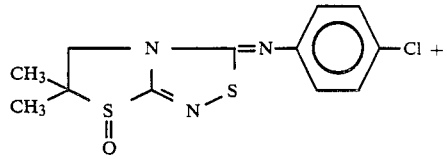

To a solution of 3-(4-chlorophenylimino)-6,6-dimethyl-5,6-dihydro-3H-thiazolo(2,3-C)(1,2,4)thiadiazole (2.2 g) in dichloromethane (20 ml) was added a solution of m-chloroperbenzoic acid (3.0 g) in dichloromethane (20 ml) at room temperature. After stirring for 2 hours at room temperature, the reaction mixture was filtered. The filtrate was washed with 10% aqueous sodium hydroxide solution, dried over anhydrous magnesium sulfate and concentrated.

The residue was purified by silicagel column chromatography to obtain 0.6 g of 3-(4-chlorophenylimino)-6,6-dimethyl-5,6-dihydro-3H-thiazolo(2,3-C)(1,2,4)thiadiazole-2-oxide (m.p. 121°–124° C.) and 0.6 g of 3-(4-chlorophenylimino)-6,6-dimethyl-5,6-dihydro-3H-thiazolo(2,3-C)(1,2,4)thiadiazole-7-oxide. (m.p. 115°–120° C.)

Inclusive the above, each compound within the scope of this invention which can be prepared in analogous method(s) is tabulated in Table 1.

TABLE 1

Structure formula

| Compound No. | X | Y | $r^1, r^2, r^3, r^4$ | (R)n | Physical Properties m.p. °C. |
|---|---|---|---|---|---|
| 1 | S | S | 6,6-$(CH_3)_2$ | 5-$CF_3$ | 71–72 |
| 2 | " | " | " | 4-Cl, 5-$CF_3$ | 103–104 |
| 3 | " | " | " | 2-F, 4-Cl, 5-$CH_2Cl$ | 89–90 |
| 4 | " | " | " | 2-F, 4-Cl, 5-$CH_2OCH_3$ | 80–83 |
| 5 | " | " | " | 2-F, 4-Cl, 5-$CH_2OCOCH_3$ | 96–97 |
| 6 | " | " | " | 2-F, 4-Cl, 5-$CH_2OH$ | 169–170 |
| 7 | " | " | " | 2-F, 4-Cl, 5-CH=CHCOOC$_2$H$_5$ | 89–91 |
| 8 | " | " | " | 2-F, 4-Cl, 5-CH=NOC$_2$H$_5$ | $n_D^{22.5}$ 1.6334 |
| 9 | " | " | " | 2-F, 4-Cl, 5-CH=NOCH$_2$COOC$_2$H$_5$ | 113–114 |
| 10 | " | " | " | 2-F, 4-Cl, 5-COOC$_2$H$_4$OCH$_3$ | 105–107 |
| 11 | " | " | " | 2-F, 4-Cl, 5-COOC$_2$H$_5$ | 108–109 |
| 12 | " | " | " | 4-Cl, 5-COOC$_2$H$_5$ | 74–77 |
| 13 | " | " | " | 2-F, 4-Cl, 5-COO$^i$C$_3$H$_7$ | 76–78 |
| 14 | " | " | " | 2-F, 4-Cl, 5-COOCH$_2$C≡CH | 102–103 |
| 15 | " | " | " | 2-F, 4-Cl, 5-COOCH$_2$COOC$_2$H$_5$ | $n_D^{27}$ 1.5938 |
| 16 | " | " | " | 2-F, 4-Cl, 5-COOCH$_3$ | 106–107 |
| 17 | " | " | " | 2-F, 4-Cl, 5-COOH | 239–242 |
| 18 | " | " | " | 4-Cl, 5-COOH | 221–223 |
| 19 | " | " | — | 4,5-Cl$_2$ | 115–117 |
| 20 | " | " | — | 3,5-Cl$_2$ | 89–91 |
| 21 | " | " | 6,6-$(CH_3)_2$ | 3,5-Cl$_2$ | 145–147 |
| 22 | " | " | " | 5-Cl | 68–70 |
| 23 | " | " | " | 4,5-Cl$_2$ | 109–110 |
| 24 | " | " | " | 3,5-Cl$_2$, 4-OC$_2$H$_5$ | $n_D^{17.5}$ 1.6301 |
| 25 | " | " | " | 2,4-F$_2$, 5-Cl | 103–103.5 |
| 26 | " | " | " | 2,3,4,5,6-F$_5$ | 113.5–115 |

TABLE 1-continued

Structure formula:

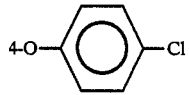

| Compound No. | X | Y | r1, r2, r3, r4 | (R)n | Physical Properties m.p. °C. |
|---|---|---|---|---|---|
| 27 | " | " | " | 2,5-F$_2$, 4-Br | 127–128 |
| 28 | " | " | " | 2,4,5-F$_3$ | 111–112 |
| 29 | " | " | " | 2,5-F$_2$, 4-Cl | 133–134 |
| 30 | " | " | — | 4-Cl | 114–115 |
| 31 | " | " | — | 4-CH$_3$ | 102–104 |
| 32 | " | " | — | 2,4-Cl$_2$ | 137–139 |
| 33 | " | " | — | 4-NO$_2$ | 178–179 |
| 34 | " | " | — | 4-Br | 138–140 |
| 35 | " | " | — | 2-Cl, 4-F | 103–104.5 |
| 36 | —S(=O)— | " | 6,6-(CH$_3$)$_2$ | 4-Cl | 115–120 |
| 37 | S | " | 6-CH$_3$ | 4-Cl | 118–122 |
| 38 | " | " | " | 4-Cl (HBr salt) | 167–170 |
| 39 | " | " | " | 2-F, 4-Cl | 78–80 |
| 40 | " | " | 6,6-(CH$_3$)$_2$ | 4-Cl | 92–94 |
| 41 | " | " | " | 4-Br | 118–120 |
| 42 | " | " | " | 4-CF$_3$ | 112–113 |
| 43 | " | " | " | 4-C$_3$H$_7$ | 56–57 |
| 44 | " | " | " | 2,4-Cl$_2$ | 80–82 |
| 45 | " | " | " | 2-Cl | 74–75 |
| 46 | " | " | " | 4-O—C$_6$H$_4$—Cl | 116–118 |
| 47 | " | " | " | 4-F | 88–90 |
| 48 | " | " | " | 2-CF$_3$, 4-Cl | 106–108 |
| 49 | " | " | 6-CH$_3$, 6-C$_2$H$_5$ | 4-Cl | 70–71 |
| 50 | " | " | 6-CH$_3$, 6-C$_3$H$_7$ | 4-Cl | 162 dec. |
| 51 | " | " | 6,6-(CH$_3$)$_2$ | 4-OCF$_3$ | 70–71 |
| 52 | " | " | " | 2-CH$_3$, 4-Cl | 82–83 |
| 53 | " | " | " | 2-F, 4-Cl | 100–102 |
| 54 | " | " | " | 2,4-F$_2$ | 110–111 |
| 55 | " | " | " | 2-OCH$_3$, 4-Cl | 137–138 |
| 56 | " | " | " | 4-COOC$_2$H$_5$ | 124–125 |
| 57 | " | " | " | 4-Cl (HBr salt) | 220–221 dec. |
| 58 | " | " | " | 4-NO$_2$ | 153.5–154.5 |
| 59 | " | " | " | 2,4,6-Cl$_3$ | 138–139 |
| 60 | " | " | " | 2-F, 4-Br | 98–99 |
| 61 | " | " | " | 4-Cl (CH$_3$—C$_6$H$_4$—SO$_3$H salt) | 178–179 |
| 62 | " | " | " | 4-Cl (CH$_3$SO$_3$H salt) | 136–138 |
| 63 | " | " | " | 4-Cl ((COOH)$_2$ salt) | 121–122 |
| 64 | " | " | " | 2-Cl, 4-F | 102–103 |
| 65 | " | " | " | 2,6-F$_2$ | 91–92 |
| 66 | " | " | " | 2,4,6-F$_3$ | 86–87 |
| 67 | " | " | " | 2,6-F$_2$, 4-Br | 103–104 |
| 68 | " | " | " | 4-CH$_3$ | 87–88 |
| 69 | " | " | " | 2-Br, 4-CH$_3$ | 130–131 |
| 70 | " | " | " | 2-Br, 4-F | 90–91 |
| 71 | " | " | " | 4-OCH$_3$ | 77–79 |
| 72 | " | " | " | 2-Br, 4-NO$_2$ | 151–153 |
| 73 | " | " | " | 2-CH$_3$, 4-Cl | 77–79 |
| 74 | " | " | " | 2,3-F$_2$, 4-Br | 156–157 |
| 75 | " | " | " | 2-F, 4-OCH$_3$ | 105–107 |
| 76 | " | " | " | 2-OCH$_3$, 4-F | $n_D^{26.5}$ 1.6069 |
| 77 | " | " | " | 2-F, 4-OCH$_2$C≡CH | $n_D^{25}$ 1.6269 |
| 78 | " | " | " | 2-F, 4-OCH$_2$—C$_6$H$_4$—Cl | 134–135 |

TABLE 1-continued

Structure formula:

$$\begin{array}{c} r^1\ r^2 \\ r^3\ r^4 \end{array} X \underset{N}{\overset{N}{\diagup}} \underset{Y}{\diagdown} = N - \text{Ar}(R)_n$$

| Compound No. | X | Y | r¹, r², r³, r⁴ | (R)n | Physical Properties m.p. °C. |
|---|---|---|---|---|---|
| 79 | " | " | " | 2-F, 4-OCH(CH₃)COOC₂H₅ | $n_D^{25}$ 1.5774 |
| 80 | " | " | " | 3-Cl, 4-F | 72–76 |
| 81 | " | —S(=O)— | " | 4-Cl | 121–124 |
| 82 | " | S | 6-CH₂-C₆H₅ | 4-Cl | 105–108 |
| 83 | " | " | 6-CH₂SCH₃ | 4-Cl | 109.5–110.5 |
| 84 | " | " | 6-iC₃H₇ | 4-Cl | 76.5–79 |
| 85 | " | " | " | 2,4-Cl₂ | 112–113 |
| 86 | " | " | 6-C₂H₅ | 4-Cl | 104–107 |
| 87 | " | " | " | 2,4-Cl₂ | 127–129 |
| 88 | " | " | " | 2,4-F₂ | 98–99 |
| 89 | " | " | " | 4-I | 103–106 |
| 90 | " | " | " | 4-Br | 104–105 |
| 91 | " | " | " | 2-F, 4-Cl | 91–92 |
| 92 | " | " | " | 2-F, 4-Br | 66–67 |
| 93 | " | " | 6-C₃H₇ | 4-Cl | 84–85 |
| 94 | " | " | 6-C₄H₉ | 4-Cl | $n_D^{31}$ 1.6425 |
| 95 | " | " | 6-C₆H₅ | 4-Cl | 124–125 |
| 96 | " | " | 6-(2,4-Cl₂-C₆H₃) | 2-Cl, 4-F | 126–129 |
| 97 | " | " | " | 4-Cl | 111–112 |
| 98 | " | " | 6-(4-CH₃-C₆H₄) | 4-Cl | 107–109 |
| 99 | " | " | 5-CH₃, 6-C₆H₅ | 4-Cl | 107–110 |
| 100 | " | " | 5-CH₃, (trans) | 2-Cl, 4-F | 78–82 |
| 101 | " | " | 6-iC₃H₇ | 4-Cl | 114–116 |
| 102 | " | " | 6,6-(CH₃)₂ | 2-F, 4-Cl, 5-N(CH₂C≡CH)₂ | 141–141.5 |
| 103 | " | " | " | 2-F, 4-Cl, 5-N(CH₂C≡CH)(COCH₂Cl) | 146.5–147.5 |
| 104 | " | " | " | 2-F, 4-Cl, 5-N(CH₃)(CH₂C≡CH) | 94–97 |

TABLE 1-continued

Structure formula $$\begin{array}{c} r^1 \\ r^2 \\ r^3 \\ r^4 \end{array} X \begin{array}{c} N \\ \\ N \end{array} Y = N - \text{Ph}(R)_n$$

| Compound No. | X | Y | r¹, r², r³, r⁴ | (R)n | Physical Properties m.p. °C. |
|---|---|---|---|---|---|
| 105 | " | " | " | 2-F, 4-Cl, 5-NH$_2$ | 141–142 |
| 106 | " | " | " | 2-F, 4-Cl, 5-NHCHCOOC$_2$H$_5$<br>  \|<br>  CH$_3$ | $n_D^{28.5}$ 1.5981 |
| 107 | " | " | " | 2-F, 4-Cl, 5-NHCH$_2$COOCH$_2$CHClCH$_2$Cl | $n_D^{25}$ 1.6031 |
| 108 | " | " | " | 2-F, 4-Cl, 5-NHCH$_2$C≡CH | 117–117.5 |
| 109 | " | " | " | 2-F, 4-Cl, 5-NHCOC$_2$H$_5$ | 170.5–174 |
| 110 | " | " | " | 2-F, 4-Cl, 5-NHCOOCH$_3$ | 111–114 |
| 111 | " | " | " | 2-F, 4-Cl, 5-NO$_2$ | 161.5–162 |
| 112 | " | " | " | 2-F, 4-Cl, 5-OC(CH$_3$)$_2$—COOCH$_3$ | 134–135 |
| 113 | " | " | " | 2-F, 4-Cl, 5-OC(CH$_3$)$_2$—COOH | 50–51 |
| 114 | " | " | " | 2-F, 4-Cl, 5-OC(CH$_3$)$_2$—COONa | 250° C. up |
| 115 | " | " | " | 2-F, 4-Cl, 5-OC$_2$H$_5$ | 104–107 |
| 116 | " | " | " | 2,4-Cl$_2$, 5-OiC$_3$H$_7$ | 125–129 |
| 117 | " | " | " | 2-F, 4-Br, 5-OiC$_3$H$_7$ | 105–107 |
| 118 | " | " | " | 2-F, 4-Cl, 5-OiC$_3$H$_7$ | $n_D^{21}$ 1.6084 |
| 119 | " | " | " | 2-F, 4-Cl, 5-OC$_3$H$_7$ | 85–87 |
| 120 | " | " | " | 2-F, 4-Cl, 5-OC$_4$H$_9$ | 58–60 |
| 121 | " | " | " | 2,4-Cl$_2$, 5-OCF$_2$HCF$_2$H | 104–106 |
| 122 | " | " | " | 2-F, 4-Cl, 5-CHC≡CH<br>  \|<br>  C$_2$H$_5$ | 82–84 |
| 123 | " | " | " | 2-F, 4-Cl, 5-CHCN<br>  \|<br>  C$_2$H$_5$ | $n_D^{27}$ 1.5975 |
| 124 | " | " | " | 2-F, 4-Cl, 5-OCHCOOC$_2$H$_5$<br>  \|<br>  C$_2$H$_5$ | $n_D^{24}$ 1.5881 |
| 125 | " | " | " | 2-F, 4-Cl, 5-OCHCOOCH$_2$C≡CH<br>  \|<br>  C$_2$H$_5$ | 80–82 |
| 126 | " | " | " | 2-F, 4-Cl, 5-OCHCOOCH$_2$CH=CH$_2$<br>  \|<br>  C$_2$H$_5$ | $n_D^{28}$ 1.5932 |
| 127 | " | " | " | 2-F, 4-Cl, 5-OCHCOOC$_2$H$_5$<br>  \|<br>  C$_3$H$_7$ | 95–96 |
| 128 | " | " | " | 2-F, 4-Cl, 5-OCHCOOC$_2$H$_5$<br>  \|<br>  CH$_2$OC$_2$H$_5$ | $n_D^{28}$ 1.5790 |
| 129 | " | O | " | 2-F, 4-Cl, 5-O$^i$C$_3$H$_7$ | $n_D^{20}$ 1.5760 |
| 130 | " | S | " | 2-F, 4-Cl, 5-OCHC=NOCH$_2$CH=CH$_2$<br>      /      \|<br>   CH$_3$   CH$_3$ | $n_D^{26.5}$ 1.6093 |

TABLE 1-continued

Structure formula:

$$\begin{array}{c} r^1\\ r^2 \end{array} \diagdown \begin{array}{c} N \\ \end{array} = N - \diagup \!\!\!\!\bigcirc\!\!\!\! - (R)_n$$
(with X, Y ring substituents)

| Compound No. | X | Y | r¹, r², r³, r⁴ | (R)n | Physical Properties m.p. °C. |
|---|---|---|---|---|---|
| 131 | " | " | " | 2-F, 4-Cl, 5-OCHC=NOH<br>                             \|    \|<br>                             CH₃  CH₃ | 151–153 |
| 132 | " | " | " | 2-F, 4-Cl, 5-OCHC₂H₅<br>                       \|<br>                      CH₃ | 55–57 |
| 133 | " | " | " | 2-F, 4-Cl, 5-OCHC≡CH<br>                      \|<br>                     CH₃ | $n_D^{28.5}$ 1.6093 |
| 134 | " | " | " | 2-F, 4-Cl, 5-OCHCH₂O—◯<br>                    \|<br>                   CH₃ | $n_D^{22}$ 1.6020 |
| 135 | " | " | " | 2-F, 4-Cl, 5-OCHCN<br>                   \|<br>                CH₃ | $n_D^{24}$ 1.6091 |
| 136 | " | " | " | 2,4-F₂, 5-OCHCN<br>                \|<br>               CH₃ | $n_D^{28}$ 1.5798 |
| 137 | " | " | " | 2,4-Cl, 5-OCHCN<br>                \|<br>               CH₃ | $n_D^{28}$ 1.6092 |
| 138 | " | " | " | 2-F, 4-Cl, 5-OCHCN<br>                   \|<br>                CH₃ | 96–99 |
| 139 | " | " | " | 2-F, 4-Cl, 5-OCHCOCH₃<br>                      \|<br>                   CH₃ | 93–94 |
| 140 | " | " | " | 2-F, 4-Cl, 5-OCHCON(CH₃)₂<br>                      \|<br>                   CH₃ | 152–154 |
| 141 | " | " | " | 2-F, 4-Cl, 5-OCHCONHC₂H₅<br>                      \|<br>                   CH₃ | 102–104 |
| 142 | " | " | " | 2-F, 4-Cl, 5-OCHCONH$^i$C₃H₇<br>                      \|<br>                   CH₃ | 110–112 |
| 143 | " | " | " | 2-F, 4-Cl, 5-OCHCONHC₄H₉<br>                      \|<br>                   CH₃ | 84–87 |
| 144 | " | " | " | 2-F, 4-Cl, 5-OCHCONHC₂H₄OC₂H₅<br>                      \|<br>                   CH₃ | $n_D^{27}$ 1.5739 |
| 145 | " | " | " | 2-F, 4-Cl, 5-OCHCONHCH₂CH=CH₂<br>                      \|<br>                   CH₃ | 117–120 |
| 146 | " | " | 6-CH₃ | 2-F, 4-Cl, 5-OCHCONHCH₃<br>                      \|<br>                   CH₃ | 158–160 |
| 147 | " | " | 6,6-(CH₃)₂ | 2-F, 4-Cl, 5-OCHCONHCH₃<br>                      \|<br>                   CH₃ | 145–146 |

TABLE 1-continued

Structure formula:

$$\begin{array}{c} r^1 \\ r^2 \\ r^3 \\ r^4 \end{array} X \begin{array}{c} N \\ \\ \\ N \end{array} Y \text{—CH=N—} \bigcirc \text{(R)}_n$$

| Compound No. | X | Y | r¹, r², r³, r⁴ | (R)n | Physical Properties m.p. °C. |
|---|---|---|---|---|---|
| 148 | " | " | " | 2-F, 4-Cl, 5-OCH(CH₃)CONHOC₂H₅ | 52–54 |
| 149 | " | " | " | 2-F, 4-Cl, 5-OCH(CH₃)CONHOCH₂CH=CH₂ | 90–93 |
| 150 | " | " | " | 2-F, 4-Cl, 5-OCH(CH₃)COO-cyclopentyl | $n_D^{23}$ 1.5912 |
| 151 | " | " | " | 2-F, 4-Cl, 5-OCH(CH₃)COO-cyclohexyl | $n_D^{22.5}$ 1.5870 |
| 152 | " | " | " | 2-F, 4-Cl, 5-OCH(CH₃)COOC(CH₃)₂—C≡CH | 84–85 |
| 153 | " | " | " | 2-F, 4-Cl, 5-OCH(CH₃)COO$^i$C₄H₉ | 103–104 |
| 154 | " | " | " | 2-F, 4-Cl, 5-OC(CH₃)₂COOC₁₀H₂₁ | $n_D^{24.5}$ 1.5545 |
| 155 | " | " | — | 2-F, 4-Cl, 5-OCH(CH₃)COOC₂H₅ | 84–86 |
| 156 | " | " | 6-CH₃ | 2-F, 4-Cl, 5-OCH(CH₃)COOC₂H₅ | 80–83 |
| 157 | " | " | 6,6-(CH₃)₂ | 2-F, 4-Br, 5-OCH(CH₃)COOC₂H₅ | $n_D^{20.5}$ 1.5998 |
| 158 | " | " | " | 2-F, 4-Cl, 5-OCH(CH₃)COOC₂H₅ | $n_D^{20}$ 1.5870 |
| 159 | " | " | " | 2,4-Cl₂, 5-OCH(CH₃)COOC₂H₅ | $n_D^{26.5}$ 1.5988 |
| 160 | " | " | " | 4-Cl, 5-OCH(CH₃)COOC₂H₅ | $n_D^{23}$ 1.5903 |
| 161 | " | " | " | 2-F, 4-Cl, 5-OCH(CH₃)COOC₄H₉ | $n_D^{17.5}$ 1.5843 |
| 162 | " | " | " | 2-F, 4-Cl, 5-OCH(CH₃)COOCH(C₂H₅)C≡CH | $n_D^{21}$ 1.5838 |
| 163 | " | " | " | 2-F, 4-Cl, 5-OCH(CH₃)COO$^i$C₃H₇ | 43–44 |

TABLE 1-continued

Structure formula:

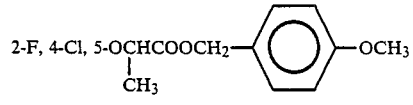

| Compound No. | X | Y | r¹, r², r³, r⁴ | (R)n | Physical Properties m.p. °C. |
|---|---|---|---|---|---|
| 164 | " | " | " | 2-F, 4-Cl, 5-OCHCOOCHC₂H₅<br>                CH₃    CH₃ | $n_D^{20.5}$ 1.5777 |
| 165 | " | " | " | 2-F, 4-Cl, 5-OCHCOOCHCOOC₂H₅<br>                CH₃    CH₃ | 124–128 |
| 166 | " | " | " | 2-F, (optical isomer) | $n_D^{27}$ 1.5670 |
| 167 | " | " | — | 2-F, 4-Cl, 5-OCHCOOCH₂C≡CH<br>                CH₃ | 111–113 |
| 168 | " | " | 6-CH₃ | 2-F, 4-Cl, 5-OCHCOOCH₂C≡CH<br>                CH₃ | 81–83 |
| 169 | " | " | 6,6-(CH₃)₂ | 2-F, 4-Cl, 5-OCHCOOCH₂C≡CH<br>                CH₃ | $n_D^{24}$ 1.5971 |
| 170 | " | " | " | 2,4-F₂, 5-OCHCOOCH₂C≡CH<br>              CH₃ | $n_D^{27.5}$ 1.5713 |
| 171 | " | " | " | 2-F, 4-Cl, 5-OCHCOOC₂H₄OC₂H₅<br>                CH₃ | $n_D^{24}$ 1.5784 |
| 172 | " | " | " | 2-F, 4-Cl, 5-OCHCOOC₂H₄OCH₂CH=CH₂<br>                CH₃ | 50–53 |
| 173 | " | " | " | 2-F, 4-Cl, 5-OCHCOOCH₂CH₂Cl<br>                CH₃ | $n_D^{26}$ 1.5941 |
| 174 | " | " | " | 2-F, 4-Cl, 5-OCHCOOCH₂CH=CH₂<br>                CH₃ | $n_D^{29}$ 1.5939 |
| 175 | " | " | " | 2-F, 4-Cl, 5-OCHCOOCH₂–⟨C₆H₄⟩–OCH₃<br>              CH₃ | $n_D^{26}$ 1.6002 |
| 176 | " | " | 6-CH₃ | 2-F, 4-Cl, 5-OCHCOOCH₃<br>              CH₃ | 90–92 |
| 177 | " | " | 6,6-(CH₃)₂ | 2-F, 4-Cl, 5-OCHCOOCH₃<br>              CH₃ | $n_D^{26}$ 1.5885 |
| 178 | " | " | — | 2-F, 4-Cl, 5-OCHCOOH<br>              CH₃ | 163–165 |
| 179 | " | " | 6-CH₃ | 2-F, 4-Cl, 5-OCHCOOH<br>              CH₃ | 121–123 |
| 180 | " | " | 6,6-(CH₃)₂ | 2-F, 4-Cl, 5-OCHCOOH<br>              CH₃ | 203–205 |
| 181 | " | " | " | 2-F, 4-Cl, 5-OCHCOONa<br>              CH₃ | 164–170 |

TABLE 1-continued

Structure formula:

$$\begin{array}{c} r^1 \\ r^2 \\ r^3 \\ r^4 \end{array} X \underset{N}{\overset{N}{\rightleftarrows}} \underset{Y}{\overset{N}{=}} N \text{—} \langle \text{Ph} \rangle \text{(R)n}$$

| Compound No. | X | Y | $r^1, r^2, r^3, r^4$ | (R)n | Physical Properties m.p. °C. |
|---|---|---|---|---|---|
| 182 | " | " | " | 2-F, 4-Cl, 5-OCHCO—Ph, CH₃ | 44–46 |
| 183 | " | " | " | 2-F, 4-Cl, 5-OCHCOSC₂H₅, CH₃ | $n_D^{26.5}$ 1.6065 |
| 184 | " | " | " | 2-F, 4-Cl, 5-CH—C=NOH, CH₃, Ph | 73–75 |
| 185 | " | " | " | 2-F, 4-Cl, 5-OCH—Ph, CH₃ | 95–97 |
| 186 | " | " | 6-CH₃ | 2-F, 4-Cl, 5-OCH(COOC₂H₅)₂ | $n_D^{29}$ 1.5830 |
| 187 | " | " | 6,6-(CH₃)₂ | 2-F, 4-Cl, OCH(COOC₂H₅)₂ | $n_D^{27.5}$ 1.5820 |
| 188 | " | " | " | 2-F, 4-Cl, 5-OCHCOOC₂H₅, S-Ph | $n_D^{22}$ 1.6248 |
| 189 | " | " | " | 2-F, 4-Cl, 5-OCH₂-(2-pyridyl) | 124–126 |
| 190 | " | " | 6,6-(CH₃)₂ | 2-F, 4-Cl, 5-OCH₂C=NOCH₂CH=CH₂, CH₃ | $n_D^{26.5}$ 1.5950 |
| 191 | " | " | " | 2-F, 4-Cl, 5-OCH₂C=NOH, CH₃ | 152–156 |
| 192 | " | " | " | 2-F, 4-Cl, 5-OCH₂C≡C—CH₃ | 98–99 |
| 193 | " | " | " | 2-F, 4-Cl, 5-OCH₂C≡C.Cl | 96–97 |
| 194 | " | " | — | 2-F, 4-Cl, 5-OCH₂C≡CH | 116–117 |
| 195 | " | " | 6-CH₃ | 2-F, 4-Cl, 5-OCH₂C≡CH | 117–118 |
| 196 | " | " | 6,6-(CH₃)₂ | 2-F, 4-Br, 5-OCH₂C≡CH | 114–115 |
| 197 | " | " | " | 2-F, 4-Cl, 5-OCH₂C≡CH | 103–106 |
| 198 | " | " | " | 2-F, 4,5-(OCH₂C≡CH)₂ | 104–105 |
| 199 | " | " | " | 2,4-F₂, 5-OCH₂C≡CH | 99–100 |
| 200 | " | " | " | 2,4-F, 5-OCH₂C≡CH, 6-Cl | 106–108 |
| 201 | " | " | " | 2,6-F, 4-Cl, 5-OCH₂C≡CH | $n_D^{28}$ 1.6040 |
| 202 | " | " | " | 2-f, 4-OCH₃, 5-OCH₂C≡CH | 124–126 |
| 203 | " | " | " | 2-F, 4-OCH₂—⟨Ph⟩—Cl, 5-OCH₂C≡CH | $n_D^{30}$ 1.6310 |
| 204 | " | " | " | 4-Cl, 5-OCH₂C≡CH | $n_D^{23}$ 1.6388 |
| 205 | " | " | 6-C₂H₅ | 2-F, 4-Cl, 5-OCH₂C≡CH | 126–128 |
| 206 | " | O | 6,6-(CH₃)₂ | 2-F, 4-Cl, 5-OCH₂CCl₂CHCl₂ | 155–157 |
| 207 | " | S | " | 2-F, 4-Cl, 5-OCH₂CCl=CH₂ | 126–128 |
| 208 | " | " | " | 2-F, 4-Cl, 5-OCH₂CF₃ | 91–92 |
| 209 | " | " | " | 2-F, 4-Cl, 5-OCH₂CH₂OCH=CH₂ | 96–98 |

TABLE 1-continued

Structure formula

| Compound No. | X | Y | r¹, r², r³, r⁴ | (R)n | Physical Properties m.p. °C. |
|---|---|---|---|---|---|
| 210 | " | " | " | 2-F, 4-Cl, 5-OC$_3$H$_6$CN | 91–93 |
| 211 | " | " | " | 2-F, 4-Cl, 5-OC$_3$H$_6$COCH$_3$ | $n_D^{27}$ 1.5841 |
| 212 | " | " | " | 2-F, 4-Cl, 5-OC$_3$H$_6$COOC$_2$H$_5$ | $n_D^{24}$ 1.5929 |
| 213 | " | " | " | 2-F, 4-Cl, 5-OC$_2$H$_4$OC$_2$H$_4$OCH$_3$ | $n_D^{23}$ 1.5880 |
| 214 | " | " | " | 2-F, 4-Cl, 5-OC$_2$H$_4$OCH$_3$ | $n_D^{21.5}$ 1.6109 |
| 215 | " | " | " | 2-F, 4-Cl, 5-OC$_2$H$_4$OCOCH$_3$ | 81–82 |
| 216 | " | " | " | 2-F, 4-Cl, 5-OC$_2$H$_4$O—⟨Ph⟩ | 125–127 |
| 217 | " | " | " | 2-Br, 4-Cl, 5-OC$_2$H$_4$O—⟨Ph⟩ | 132–133 |
| 218 | " | " | " | 4-Cl, 5-OC$_2$H$_4$O—⟨Ph⟩ | 137–139 |
| 219 | " | " | " | 2-F, 4-Cl, 5-OC$_2$H$_4$—O—⟨Ph⟩—CH$_3$ | 137–138 |
| 220 | " | " | " | 2-F, 4-Cl, 5-OC$_2$H$_4$SCH$_3$ | 119–121 |
| 221 | " | " | " | 2-F, 4-Cl, 5-OC$_2$H$_4$SO$_2$CH$_3$ | 151–154 |
| 222 | " | " | " | 2-F, 4-Cl, 5-OC$_2$H$_4$SOCH$_3$ | $n_D^{26}$ 1.6141 |
| 223 | " | " | " | 2-F, 4-Cl, 5-OCH$_2$CH=CCl$_2$ | 99–102 |
| 224 | " | " | " | 2-F, 4-Cl, 5-OCH$_2$CH=CH$_2$ | 72–73 |
| 225 | " | " | " | 2-F, 4-Br, 5-OCH$_2$CH=CH$_2$ | $n_D^{22.5}$ 1.6391 |
| 226 | " | " | " | 2,4-F$_2$, 5-OCH$_2$CH=CH$_2$ | 50–53 |
| 227 | " | " | " | 2-F, 4-Cl, 5-OCH$_2$CH=CHCH$_3$ | 65–67 |
| 228 | " | " | " | 2-F, 4-Cl, 5-OCH$_2$CH=CHCOOC$_2$H$_5$ | $n_D^{24}$ 1.5991 |
| 229 | " | " | " | 2-F, 4-Cl, 5-OCH$_2$CH=CHCl | 108–109 |
| 230 | " | " | " | 2-F, 4-Br, 5-OCH$_2$CN | $n_D^{33}$ 1.6257 |
| 231 | " | " | " | 2-F, 4-Cl, 5-OCH$_2$CN | 89–90 |
| 232 | " | " | " | 2-F, 4-Cl, 5-OCH$_2$COCH$_3$ | 107–108 |
| 233 | " | " | " | 2-F, 4-Cl, 5-OCH$_2$COO—⟨cyclopentyl⟩ | 133–116 |
| 234 | " | " | " | 2-F, 4-Br, 5-OCH$_2$COOC$_2$H$_5$ | 105–106 |
| 235 | " | " | " | 2-F, 4-Cl, 5-OCH$_2$COOCH$_2$CHClCH$_2$Cl | $n_D^{26}$ 1.5979 |
| 236 | " | " | " | 2-F, 4-Cl, 5-OCH$_2$—⟨cyclopropyl⟩ | 86–89 |
| 237 | " | " | " | 2-F, 4-Cl, 5-OCH$_2$OC$_2$H$_5$ | 54–55 |
| 238 | " | " | " | 2-F, 4-Cl, 5-OCH$_2$OCH$_3$ | 143.5–144 |
| 239 | " | " | " | 2-F, 4-Cl, 5-OCH$_2$—⟨Ph⟩ | 107–109 |

TABLE 1-continued

Structure formula

| Compound No. | X | Y | r¹, r², r³, r⁴ | (R)n | Physical Properties m.p. °C. |
|---|---|---|---|---|---|
| 240 | " | " | " | 2-F, 4,5-(OCH₂—⟨⟩—Cl)₂ | 130–131.5 |
| 241 | " | " | " | 2-F, 4-Cl, 5-OCH₂SCH₃ | 110–114 |
| 242 | " | " | " | 2-F, 4-Cl, 5-OCH₂SO₂CH₃ | 48–51 |
| 243 | " | " | " | 2-F, 4-Cl, 5-OCH₂SOCH₃ | 122–124 |
| 244 | " | " | " | 2-F, 4-Cl, 5-OCH₂S—⟨⟩ | $n_D^{28}$ 1.6514 |
| 245 | " | " | " | 2-F, 4-Cl, 5-OCH₂Si(CH₃)₃ | $n_D^{22}$ 1.5871 |
| 246 | " | " | " | 2,4-Cl₂, 5-OCH₃ | 129–130 |
| 247 | " | " | " | 2-F, 4-Cl, 5-OCH₃ | 131–132 |
| 248 | " | " | " | 2-F, 4-Br, 5-OCH₃ | 119–121 |
| 249 | " | " | " | 2-F, 4,5-(OCH₃)₂ | 178–179.5 |
| 250 | " | " | " | 2,4-Cl₂, 5-OCH₂C≡CH | 124.5–125 |
| 251 | " | " | " | 2-F, 4-Cl, 5-OC(CH₃)₂COOC₂H₅ | $n_D^{24}$ 1.5835 |
| 252 | " | " | " | 2-F, 4-Cl, 5-OCOCH₃ | 130–131 |
| 253 | " | " | " | 2-F, 4-Cl, 5-OCON(CH₃)₂ | 140–142 |
| 254 | " | " | " | 2-F, 4-Cl, 5-OCONHC₂H₅ | 136–138 |
| 255 | " | " | " | 2-F, 4-Cl, 5-OH | 207–208 |
| 256 | " | " | " | 2-F, 4-Cl, 5-OP(S)(OC₂H₅)₂ | $n_D^{28}$ 1.5878 |
| 257 | " | " | " | 2-F, 4-Cl, 5-OP(S)(OCH₃)₂ | 105–108 |
| 258 | " | " | " | 2-F, 4-Cl, 5-O—⟨⟩—NO₂ | 158–161 |
| 259 | " | " | " | 2-F, 4-Cl, 5-OSO₂CH₃ | 130–131 |
| 260 | O | " | 6-CH₃ | 2-F, 4-Cl, 5-OCH(CH₃)—S—⟨⟩ | 130–132 |
| 261 | " | " | " | 2-F, 4-Cl, 5-CH₂OCOCH₃ | 72–73 |
| 262 | " | " | " | 2-F, 4-Cl, 5-CH=CHCOOC₂H₅ | 115–116.5 |
| 263 | " | " | " | 2-F, 4-CL, 5-CH=NOC₂H₅ | 99–102 |
| 264 | " | " | " | 2-F, 4-Cl, 5-CH=NOCH₂COOC₂H₅ | $n_D^{21.5}$ 1.5720 |
| 265 | " | " | " | 2-F, 4-Cl, 5-CON(CH₃)₂ | 170–171 |
| 266 | " | " | " | 2-F, 4-Cl, 5-CONHC₂H₅ | 161–162 |
| 267 | " | " | " | 2-F, 4-Cl, 5-CONH$^i$C₃H₇ | |
| 268 | " | " | " | 2-F, 4-Cl, 5-CONHCH₂C≡CH | 163–165 |
| 269 | " | " | " | 2-F, 4-Cl, 5-CONHOC₂H₅ | 142–143.5 |
| 270 | " | " | " | 2-F, 4-Cl, 5-COOC₂H₅ | 123–124 |
| 271 | " | " | " | 4-Cl, 5-COOC₂H₅ | $n_D^{23}$ 1.6006 |
| 272 | " | " | " | 2-F, 4-Cl, 5-COO$^i$C₃H₇ | 68–71 |
| 273 | " | " | " | 2-F, 4-Cl, 5-COOCH(CH₃)CH=CHCOO$^i$C₃H₇ | 127.5–129 |

TABLE 1-continued

Structure formula:

$$\begin{array}{c} r^1 \\ r^2 \\ r^3 \\ r^4 \end{array} X \begin{array}{c} N \\ \diagup \\ \diagdown \\ N \end{array} Y = N - \text{Ph}(R)_n$$

| Compound No. | X | Y | r¹, r², r³, r⁴ | (R)n | Physical Properties m.p. °C. |
|---|---|---|---|---|---|
| 274 | " | " | " | 2-F, 4-Cl, 5-COOCHCH=CHCOOCH₃ <br>                        \|<br>                       CH₃ | 89–91 |
| 275 | " | " | " | 2-F, 4-Cl, 5-COOCHCOOC₂H₅ <br>                      \|<br>                     CH₃ | 112–114 |
| 276 | " | " | " | 2-F, 4-Cl, 5-COOCH₂C≡CH | 132–133.5 |
| 277 | " | " | " | 2-F, 4-Cl, 5-COOCH₂CHC₄H₉ <br>                       \|<br>                      C₂H₅ | $n_D^{24}$ 1.5653 |
| 278 | " | " | " | 2-F, 4-Cl, 5-COOC₂H₄OCH₃ | 93.5–94.5 |
| 279 | " | " | " | 2-F, 4-Cl, 5-COOC₂H₄O−Ph | 99–102 |
| 280 | " | " | " | 2-F, 4-Cl, 5-COOCH₂COOC₂H₅ | $n_D^{26.5}$ 1.5739 |
| 281 | " | " | " | 2-F, 4-Cl, 5-COOCH₂S−Ph | 109–111.5 |
| 282 | " | " | " | 2-F, 4-Cl, 5-COOCH₃ | 117–119 |
| 283 | " | " | " | 2-F, 4-Cl, 5-COOH | 227–230 |
| 284 | " | " | " | 4-Cl, 5-COOH | 206 dec. |
| 285 | " | " | " | 4-Cl | 93–96 |
| 286 | " | " | " | 2-F, 4-Cl | 65–67 |
| 287 | " | " | " | 2-F, 4-OCH₃ | 72–73.5 |
| 288 | " | " | " | 2-OCH₃, 4-F | 94–96 |
| 289 | " | " | " | 2-F, 4-OCH₂C≡CH | $n_D^{24}$ 1.6070 |
| 290 | " | " | " | 2-F, 4-OCH₂−Ph−Cl | 129–130 |
| 291 | " | " | " | 2-F, 4-OCHCOOC₂H₅ <br>               \|<br>              CH₃ | $n_D^{25}$ 1.5642 |
| 292 | " | " | " | 4-CH₂CH₂−Ph−CH₃ | 124–125 |
| 293 | " | " | " | 4-O−Ph−OCHCOOC₂H₅ <br>                         \|<br>                        CH₃ | 94–96 |
| 294 | " | " | " | 2-COOC₂H₅, 4-O−Ph(Cl)(CF₃) | 47–50 |
| 295 | " | " | 5,6-(CH₃)₂ (cis) | 4-Cl | 130–132 |
| 296 | " | " | 5,6-(CH₃)₂ (trans) | 4-Cl | 89–90 |
| 297 | " | " | 6-C₂H₅ | 4-Cl | 105–115 |

TABLE 1-continued

Structure formula:

$$\begin{array}{c} r^1 \\ r^2 \\ r^3 \\ r^4 \end{array} X \begin{array}{c} N \\ \\ N \end{array} = N - \text{(R)}_n$$

| Compound No. | X | Y | r¹, r², r³, r⁴ | (R)n | Physical Properties m.p. °C. |
|---|---|---|---|---|---|
| 298 | " | " | " | 2-F, 4-Cl | $n_D^{23}$ 1.5819 |
| 299 | " | " | " | 2-F, 4-Br | 49–50 |
| 300 | " | " | " | 2,4,6-F₃ | 93–94 |
| 301 | " | " | 6-C₃H₇ | 4-Cl | 107–111 |
| 302 | " | " | 6-CH₃ | 2-F, 4-Cl, 5-N(CH₂C≡CH)—COCH₂Cl | 143–144 |
| 303 | " | " | " | 2-F, 4-Cl, 5-NH₂ | $n_D^{26}$ 1.6347 |
| 304 | " | " | " | 2-F, 4-Cl, 5-NHCH₂C≡CH | 46–49 |
| 305 | " | " | " | 2-F, 4-Cl, 5-NHCOCF₃ | 153–156 |
| 306 | " | " | " | 2-F, 4-Cl, 5-NO₂ | 108–110 |
| 307 | " | " | " | 2-F, 4-Cl, 5-OC₃H₆C(CH₃)=NOH | $n_D^{27.5}$ 1.5870 |
| 308 | " | " | " | 2-F, 4-Cl, 5-O-(7-chloroquinoxalin-2-yl) | 146–147 |
| 309 | " | " | " | 2-F, 4-Cl, 5-OC(CH₃)₂CONHCH₃ | 147–148 |
| 310 | " | " | 6,6-(CH₃)₂ | 2-F, 4-Cl, 5-OC(CH₃)₂COOH | 62–65 |
| 311 | " | " | 6-CH₃ | 2-F, 4-Cl, 5-OCH(CH₃)CON(C₆H₁₁)CONH(C₆H₁₁) | 68–71 |
| 312 | " | " | " | 2-F, 4-Cl, 5-OC₁₂H₂₅ | $n_D^{26.5}$ 1.5442 |
| 313 | " | " | " | 2-F, 4-Cl, 5-O$^i$C₃H₇ | $n_D^{28}$ 1.5872 |
| 314 | " | " | " | 2-F, 4-Cl, 5-OC₃H₇ | $n_D^{22.5}$ 1.5891 |
| 315 | " | " | " | 2-F, 4-Cl, 5-OC₄H₉ | $n_D^{23}$ 1.5942 |
| 316 | " | " | " | 2-F, 4-Cl, 5-OCH(C₂H₅)C≡CH | $n_D^{22}$ 1.6010 |
| 317 | " | " | " | 2-F, 4-Cl, 5-OCH(C₂H₅)CN | $n_D^{27}$ 1.5740 |
| 318 | " | " | " | 2-F, 4-Br, 5-OCH(C₂H₅)CN | $n_D^{27}$ 1.5680 |
| 319 | " | " | " | 2-F, 4-Cl, 5-OCH(C₂H₅)COOC₂H₅ | $n_D^{24.5}$ 1.5610 |
| 320 | " | " | " | 2-F, 4-Cl, 5-OCH(C₂H₅)COOCH₂C≡CH | 71–73 |

TABLE 1-continued

Structure formula:

$$\begin{array}{c} r^1 \\ r^2 \\ r^3 \\ r^4 \end{array} X \overset{N}{\underset{Y}{\rightleftharpoons}} N = N \text{—} \langle \text{(R)n} \rangle$$

| Compound No. | X | Y | r¹, r², r³, r⁴ | (R)n | Physical Properties m.p. °C. |
|---|---|---|---|---|---|
| 321 | " | " | 6-C₂H₅ | 2-F, 4-Cl, 5-OCH(C₂H₅)COOCH₂C≡CH | 68–70 |
| 322 | " | " | 6-CH₃ | 2-F, 4-Cl, 5-OCH(C₂H₅)COOCH₂CH=CH₂ | $n_D^{28}$ 1.5770 |
| 323 | " | " | 6-C₂H₅ | 2-F, 4-Cl, 5-OCH(C₂H₅)COOCH₂CH=CH₂ | $n_D^{28}$ 1.5792 |
| 324 | " | " | 6-CH₃ | 2-F, 4-Cl, 5-OCH(C₃H₅)CN | $n_D^{20}$ 1.5605 |
| 325 | " | " | 6-C₂H₅ | 2-F, 4-Cl, 5-OCH(C₃H₇)COOC₂H₅ | $n_D^{21}$ 1.5560 |
| 326 | " | " | 6-CH₃ | 2-F, 4-Cl, 5-OCH(CH₂OC₂H₅)COOC₂H₅ | $n_D^{28}$ 1.5580 |
| 327 | " | " | 6-C₂H₅ | 2-F, 4-Cl, 5-OCH(CH₂OC₂H₅)COOC₂H₅ | $n_D^{28}$ 1.5591 |
| 328 | " | " | 6-CH₃ | 2-F, 4-Cl, 5-OCH(CH₃)-(3-methyl-isoxazol-5-yl) | 110–112 |
| 329 | " | " | " | 2-F, 4-Cl, 5-OCH(CH₃)-C(CH₃)=N-O- (oxazoline) | $n_D^{20}$ 1.5583 |
| 330 | " | " | " | 2-F, 4-Cl, 5-OCH(CH₃)-(5-methyl-isoxazol-3-yl) | $n_D^{15}$ 1.5764 |
| 331 | " | " | " | 2-F, 4-Cl, 5-OCH(CH₃)—C(CH₃)=NOCH₂CH=CH₂ | $n_D^{26.5}$ 1.5601 |
| 332 | " | " | " | 2-F, 4-Cl, 5-OCH(CH₃)—C(CH₃)=NOH | 71–73 |
| 333 | " | " | " | 2-F, 4-Cl, 5-OCH(CH₃)C₂H₅ | $n_D^{22.5}$ 1.5860 |
| 334 | " | " | " | 2-F, 4-Cl, 5-OCH(CH₃)C≡CH | $n_D^{28.5}$ 1.5921 |
| 335 | " | " | " | 2-F, 4-Cl, 5-OCH(CH₃)CH₂O—C₆H₅ | $n_D^{22}$ 1.5878 |
| 336 | " | " | " | 2-F, 4-Cl, 5-OCH(CH₃)CH=CHCOOC₂H₅ | $n_D^{23}$ 1.5783 |

TABLE 1-continued

Structure formula $$\begin{array}{c} r^1 \\ r^2 \\ r^3 \\ r^4 \end{array} X \begin{array}{c} N = \\ N - Y \end{array} = N - \bigcirc (R)_n$$

| Compound No. | X | Y | r¹, r², r³, r⁴ | (R)n | Physical Properties m.p. °C. |
|---|---|---|---|---|---|
| 337 | " | " | " | 2-F, 4-Cl, 5-CHCN<br>                 \|<br>                 CH₃ | $n_D^{28}$ 1.5688 |
| 338 | " | " | " | 2,4-F₂, 5-CHCN<br>                \|<br>                CH₃ | $n_D^{28}$ 1.5619 |
| 339 | " | " | " | 2-F, 4-Br, 5-CHCN<br>                  \|<br>                 CH₃ | $n_D^{27}$ 1.5886 |
| 340 | " | " | " | 2,4-Cl₂, 5-CHCN<br>                 \|<br>                CH₃ | $n_D^{28}$ 1.5971 |
| 341 | " | " | " | 2,4-Cl₂, 5-OCHCON⟨morpholine⟩<br>                 \|<br>                CH₃ | 158–160 |
| 342 | " | " | " | 2-F, 4-Cl, 5-OCHCOCH₃<br>                  \|<br>                 CH₃ | $n_D^{24.5}$ 1.5663 |
| 343 | " | " | " | 2-F, 4-Cl, 5-O—CHCONH₂<br>                   \|<br>                  CH₃ | 56–60 |
| 344 | " | " | " | 2-F, 4-Cl, 5-O—CHCONHC₂H₅<br>                   \|<br>                  CH₃ | 149–153 |
| 345 | " | " | 6-C₂H₅ | 2-F, 4-Cl, 5-O—CHCONHC₄H₉<br>                   \|<br>                  CH₃ | $n_D^{17.5}$ 1.5698 |
| 346 | " | " | 6-CH₃ | 2-F, 4-Cl, 5-O—CHCONHCCOOCH₃<br>                  \|        \|<br>                  CH₃  CH₃ | $n_D^{27}$ 1.5608 |
| 347 | " | " | " | 2-F, 4-Cl, 5-OCHCONHCH₂C≡CH<br>                 \|<br>                CH₃ | 134–137 |
| 348 | " | " | " | 2-F, 4-Cl, 5-OCHCONHCH₂CH=CH₂<br>                 \|<br>                CH₃ | 109–113 |
| 349 | " | " | " | 2-F, 4-Cl, 5-OCHCONHCH₂COOC₂H₅<br>                 \|<br>                CH₃ | 118–121 |
| 350 | " | " | " | 2-F, 4-Cl, 5-OCHCONHCH₂—⟨phenyl⟩<br>                 \|<br>                CH₃ | 50–53 |
| 351 | " | " | " | 2-F, 4-Cl, 5-OCHCONHOC₂H₅<br>                 \|<br>                CH₃ | 135–138 |
| 352 | " | " | " | 2-F, 4-Cl, 5-OCHCONH—⟨phenyl⟩<br>                 \|<br>                CH₃ | 155–158 |

TABLE 1-continued

Structure formula $$\begin{array}{c}r^1\\r^2\\r^3\\r^4\end{array}\diagdown\!\!\!-\!\!\!\text{N}\!\!=\!\!\text{N}\!-\!\!\!\diagdown\!\!\!\!\text{(R)}n$$

with X, Y and ring system as shown.

| Compound No. | X | Y | r¹, r², r³, r⁴ | (R)n | Physical Properties m.p. °C. |
|---|---|---|---|---|---|
| 353 | " | " | " | 2-F, 4-Cl, 5-OCHCOO—⬠H, with CH₃ on OCH | 58–59 |
| 354 | " | " | " | 2-F, 4-Cl, 5-OCHCOO—⬡H, with CH₃ on OCH | $n_D^{22}$ 1.5669 |
| 355 | " | " | " | 2-F, 4-Cl, 5-OCHCOOC(CH₃)₂—C≡CH, with CH₃ on OCH | 116–117 |
| 356 | " | " | " | 2-F, 5-Cl, 5-OCHCOO$^t$C₄H₉, with CH₃ on OCH | 108–108.5 |
| 357 | " | " | 6-C₂H₅ | 2-F, 4-Cl, 5-OOCHCOO$^t$C₄H₉, with CH₃ on OCH | 92–93 |
| 358 | " | " | 6-CH₃ | 2-F, 4-Cl, 5-OCHCOOC₁₀H₂₁, with CH₃ on OCH | $n_D^{20.5}$ 1.5456 |
| 359 | " | " | " | 2-F, 4-Cl, 5-OCHCOOC₂H₅, with CH₃ on OCH | $n_D^{26}$ 1.5870 |
| 360 | " | " | " | 2-F, 4-Br, 5-OCHCOOC₂H₅, with CH₃ on OCH | $n_D^{27}$ 1.5696 |
| 361 | " | " | " | 2,4-Cl₂, 5-OCHCOOC₂H₅, with CH₃ on OCH | 147–149 |
| 362 | " | " | " | 4-Cl, 5-OCHCOOC₂H₅, with CH₃ on OCH | $n_D^{23}$ 1.5901 |
| 363 | " | " | 6,6-(CH₃)₂ | 2-F, 4-Cl, 5-OCHCOOC₂H₅, with CH₃ on OCH | $n_D^{26}$ 1.5675 |
| 364 | " | " | 6-C₂H₅ | 2-F, 4-Br, 5-OCHCOOC₂H₅, with CH₃ on OCH | $n_D^{20.5}$ 1.5682 |
| 365 | " | " | " | 2-F, 4-Cl, 5-OCHCOOC₂H₅, with CH₃ on OCH | $n_D^{21.5}$ 1.5492 |
| 366 | " | " | 6-C₃H₇ | 2-F, 4-Cl, 5-OCHCOOC₂H₅, with CH₃ on OCH | $n_D^{24}$ 1.5572 |
| 367 | " | " | 6-CH₃ | 2-F, 4-Cl, 5-OCHCOOC₃H₇, with CH₃ on OCH | $n_D^{28}$ 1.5569 |
| 368 | " | " | 6-C₂H₅ | 2-F, 4-Cl, 5-OCHCOOC₄H₉, with CH₃ on OCH | $n_D^{21.5}$ 1.5399 |
| 369 | " | " | 6-CH₃ | 2-F, 4-Cl, 5-OCHCOOCHC≡CH, with CH₃ and C₂H₅ on OCH | 77–78 |

TABLE 1-continued

Structure formula

| Compound No. | X | Y | r¹, r², r³, r⁴ | (R)n | Physical Properties m.p. °C. |
|---|---|---|---|---|---|
| 370 | " | " | " | 2-F, 4-Cl, 5-OCHCOOⁱC₃H₇<br>$\quad\quad\quad\quad\quad$ CH₃ | $n_D^{20.5}$ 1.5680 |
| 371 | " | " | 6-C₂H₅ | 2-F, 4-Cl, 5-OCHCOOⁱC₃H₇<br>$\quad\quad\quad\quad\quad$ CH₃ | $n_D^{25}$ 1.5620 |
| 372 | " | " | 6-CH₃ | 2-F, 4-Cl, 5-OCHCOOCHC₂H₅<br>$\quad\quad\quad\quad\quad$ CH₃ $\quad$ CH₃ | $n_D^{20.5}$ 1.5635 |
| 373 | " | " | " | 2-F, 4-Cl, 5-OCHCOOCHCN<br>$\quad\quad\quad\quad\quad$ CH₃ $\quad$ CH₃ | $n_D^{24}$ 1.5579 |
| 374 | " | " | " | 2-F, 4-Cl, 5-OCHCOOCHCOOC₂H₅<br>$\quad\quad\quad\quad\quad$ CH₃ $\quad$ CH₃ | $n_D^{26}$ 1.5554 |
| 375 | " | " | " | 2-F, 4-Cl, 5-OCHCOOCHCOOC₂H₅(isomer)<br>$\quad\quad\quad\quad\quad$ CH₃ $\quad$ CH₃ | 98–100 |
| 376 | " | " | " | 2-F, 4-Cl, 5-OCHCOOCHS—⟨phenyl⟩<br>$\quad\quad\quad\quad\quad$ CH₃ $\quad$ CH₃ | $n_D^{19}$ 1.5960 |
| 377 | " | " | " | 2-F, 4-Cl, 5-OCHCOOCH₂—⟨furan⟩<br>$\quad\quad\quad\quad\quad$ CH₃ | 75–77 |
| 378 | " | " | " | 2-F, 4-Cl, 5-OCHCOOCH₂—⟨isoxazole-CH₃⟩<br>$\quad\quad\quad\quad\quad$ CH₃ | $n_D^{21.5}$ 1.5751 |
| 379 | " | " | " | 2-F, 4-Cl, 5-OCHCOOCH₂C≡CH<br>$\quad\quad\quad\quad\quad$ CH₃ | 101–102 |
| 380 | " | " | " | 2,4-F₂, 5-OCHCOOCH₂C≡CH<br>$\quad\quad\quad\quad\quad$ CH₃ | $n_D^{27.5}$ 1.5540 |
| 381 | " | " | 6,6-(CH₃)₂ | 2-F, 4-Cl, 5-OCHCOOCH₂C≡CH<br>$\quad\quad\quad\quad\quad$ CH₃ | $n_D^{26}$ 1.5850 |
| 382 | " | " | 6-CH₂OCH₃ | 2-F, 4-Cl, 5-OCHCOOCH₂C≡CH<br>$\quad\quad\quad\quad\quad$ CH₃ | $n_D^{27}$ 1.5809 |
| 383 | " | " | 6-C₂H₅ | 2-F, 4-Cl, 5-OCHCOOCH₂C≡CH<br>$\quad\quad\quad\quad\quad$ CH₃ | $n_D^{26}$ 1.5785 |
| 384 | " | " | 6-C₃H₇ | 2-F, 4-Cl, 5-OCHCOOCH₂C≡CH<br>$\quad\quad\quad\quad\quad$ CH₃ | $n_D^{24}$ 1.5652 |
| 385 | " | " | 5-C₂H₅ | 2-F, 4-Cl, 5-OCHCOOCH₂C≡CH<br>$\quad\quad\quad\quad\quad$ CH₃ | $n_D^{27}$ 1.5775 |

TABLE 1-continued

Structure formula

| Compound No. | X | Y | $r^1, r^2, r^3, r^4$ | (R)n | Physical Properties m.p. °C. |
|---|---|---|---|---|---|
| 386 | " | " | 6-CH$_3$ | 2-F, 4-Cl, 5-OCHCOOC$_2$H$_4$OCH$_2$CH=CH$_2$<br>   \|<br>   CH$_3$ | $n_D^{21}$ 1.5648 |
| 387 | " | " | " | 2-F, 4-Cl, 5-OCHCOOCH$_2$CH$_2$Cl<br>   \|<br>   CH$_3$ | $n_D^{26.5}$ 1.5778 |
| 388 | " | " | " | 2-F, 4-Cl, 5-OCHCOOC$_2$H$_4$OC$_2$H$_5$<br>   \|<br>   CH$_3$ | $n_D^{24}$ 1.5634 |
| 389 | " | " | " | 2-F, 4-Cl, 5-O—CHCOOC$_2$H$_4$OCH$_3$<br>   \|<br>   CH$_3$ | $n_D^{24}$ 1.5613 |
| 390 | " | " | " | 2-F, 4-Cl, 5-OCHCOOC$_2$H$_4$SCH$_2$COOCH$_3$<br>   \|<br>   CH$_3$ | $n_D^{19}$ 1.5701 |
| 391 | " | " | " | 2-F, 4-Cl, 5-OCHCOOC$_2$H$_4$SCH$_2$—C$_6$H$_5$<br>   \|<br>   CH$_3$ | $n_D^{24}$ 1.5613 |
| 392 | " | " | " | 2-F, 4-Cl, 5-OCHCOOCH$_2$CH=CH$_2$<br>   \|<br>   CH$_3$ | $n_D^{30.5}$ 1.5841 |
| 393 | " | " | 6-C$_2$H$_5$ | 2-F, 4-Cl, 5-OCHCOOCH$_2$CHBrCH$_2$Br<br>   \|<br>   CH$_3$ | $n_D^{28}$ 1.5820 |
| 394 | " | " | 6-CH$_3$ | 2-F, 4-Cl, 5-OCHCOOCH$_2$COOC$_2$H$_5$<br>   \|<br>   CH$_3$ | 113–115 |
| 395 | " | " | " | 2-F, 4-Cl, 5-OCHCOOCH$_2$—C$_6$H$_5$<br>   \|<br>   CH$_3$ | 104–106 |
| 396 | " | " | " | 2-F, 4-Cl, 5-OCHCOOCH$_2$—C$_6$H$_4$—OCH$_3$<br>   \|<br>   CH$_3$ | $n_D^{26}$ 1.5683 |
| 397 | " | " | 6-C$_2$H$_5$ | 2-F, 4-Cl, 5-OCHCOOCH$_2$—C$_6$H$_4$—OCH$_3$<br>   \|<br>   CH$_3$ | $n_D^{26}$ 1.5883 |
| 398 | " | " | 6-CH$_3$ | 2-F, 4-Cl, 5-OCHCOOCH$_2$SCH$_2$CH=CH$_2$<br>   \|<br>   CH$_3$ | $n_D^{22}$ 1.5884 |
| 399 | " | " | " | 2-F, 4-Cl, 5-OCHCOOCH$_2$SCH$_2$COOCH$_3$<br>   \|<br>   CH$_3$ | $n_D^{24}$ 1.5773 |
| 400 | " | " | " | 2-F, 4-Cl, 5-OCHCOOCH$_2$SCH$_3$<br>   \|<br>   CH$_3$ | $n_D^{22}$ 1.5864 |

TABLE 1-continued

Structure formula:

$$\begin{array}{c} r^1 \\ r^2 \\ r^3 \\ r^4 \end{array} \diagdown X \diagdown N \diagdown Y = N - \phenyl(R)_n$$

| Compound No. | X | Y | r¹, r², r³, r⁴ | (R)n | Physical Properties m.p. °C. |
|---|---|---|---|---|---|
| 401 | " | " | " | 2-F, 4-Cl, 5-OCHCOOCH₂S—⌬<br>　　　　　　　｜<br>　　　　　　　CH₃ | $n_D^{22}$ 1.6042 |
| 402 | " | " | " | 2-F, 4-Cl, 5-OCHCOOCH₃<br>　　　　　　　｜<br>　　　　　　　CH₃ | $n_D^{26}$ 1.5778 |
| 403 | " | " | 6-C₂H₅ | 2-F, 4-Cl, 5-OCHCOOCH₃<br>　　　　　　　｜<br>　　　　　　　CH₃ | $n_D^{27}$ 1.5836 |
| 404 | " | " | 6-CH₃ | 2-F, 4-Cl, 5-OCHCOOH<br>　　　　　　　｜<br>　　　　　　　CH₃ | 136–138 |
| 405 | " | " | 6,6-(CH₃)₂ | 2-F, 4-Cl, 5-OCHCOOH<br>　　　　　　　｜<br>　　　　　　　CH₃ | 210–212 |
| 406 | " | " | 6-C₂H₅ | 2-F, 4-Cl, 5-OCHCOOH<br>　　　　　　　｜<br>　　　　　　　CH₃ | 142–144 |
| 407 | " | " | 6-CH₃ | 2-F, 4-Cl, 5-OCHCOONa<br>　　　　　　　｜<br>　　　　　　　CH₃ | 215–220 dec. |
| 408 | " | " | 6-C₂H₅ | 2-F, 4-Cl, 5-OCHCOONa<br>　　　　　　　｜<br>　　　　　　　CH₃ | 78–85 |
| 409 | " | " | 6-CH₃ | 2-F, 4-Cl, 5-OCHCO—⌬<br>　　　　　　｜<br>　　　　　　CH₃ | 49–51 |
| 410 | " | " | " | 2-F, 4-Cl, 5-OCHCOSC₂H₅<br>　　　　　　　｜<br>　　　　　　　CH₃ | $n_D^{26}$ 1.6080 |
| 411 | " | " | " | 2-F, 4-Cl, 5-OCHCOSCH₂CH=CH₂<br>　　　　　　　｜<br>　　　　　　　CH₃ | $n_D^{26}$ 1.5985 |
| 412 | " | " | " | 2-F, 4-Cl, 5-OCH—C=NOH<br>　　　　　　｜　　｜<br>　　　　　　CH₃　⌬ | $n_D^{26.5}$ 1.5512 |
| 413 | " | " | " | 2-F, 4-Cl, 5-OCH—⌬<br>　　　　　　　｜<br>　　　　　　　CH₃ | 111–112 |
| 414 | " | " | 6-C₂H₅ | 2-F, 4-Cl, 5-OCH—⌬<br>　　　　　　　｜<br>　　　　　　　CH₃ | $n_D^{22}$ 1.6091 |
| 415 | " | " | 6-CH₃ | 2-F, 4-Cl, 5-OCHCN<br>　　　　　　｜<br>　　　　　　CH₃ | $n_D^{23}$ 1.6011 |

TABLE 1-continued

Structure formula:

$$\begin{array}{c} r^1 \\ r^2 \\ r^3 \\ r^4 \end{array} X \overset{N}{\underset{N}{\bigcirc}} \overset{=N}{Y} \text{—} \phi\text{—}(R)n$$

| Compound No. | X | Y | r¹, r², r³, r⁴ | (R)n | Physical Properties m.p. °C. |
|---|---|---|---|---|---|
| 416 | " | " | " | 2-F, 4-Cl, 5-OCH(COOC$_2$H$_5$)$_2$ | $n_D^{29.5}$ 1.5512 |
| 417 | " | " | 6-C$_2$H$_5$ | 2-F, 4-Cl, 5-OCHCCOOC$_2$H$_5$)$_2$ | $n_D^{29}$ 1.5540 |
| 418 | " | " | 6-CH$_3$ | 2-F, 4-Cl, 5-OCHCOOC$_2$H$_5$ | $n_D^{26}$ 1.5910 |
| 419 | " | " | " | 2-F, 4-Cl, 5-OCH$_2$—(isoxazole-CH$_3$) | 99–101 |
| 420 | " | " | " | 2-F, 4-Cl, 5-OCH$_2$—(isoxazoline-CH$_3$) | 138–140 |
| 421 | " | " | " | 2-F, 4-Cl, 5-OCH$_2$—(isoxazole-$^i$C$_3$H$_7$) | $n_D^{24}$ 1.5825 |
| 422 | " | " | " | 2-F, 4-Cl, 5-OCH$_2$CH$_2$O— (with thiadiazole-oxazoline-CH$_3$ system) | 90–93 |
| 423 | " | " | " | 2-F, 4-Cl, 5-OCH$_2$-(2-pyridyl) | 31–34 |
| 424 | " | " | " | 2-F, 4-Cl, 5-OCH$_2$C(CH$_3$)=NOCH$_2$CH=CH$_2$ | $n_D^{27}$ 1.5881 |
| 425 | " | " | " | 2-F, 4-Cl, 5-OCH$_2$C(CH$_3$)=NOCH$_2$CH=CH$_2$ (isomer) | $n_D^{27}$ 1.5861 |
| 426 | " | " | " | 2-F, 4-Cl, 5-OCH$_2$C(CH$_3$)=NOH | 175–181 |
| 427 | " | " | " | 2-F, 4-Cl, 5-OCH$_2$C≡CCH$_3$ | 150–151 |
| 428 | " | " | " | 2-F, 4-Cl, 5-OCH$_2$C≡CCl | $n_D^{26.5}$ 1.6135 |
| 429 | " | " | — | 2-F, 4-Cl, 5-OCH$_2$C≡CH | 139–140 |
| 430 | " | " | 6-CH$_3$ | " | 109–113 |
| 431 | " | " | " | 2-F, 4,5-(OCH$_2$C≡CH)$_2$ | 122.5–123.5 |
| 432 | " | " | " | 2,4-F$_2$, 5-OCH$_2$C≡CH | $n_D^{28.5}$ 1.5855 |
| 433 | " | " | " | 2,4-F$_2$, 6-Cl, 5-OCH$_2$C≡CH | $n_D^{28}$ 1.5742 |
| 434 | " | " | " | 2-F, 4-OCH$_3$, 5-OCH$_2$C≡CH | 158–160 |
| 435 | " | " | " | 2-F, 4-Br, 5-OCH$_2$C≡CH | 108–110 |
| 436 | " | " | " | 4-Cl, 5-OCH$_2$C≡CH | 110–111 |
| 437 | " | " | " | 2-Br, 4-Cl, 5-OCH$_2$C≡CH | 123–125 |
| 438 | " | " | 6,6-(CH$_3$)$_2$ | 2-F, 4-Cl, 5-OCH$_2$C≡CH | 105–108 |
| 439 | " | " | 5,6-(CH$_3$)$_2$(cis) | 2-F, 4-Cl, 5-OCH$_2$C≡CH | 122–123 |
| 440 | " | " | 5,6-(CH$_3$)$_2$(trans) | 2-F, 4-Cl, 5-OCH$_2$C≡CH | 118–119 |
| 441 | " | " | 6-CH$_2$OCH$_3$ | 2-F, 4-Cl, 5-OCH$_2$C≡CH | $n_D^{28}$ 1.6015 |
| 442 | " | " | 6-CH$_2$O$^i$C$_3$H$_7$ | 2-F, 4-Cl, 5-OCH$_2$C≡CH | $n_D^{28}$ 1.5950 |
| 443 | " | " | 6-C$_2$H$_5$ | 2-F, 4-Br, 5-OCH$_2$C≡CH | 111–113 |

TABLE 1-continued

Structure formula:

$$\begin{array}{c} r^1 \\ r^2 \\ r^3 \\ r^4 \end{array} \begin{array}{c} N-N \\ X \end{array} \begin{array}{c} =N-\phantom{x}(R)n \\ Y \end{array}$$

| Compound No. | X | Y | r¹, r², r³, r⁴ | (R)n | Physical Properties m.p. °C. |
|---|---|---|---|---|---|
| 444 | " | " | " | 2-F, 4-Cl, 5-OCH$_2$C≡CH | 121–122 |
| 445 | " | " | 6-C$_3$H$_7$ | 2-F, 4-Cl, 5-OCH$_2$C≡CH | 113–115 |
| 446 | " | " | 5-C$_2$H$_5$ | 2-F, 4-Cl, 5-OCH$_2$C≡CH | n$_D^{27}$ 1.6022 |
| 447 | " | " | 6-CH$_3$ | 2-F, 4-Cl, 5-OCH$_2$CBr=CBrCH$_3$ | n$_D^{26.5}$ 1.6160 |
| 448 | " | " | " | 2-F, 4-Cl, 5-OCH$_2$CF$_3$ | 83.5–85 |
| 449 | " | " | " | 2-F, 4-Cl, 5-OCH$_2$CH$_2$Br | 94–96 |
| 450 | " | " | " | 2-F, 4-Cl, 5-OC$_3$H$_6$CN | 103–104 |
| 451 | " | " | " | 2-F, 4-Cl, 5-OC$_3$H$_6$COOC$_2$H$_5$ | n$_D^{25.5}$ 1.5735 |
| 452 | " | " | " | 2-F, 4-Cl, 5-OC$_3$H$_6$SCH$_2$—⌬ | n$_D^{20.5}$ 1.6238 |
| 453 | " | " | " | 2-F, 4-Cl, 5-OC$_3$H$_6$S—⌬ | n$_D^{20}$ 1.6275 |
| 454 | " | " | " | 2-F, 4-Cl, 5-OC$_2$H$_4$OC$_2$H$_4$OCH$_3$ | 52–53 |
| 455 | " | " | " | 2-F, 4-Cl, 5-OC$_2$H$_4$OCH$_2$—⌬ | n$_D^{18}$ 1.6157 |
| 456 | " | " | " | 2-F, 4-Cl, 5-OC$_2$H$_4$OCH$_3$ | 90–90.5 |
| 457 | " | " | " | 2-F, 4-Cl, 5-OC$_2$H$_4$OCOCH$_3$ | n$_D^{22}$ 1.5810 |
| 458 | " | " | " | 2-F, 4-Cl, 5-OC$_2$H$_4$O—⌬ | 128–130 |
| 459 | " | " | " | 2-Br, 4-Cl, 5-OC$_2$H$_4$O—⌬ | 157–158 |
| 460 | " | " | " | 4-Cl, 5-OC$_2$H$_4$O—⌬ | 112–114 |
| 461 | " | " | " | 2-F, 4-Cl, 5-OC$_2$H$_4$O—⌬—CH$_3$ | 120–121 |
| 462 | " | " | " | 2-F, 4-Cl, 5-OC$_2$H$_4$O—⌬—Cl | 154–155 |
| 463 | " | " | " | 2-F, 4-Cl, 5-OC$_2$H$_4$—⌬ | 110–112 |
| 464 | " | " | | 2-F, 4-Cl, 5-OC$_2$H$_4$SCH$_2$COOCH$_3$ | 105–107 |

TABLE 1-continued

Structure formula:

$$\begin{matrix} r^1, r^2 & & & (R)n \\ r^3, r^4 & N & =N-\bigcirc \\ & X & Y \\ & & N \end{matrix}$$

| Compound No. | X | Y | r¹, r², r³, r⁴ | (R)n | Physical Properties m.p. °C. |
|---|---|---|---|---|---|
| 465 | " | " | " | 2-F, 4-Cl, 5-OC$_2$H$_4$SCH$_2$-◯ | $n_D^{21.6}$ 1.6262 |
| 466 | " | " | " | 2-F, 4-Cl, 5-OC$_2$H$_4$SCH$_3$ | $n_D^{26}$ 107 1.6086 |
| 467 | " | " | " | 2-F, 4-Cl, 5-OC$_2$H$_4$S-◯ | $n_D^{22}$ 1.6320 |
| 468 | " | " | " | 2-F, 4-Cl, 5-OCH$_2$CH=CCl$_2$ | 85–87 |
| 469 | " | " | " | 2-F, 4-Cl, 5-OCH$_2$CH=CH$_2$ | $n_D^{27}$ 1.6035 |
| 470 | " | " | " | 2,4-F$_2$, 5-OCH$_2$CH=CH$_2$ | $n_D^{28.5}$ 1.5965 |
| 471 | " | " | 6-C$_2$H$_5$ | 2-F, 4-Br, 5-OCH$_2$CH=CH$_2$ | $n_D^{22.5}$ 1.6172 |
| 472 | " | " | 6-CH$_3$ | 2-F, 4-Cl, 5-OCH$_2$CH=CHCOOC$_2$H$_5$ | $n_D^{25.5}$ 1.5905 |
| 473 | " | " | " | 2-F, 4-Cl, 5-OCH$_2$CH=CHCl | 94–95 |
| 474 | " | " | 6-C$_2$H$_5$ | 2-F, 4-Cl, 5-OCH$_2$CH=CHCl | 78–81 |
| 475 | " | " | 6-CH$_3$ | 2-F, 4-Cl, 5-OCH$_2$CN | $n_D^{24}$ 1.5675 |
| 476 | " | " | 6-C$_2$H$_5$ | 2-F, 4-Br, 5-OCH$_2$CN | $n_D^{23}$ 1.6153 |
| 477 | " | " | 6-CH$_3$ | 2-F, 4-Cl, 5-OCH$_2$COCH$_3$ | 106–108 |
| 478 | " | " | " | 2-F, 4-Cl, 5-OCH$_2$COO-◯-H | $n^{28}$ 1.5838 |
| 479 | " | " | " | 2-F, 4-Cl, 5-OCH$_2$COOCH$_2$CHClCH$_2$Cl | 172–177 dec. |
| 480 | " | " | " | 2-F, 4-Cl, 5-OCH$_2$COOCH$_3$ | 125–128 |
| 481 | " | " | " | 2-F, 4-Cl, 5-OCH$_2$-△ | 91–93 |
| 482 | " | " | " | 2-F, 4-Cl, 5-OCH$_2$OC$_2$H$_5$ | $n_D^{20.5}$ 1.5929 |
| 483 | " | " | " | 2-F, 4-Cl, 5-OCH$_2$OCH$_3$ | 70–72 |
| 484 | " | " | " | 2-F, 4-Cl, 5-OCH$_2$O-◯-Cl | 50–52 |
| 485 | " | " | 6-C$_2$H$_5$ | 2-F, 4-Cl, 5-OCH$_2$-◯ | $n_D^{21}$ 1.5790 |
| 486 | " | " | 6-CH$_3$ | 2-F, 4-Cl, 5-OCH$_2$-◯-CH$_3$ | $n_D^{26}$ 1.6005 |
| 487 | " | " | " | 2-F, 4-Cl, 5-OCH$_2$-◯-CN | 209–210 dec. |
| 488 | " | " | " | 2-F, 4-Cl, 5-OCH$_2$-◯-Cl | $n_D^{28}$ 1.6308 |

TABLE 1-continued

Structure formula

| Compound No. | X | Y | r¹, r², r³, r⁴ | (R)n | Physical Properties m.p. °C. |
|---|---|---|---|---|---|
| 489 | " | " | " | 2-F, 4-Cl, 5-OCH₂—⟨ ⟩—NO₂ | 176–177 |
| 490 | " | " | " | 2-F, 4-Cl, 5-OCH₂—⟨ ⟩—OCH₃ | 101–102 |
| 491 | " | " | " | 2-F, 4,5-(OCH₂—⟨ ⟩—Cl)₂ | 156–157 |
| 492 | " | " | " | 2-F, 4-Cl, 5-OCH₂SCH₂CH=CH₂ | $n_D^{21}$ 1.5999 |
| 493 | " | " | " | 2-F, 4-Cl, 5-OCH₂SCH₂COOCH₃ | $n_D^{19.5}$ 1.5973 |
| 494 | " | " | " | 2-F, 4-Cl, 5-OCH₂SCH₂—⟨ ⟩ | $n_D^{20.5}$ 1.6181 |
| 495 | " | " | " | 2-F, 4-Cl, 5-OCH₂SCH₃ | 69–71 |
| 496 | " | " | " | 2-F, 4-Cl, 5-OCH₂SO₂CH₃ | 56–59 |
| 497 | " | " | " | 2-F, 4-Cl, 5-OCH₂SO₂—⟨ ⟩ | 65–67 |
| 498 | " | " | " | 2-F, 4-Cl, 5-OCH₂SOCH₃ | 43–46 |
| 499 | " | " | " | 2-F, 4-Cl, 5-OCH₂SO—⟨ ⟩ | 166–168 dec. |
| 500 | " | " | " | 2-F, 4-Cl, 5-OCH₂S—⟨ ⟩ | $n_D^{29}$ 1.6420 |
| 501 | " | " | " | 2-F, 4-Cl, 5-OCH₂S—⟨ ⟩-CH₃ (ortho) | $n_D^{26}$ 1.6220 |
| 502 | " | " | " | 2-F, 4-Cl, 5-OCH₂S—⟨ ⟩—CH₃ | $n_D^{25.5}$ 1.6270 |
| 503 | " | " | " | 2-F, 4-Cl, 5-OCH₂S—⟨ ⟩—Cl | $n_D^{26}$ 1.6371 |

TABLE 1-continued

Structure formula:

$$\begin{array}{c} r^1\!\!-\!\!r^2 \\ r^3\!\!-\!\!r^4 \end{array}\!\!\!\!\!\!\!\!\!\!\!\!\!\!\begin{array}{c} N \\ X \end{array}\!\!\!\!\!\!\!\!\!\!\!\!\begin{array}{c} =N \\ N\!\!-\!\!Y \end{array}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!\!-(R)_n$$

| Compound No. | X | Y | $r^1, r^2, r^3, r^4$ | (R)n | Physical Properties m.p. °C. |
|---|---|---|---|---|---|
| 504 | " | " | " | 2-F, 4-Cl, 5-OCH$_2$S—⌬—OCH$_3$ | $n_D^{20.5}$ 1.6290 |
| 505 | " | " | " | 2-F, 4-Cl, 5-OCH$_2$Si(CH$_3$)$_3$ | 39–42 |
| 506 | " | " | " | 2-F, 4,5-(OCH$_3$)$_2$ | 127–128 |
| 507 | " | " | 6-C$_2$H$_5$ | 2-F, 4-Cl, 5-OCH$_3$ | 87–89 |
| 508 | " | " | 6-CH$_3$ | 2,4-Cl$_2$, 5-OCH$_2$C≡CH | 123–124 |
| 509 | " | " | " | 2-F, 4-Cl, 5-OCHC≡CH (—C$_6$H$_5$) | 47–49 |
| 510 | " | " | " | 2-F, 4-Cl, 5-OC(CH$_3$)$_2$COOC$_2$H$_5$ | 92–94 |
| 511 | " | " | 6,6-(CH$_3$)$_2$ | 2-F, 4-Cl, 5-OCOC(CH$_3$)$_2$COOC$_2$H$_5$ | $n_D^{24}$ 1.5600 |
| 512 | " | " | 6-CH$_3$ | 2-F, 4-Cl, 5-OCOCH$_3$ | 155–158 |
| 513 | " | " | 6-C$_2$H$_5$ | 2-F, 4-Cl, 5-OCOCH$_3$ | 136–137 |
| 514 | " | " | " | 2-F, 4-Cl, 5-OCO—⌬—Cl | 54–56 |
| 515 | " | " | 6-CH$_3$ | 2-F, 4-Cl, 5-OH | 164–166 |
| 516 | " | " | 6-C$_2$H$_5$ | 2-F, 4-Cl, 5-OH | 137–139 |
| 517 | " | " | 6-CH$_3$ | 2-F, 4-Cl, 5-OP(=S)(OC$_2$H$_5$)$_2$ | $n_D^{27.5}$ 1.5869 |
| 518 | " | " | " | 2-F, 4-Cl, 5-OP(=S)(OCH$_3$)$_2$ | 77–80 |
| 519 | " | " | " | 5-O—⌬—OCH(CH$_3$)COOC$_2$H$_5$ | $n_D^{20.5}$ 1.5985 |
| 520 | " | " | 6-C$_2$H$_5$ | 2-F, 4-Cl, 5-OSO$_2$—⌬—CH$_3$ | 112–114 |
| 521 | —CH$_2$— | " | " | 2-F, 4-Cl, 5-CH$_2$CN | 113–114 |
| 522 | " | " | " | 2-F, 4-Cl, 5-CH$_2$COOC$_2$H$_5$ | $n_D^{20}$ 1.5855 |
| 523 | " | " | " | 2-F, 4-Cl, 5-CH$_2$COOCH$_2$C≡CH | $n_D^{20.5}$ 1.5992 |
| 524 | " | " | " | 2-F, 4-Cl, 5-CH$_2$P(=O)(OC$_2$H$_5$)$_2$ | 75–77 |
| 525 | " | " | " | 2-F, 4-Cl, 5-CH=CHCOOC$_2$H$_5$ | 147–148.5 |

TABLE 1-continued

Structure formula $$\begin{array}{c} r^1 \\ r^2 \\ r^3 \\ r^4 \end{array} \underset{X}{\overset{N}{\diagup}} \underset{N}{\overset{}{\diagdown}} Y \overset{=N-\!\!\!\!\!\!\!\!\!\bigcirc\!\!-(R)_n}{} $$

| Compound No. | X | Y | r¹, r², r³, r⁴ | (R)n | Physical Properties m.p. °C. |
|---|---|---|---|---|---|
| 526 | " | " | " | 2-F, 4-Cl, 5-CH=CHCOOCHC₃H₇ <br> \|<br> C₃H₇ | 147–149 |
| 527 | " | " | " | 2-F, 4-Cl, 5-CH=CHCOOCH₂C≡CH | 116.5–117.5 |
| 528 | " | " | 6-CH₃ | 2-F, 4-Cl, 5-CH=CHCOOCH₃ | 161–164 |
| 529 | " | " | " | 2-F, 4-Cl, 5-CH=CHCOOH | 205–207 |
| 530 | " | " | " | 2-F, 4-Cl, 5-CH=CHCOONa | 257–260 |
| 531 | " | " | " | 2-F, 4-Cl, <br> 5-C(=O)-O-C(=O)-[2-Cl,4-F-phenyl] | 161–163 |
| 532 | " | " | " | 2-F, 4-Cl, 5-COO—cyclopentyl(H) | 97–98 |
| 533 | " | " | " | 2-F, 4-Cl, 5-COOC(CH₃)₂C≡CH | 134–135 |
| 534 | " | " | " | 2-F, 4-Cl, 5-COOC(CH₃)₂CH₂—C₆H₅ | $n_D^{21.5}$ 1.5820 |
| 535 | " | " | " | 2-F, 4-Cl, 5-COOC(CH₃)₂CN | 133.5–135 |
| 536 | " | " | " | 2-F, 4-Cl, 5-COOCH(CH₃)COOC₂H₅ | 71–72 |
| 537 | " | " | " | 2-F, 4-Cl, 5-COOⁱC₄H₉ | 89–90 |
| 538 | " | " | " | 4-Cl, 5-COOC₂H₅ | $n_D^{23}$ 1.6150 |
| 539 | " | " | " | 2-F, 4-Cl, 5-COOC₂H₅ | 88–90 |
| 540 | " | " | " | 2-OCH₃, 4-Cl, 5-COOC₂H₅ | 77–79 |
| 541 | " | " | " | 2-F, 4-Cl, 5-COOC₃H₇ | 101–102 |
| 542 | " | " | " | 2-F, 4-Cl, 5-COOCH(C₂H₅)C₂H₅ | 66–67.5 |
| 543 | " | " | " | 2-F, 4-Cl, 5-COOCH(C₂H₅)COOC₂H₅ | 85–86.5 |
| 544 | " | " | " | 2-F, 4-Cl, 5-COOCH(C₃H₇)COOC₂H₅ | 78–80 |
| 545 | " | " | " | 2-F, 4-Cl, 5-COOCH(C₄H₉)COOC₂H₅ | 58–60 |

TABLE 1-continued

Structure formula $$\begin{array}{c} r^1 \\ r^2 \\ r^3 \\ r^4 \end{array} X \begin{array}{c} N = \\ N \end{array} Y = N - \text{phenyl}(R)n$$

| Compound No. | X | Y | r¹, r², r³, r⁴ | (R)n | Physical Properties m.p. °C. |
|---|---|---|---|---|---|
| 546 | " | " | " | 2-F, 4-Cl, 5-COOCHC≡CH (with phenyl substituent on CH) | $n_D^{19.5}$ 1.6066 |
| 547 | " | " | " | 2-F, 4-Cl, 5-COO$^i$C$_3$H$_7$ | 90–91 |
| 548 | " | " | " | 2-F, 5-COO$^i$C$_3$H$_7$ | 107.5–108.5 |
| 549 | " | " | " | 2-F, 4-Cl, 5-COOCHC$_3$H$_7$ (CH$_3$ branch) | 78–80 |
| 550 | " | " | " | 2-F, 4-Cl, 5-COOCHCH=CHCOO$^i$C$_3$H$_7$ (CH$_3$ branch) | 89.5–91 |
| 551 | " | " | " | 2-F, 4-Cl, 5-COOCHCH=CHCOOCH$_3$ (CH$_3$ branch) | 87–88 |
| 552 | " | " | " | 2-F, 4-Cl, 5-COOCH$_2$-cyclopropyl | 91–93 |
| 553 | " | " | " | 2-F, 4-Cl, 5-COOCH$_2$-(2,2-dichlorocyclopropyl) | 110–111.5 |
| 554 | " | " | " | 2-F, 4-Cl, 5-COOC$_2$H$_4$OC$_2$H$_4$OC$_2$H$_4$OCH$_3$ | $n_D^{22.5}$ 1.5671 |
| 555 | " | " | " | 2-F, 4-Cl, 5-COOC$_2$H$_4$(OC$_2$H$_4$)$_3$OCH$_3$ | $n_D^{22.5}$ 1.5596 |
| 556 | " | " | " | 2-F, 4-Cl, 5-COOC$_3$H$_6$(OC$_3$H$_6$)$_7$OCH$_3$ | $n_D^{21.5}$ 1.5115 |
| 557 | " | " | " | 2-F, 4-Cl, 5-COOCH$_2$Si(CH$_3$)$_3$ | 98–101 |
| 558 | " | " | " | 4-Cl, 5-COOCH$_3$ | 101–102 |
| 559 | " | " | " | 2-F, 4-Cl, 5-COOCH$_3$ | 99–100.5 |
| 560 | " | " | " | 4-Cl, 5-COOH | 229 dec. |
| 561 | " | " | " | 2-F, 4-Cl, 5-COOH | 210–213 |
| 562 | " | " | " | 2-F, 4-Cl, 5-COON=C—CH$_3$ (CH$_3$ branch) | 118–119.5 |
| 563 | " | " | " | 2-F, 4-Cl, 5-COONa | 285–286 |
| 564 | " | " | " | 2-F, 4-Cl, 5-CO-phenyl | $n_D^{26}$ 1.6210 |
| 565 | " | " | " | 2-F, 4-Cl, 5-OCHC≡CH (C$_2$H$_5$ branch) | $n_D^{22}$ 1.6036 |
| 566 | " | " | — | 2-F, 4-Cl, 5-OCHCN (C$_2$H$_5$ branch) | 91–92 |
| 567 | " | " | 6-OCH$_3$ | 2-F, 4-Cl, 5-OOCHCN (C$_2$H$_5$ branch) | $n_D^{28}$ 1.6001 |

TABLE 1-continued

Structure formula $$\begin{array}{c} r^1 \\ r^2 \\ r^3 \\ r^4 \end{array} \diagdown \begin{array}{c} N = \\ X \end{array} \diagup \begin{array}{c} N \\ N \end{array} \diagdown Y = N - \text{Ph}(R)n$$

| Compound No. | X | Y | r¹, r², r³, r⁴ | (R)n | Physical Properties m.p. °C. |
|---|---|---|---|---|---|
| 568 | " | " | " | 2-F, 4-Cl, 5-OCHCOOC$_2$H$_5$<br>    \|<br>    C$_2$H$_5$ | 59–60 |
| 569 | " | " | " | 2-F, 4-Cl, 5-OCHCOO$^i$C$_3$H$_7$<br>    \|<br>    C$_2$H$_5$ | 70–70.5 |
| 570 | " | " | " | 2-F, 4-Cl, 5-OCHCOOCH$_2$C≡CH<br>    \|<br>    C$_2$H$_5$ | 91.5–92 |
| 571 | " | " | " | 2-F, 4-Cl, 5-OCHCOOCH$_3$<br>    \|<br>    C$_2$H$_5$ | 76–78 |
| 572 | " | " | " | 2-F, 4-Cl, 5-OCHCOOH<br>    \|<br>    C$_2$H$_5$ | 118–120 |
| 573 | " | " | " | 2-F, 4-Cl, 5-OCHC≡CH<br>    \|<br>    C$_3$H$_7$ | 77–80 |
| 574 | " | " | " | 2-F, 4-Cl, 5-OCHC≡CH<br>    \|<br>    C$_4$H$_9$ | 75–78 |
| 575 | " | " | " | 2-F, 4-Cl, 5-OCHC≡CH<br>    \|<br>    C$_5$H$_{11}$ | 64–67 |
| 576 | " | " | " | 2-F, 4-Cl, 5-O$^i$C$_3$H$_7$ | $n_D^{28}$ 1.6012 |
| 577 | " | " | " | 2-F, 4-Cl, 5-OCHC=NOCOCH$_2$Cl<br>         /       \|<br>      CH$_3$   NH$_2$ | 128–129 |
| 578 | " | " | " | 2-F, 4-Cl, 5-OCHC$_2$H$_5$<br>    \|<br>    CH$_3$ | $n_D^{21.5}$ 1.5912 |
| 579 | " | " | — | 2-F, 4-Cl, 5-OCHC≡CH<br>    \|<br>    CH$_3$ | 124–126 |
| 580 | " | " | 6-CH$_3$ | 2-F, 4-Cl, 5-OCHC≡CH<br>    \|<br>    CH$_3$ | 85–86 |
| 581 | " | " | " | 2-F, 4-Cl, 5-OCHCH$_2$Br<br>    \|<br>    CH$_3$ | $n_D^{20.5}$ 1.5879 |
| 582 | " | " | " | 2-F, 4-Cl, 5-OCHCH$_2$O—Ph<br>    \|<br>    CH$_3$ | $n_D^{20.5}$ 1.6100 |
| 583 | " | " | " | 2-F, 4-Cl, 5-OCHCH$_2$SC$_2$H$_5$<br>    \|<br>    CH$_3$ | $n_D^{20}$ 1.5989 |
| 584 | " | " | " | 2-F, 4-Cl, 5-OCHCH$_2$SCH$_2$—Ph<br>    \|<br>    CH$_3$ | $n_D^{20.5}$ 1.6003 |

TABLE 1-continued

Structure formula

| Compound No. | X | Y | $r^1, r^2, r^3, r^4$ | (R)n | Physical Properties m.p. °C. |
|---|---|---|---|---|---|
| 585 | " | " | " | 2-F, 4-Cl, 5-OCHCH$_2$S—C$_6$H$_5$<br>              \|<br>              CH$_3$ | $n_D^{20.5}$ 1.6205 |
| 586 | " | " | " | 2-F, 4-Cl, 5-OCHCH=CHCOOC$_2$H$_5$<br>             \|<br>             CH$_3$ | $n_D^{22}$ 1.5837 |
| 587 | " | " | " | 2-F, 4-Cl, 5-OCHCN<br>           \|<br>           CH$_3$ | 93–95 |
| 588 | " | " | " | 2-F, 4-Cl, 5-OCHCO—pyrazolyl<br>           \|<br>           CH$_3$ | 108–110 |
| 589 | " | " | " | 2-F, 4-Cl, 5-OCHCOO—cyclopentyl<br>             \|<br>             CH$_3$ | 98.5–99.5 |
| 590 | " | " | " | 2-F, 4-Cl, 5-OCHCOO—cyclohexyl<br>             \|<br>            CH$_3$ | $n_D^{22.5}$ 1.5751 |
| 591 | " | " | " | 2-F, 4-Cl, 5-OCHCOO—(1-ethynylcyclohexyl with CH$_3$)<br>            \|<br>            CH$_3$ | 115–116 |
| 592 | " | " | " | 2-F, 4-Cl, 5-OCHCOOC(CH$_3$)$_2$C≡CH<br>            \|<br>            CH$_3$ | 143.5–144 |
| 593 | " | " | " | 2-F, 4-Cl, 5-OCHCOOC$_{10}$H$_{21}$<br>            \|<br>            CH$_3$ | $n_D^{23.5}$ 1.5450 |
| 594 | " | " | " | 2-F, 4-Cl, 5-OCHCOOC$_2$H$_5$<br>             \|<br>            CH$_3$ | 61.5–62.5 |
| 595 | " | " | 6-C$_2$H$_5$ | 2-F, 4-Cl, 5-OCHCOOC$_2$H$_5$<br>            \|<br>            CH$_3$ | 81–82 |
| 596 | " | " | 6-CH$_3$ | 2-F, 4-Cl, 5-OCHCOOC$_3$H$_7$<br>            \|<br>            CH$_3$ | $n_D^{19.5}$ 1.5687 |
| 597 | " | " | " | 2-F, 4-Cl, 5-OCHCOOCHC≡CH<br>            \|      \|<br>            CH$_3$  C$_2$H$_5$ | 103–104 |
| 598 | " | " | " | 2-F, 4-Cl, 5-OCHCOO$^i$C$_3$H$_7$<br>            \|<br>            CH$_3$ | 71–72 |
| 599 | " | " | " | 2-F, 4-Cl, 5-OCHCOOCHC$_2$H$_5$<br>            \|       \|<br>            CH$_3$   CH$_3$ | $n_D^{20.5}$ 1.5640 |

TABLE 1-continued

Structure formula:

$$\begin{matrix} r^1 & & & & (R)_n \\ r^2 & N & & & \\ & \diagdown & = N - \text{Ph} & \\ r^3 & X & \diagup & & \\ r^4 & & N-Y & & \end{matrix}$$

| Compound No. | X | Y | $r^1, r^2, r^3, r^4$ | (R)n | Physical Properties m.p. °C. |
|---|---|---|---|---|---|
| 600 | " | " | — | 2-F, 4-Cl, 5-OCH(CH$_3$)COOCH$_2$C≡CH | 107–109 |
| 601 | " | " | 6-CH$_3$ | 2-F, 4-Cl, 5-OCH(CH$_3$)COOCH$_2$C≡CH | 116–116.5 |
| 602 | " | " | 6,6-(CH$_3$)$_2$ | 2-F, 4-Cl, 5-OCH(CH$_3$)COOCH$_2$C≡CH | $n_D^{23}$ 1.5814 |
| 603 | " | " | 6-C$_2$H$_5$ | 2-F, 4-Cl, 5-OCH(CH$_3$)COOCH$_{1\,2}$C≡CH | 92–94 |
| 604 | " | " | 6-CH$_3$ | 2-F, 4-Cl, 5-OCH(CH$_3$)COOCH$_2$CH$_2$Cl | 58.5–60.5 |
| 605 | " | " | " | 2-F, 4-Cl, 5-OCH(CH$_3$)COOC$_2$H$_4$OC$_2$H$_5$ | $n_D^{22.5}$ 1.5711 |
| 606 | " | " | " | 2-F, 4-Cl, 5-OCH(CH$_3$)COOC$_2$H$_4$OCH$_2$Ph | $n_D^{18.5}$ 1.5946 |
| 607 | " | " | " | 2-F, 4-Cl, 5-OCH(CH$_3$)COOCH$_2$CH=CCl$_2$ | $n_D^{22.5}$ 1.5929 |
| 608 | " | " | " | 2-F, 4-Cl, 5-OCH(CH$_3$)COOCH$_2$Si(CH$_3$)$_3$ | $n_D^{20}$ 1.5615 |
| 609 | " | " | " | 2-F, 4-Cl, 5-OCH(CH$_3$)COOCH$_3$ | 73–75 |
| 610 | " | " | " | 2-F, 4-Cl, 5-OCH(CH$_3$)COOCH(Ph)C≡CH | $n_D^{21}$ 1.5957 |
| 611 | " | " | " | 2-F, 4-Cl, 5-OCH(CH$_3$)COOH | 103–105 |
| 612 | " | " | " | 2-F, 4-Cl, 5-OCH(CH$_3$)COON=C(CH$_3$)—CH$_3$ | $n_D^{19.5}$ 1.5804 |
| 613 | " | " | " | 2-F, 4-Cl, 5-OCH(CH$_3$)COO—Ph | 142–143 |
| 614 | " | " | " | 2-F, 4-Cl, 5-OCH(CH$_3$)CSNH$_2$ | 134.5–135 |

TABLE 1-continued

Structure formula:

$$\begin{matrix} r^1 & & & \\ r^2 & & N & \\ & \diagdown & \| & =N-\text{Ar}(R)_n \\ & X & & \\ r^3 & \diagup & \diagdown & \\ r^4 & & N-Y & \end{matrix}$$

| Compound No. | X | Y | r¹, r², r³, r⁴ | (R)n | Physical Properties m.p. °C. |
|---|---|---|---|---|---|
| 615 | " | " | " | 2-F, 4-Cl, 5-OCH₂-(2,2-dichlorocyclopropyl) | 81–83 |
| 616 | " | " | " | 2-F, 4-Cl, 5-OCH₂-N(pyrazolyl) | 110–112 |
| 617 | " | " | — | 2-F, 4-Cl, 5-OCH₂C≡CH | 104–106.5 |
| 618 | " | " | 6-CH₃ | 2-F, 4-Cl, 5-OCH₂C≡CH | 129–130 |
| 619 | " | " | 6-C₂H₅ | 2-F, 4-Cl, 5-OCH₂C≡CH | 149–150 |
| 620 | " | " | 6-CH₃ | 2-F, 4-Cl, 5-(OC₂H₄)₃OCH₃ | $n_D^{17.5}$ 1.5740 |
| 621 | " | " | " | 2-F, 4-Cl, 5-(OC₂H₄)₄OCH₃ | $n_D^{19.5}$ 1.5572 |
| 622 | " | " | " | 2-F, 4-Cl, 5-OC₂H₄CH(SCH₃)CH₃ | $n_D^{26}$ 1.6132 |
| 623 | " | " | " | 2-F, 4-Cl, 5-OC₃H₆O-phenyl | 82–83 |
| 624 | " | " | " | 2-F, 4-Cl, 5-OC₂H₄O-(naphthalen-1-yl) | 130–131 |
| 625 | " | " | " | 2-F, 4-Cl, 5-OC₂H₄-O-(naphthalen-2-yl) | 127–128 |
| 626 | " | " | " | 2-F, 4-Cl, 5-O₂H₄-O-(1,3-benzodioxol-5-yl) | 102–103 |
| 627 | " | " | " | 2-F, 4-Cl, 5-OC₂H₄OC₂H₄O-phenyl | 79–80 |
| 628 | " | " | " | 2-F, 4-Cl, 5-OC₂H₄OCH₃ | 69–70 |
| 629 | " | " | " | 2-F, 4-Cl, 5-OC₂H₄OCH=CH₂ | 61–62 |
| 630 | " | " | " | 2-F, 4-Cl, 5-OC₂H₄OCONHCH₃ | 102–103 |
| 631 | " | " | " | 2-F, 4-Cl, 5-OC₂H₄OH | 65–65.5 |
| 632 | " | " | " | 2-F, 4-Cl, 5-OC₂H₄O-phenyl | 96–97 |
| 633 | " | " | " | 2-Br, 4-Cl, 5-OC₂H₄O-phenyl | 121–123 |

TABLE 1-continued

Structure formula:

$$\begin{matrix} r^1 & & & & & & (R)n \\ r^2 & & N & & & & \\ & & & \diagdown & & & \\ & & & & = N - \text{Ph} & \\ r^3 & X & & Y & & & \\ r^4 & & N & & & & \end{matrix}$$

| Compound No. | X | Y | r¹, r², r³, r⁴ | (R)n | Physical Properties m.p. °C. |
|---|---|---|---|---|---|
| 634 | " | " | " | 4-Cl, 5-OC₂H₄O—⟨phenyl⟩ | 98–100 |
| 635 | " | " | " | 2-F, 4-Cl, 5-OC₂H₄O—⟨phenyl-F⟩ | 87–88 |
| 636 | " | " | " | 2-F, 4-Cl, 5-OC₂H₄O—⟨phenyl-Cl,Cl⟩ | 71–72 |
| 637 | " | " | " | 2-F, 4-Cl, 5-OC₂H₄O—⟨phenyl-CF₃⟩ | 87–88 |
| 638 | " | " | " | 2-F, 4-Cl, 5-OC₂H₄O—⟨phenyl-CH₃⟩ | 96–97 |
| 639 | " | " | " | 2-F, 4-Cl, 5-OC₂H₄O—⟨phenyl-Cl⟩ | 96–97 |
| 640 | " | " | " | 2-F, 4-Cl, 5-OC₂H₄O—⟨phenyl-F⟩ | 85–86 |
| 641 | " | " | " | 2-F, 4-Cl, 5-OC₂H₄O—⟨phenyl⟩—Br | 117–118 |
| 642 | " | " | " | 2-F, 4-Cl, 5-OC₂H₄O—⟨phenyl⟩—CH₃ | 105–107 |
| 643 | " | " | " | 2-F, 4-Cl, 5-OC₂H₄O—⟨phenyl⟩—Cl | 136–137.5 |
| 644 | " | " | " | 2-F, 4-Cl, 5-OC₂H₄O—⟨phenyl⟩—F | 74–75 |

TABLE 1-continued

Structure formula

| Compound No. | X | Y | r¹, r², r³, r⁴ | (R)n | Physical Properties m.p. °C. |
|---|---|---|---|---|---|
| 645 | " | " | " | 2-F, 4-Cl, 5-OC$_2$H$_4$O—⟨phenyl⟩—NO$_2$ | 46–47 |
| 646 | " | " | " | 2-F, 4-Cl, 5-OC$_2$H$_4$O—⟨phenyl⟩—OCH$_3$ | 124–125 |
| 647 | " | " | " | 2-F, 4-Cl, 5-OCH$_2$CH=CCl$_2$ | 112–113 |
| 648 | " | " | " | 2-F, 4-Cl, 5-OCH$_2$CH=CHCOOC$_2$H$_5$ | $n_D^{19.5}$ 1.5865 |
| 649 | " | " | " | 2-F, 4-Cl, 5-OCH$_2$COO—⟨cyclopentyl H⟩ | 113–115 |
| 650 | " | " | " | 2-F, 4-Cl, 5-OCH$_2$COOC$_2$H$_5$ | 141–143 |
| 651 | " | " | " | 2-F, 4-Cl, (CH$_3$—⟨phenyl⟩—SO$_3$H salt) | 142–144 |
| 652 | " | " | " | 2-F, 4-Cl, (HCl salt) | 150–151 |
| 653 | " | " | " | 2-F, 4-Cl, 5-OCH$_2$COO$^i$C$_3$H$_7$ | 115–117 |
| 654 | " | " | " | 2-F, 4-Cl, 5-OCH$_2$COOCHCOOC$_2$H$_5$ \| CH$_3$ | 71–74 |
| 655 | " | " | " | 2-F, 4-Cl, 5-OCH$_2$COOCH$_2$C≡CH | 140–142 |
| 656 | " | " | " | 2-F, 4-Cl, 5-OCH$_2$COOCH$_2$CH=CH$_2$ | 97–99 |
| 657 | " | " | " | 2-F, 4-Cl, 5-OCH$_2$COOCH$_2$CHClCH$_2$Cl | 107–110 |
| 658 | OCOCH$_3$ \| —C— \| COOCH$_3$ | " | — | 2-F, 4-Cl, 5-OCH$_2$COOCH$_3$ | 104.5–105 |
| 659 | —CH$_2$— | " | 6-CH$_3$ | 2-F, 4-Cl, 5-OCH$_2$COOCH$_3$ | 124–126 |
| 660 | " | " | " | 2-F, 4-Cl, 5-OCH$_2$COOH | 162–163 |
| 661 | " | " | " | 2-F, 4-Cl, 5-OCH$_2$OC$_2$H$_5$ | 44–45 |
| 662 | " | " | " | 2-F, 4-Cl, 5-OCH$_2$OCH$_3$ | 68–69 |
| 663 | " | " | " | 2-F, 4-Cl, 5-OCH$_2$O—⟨phenyl⟩—Cl | 82–83 |
| 664 | " | " | " | 2-F, 4-Cl, 5-OCH$_2$S—⟨phenyl⟩ | 101–102 |
| 665 | " | " | 6-C$_2$H$_5$ | 2-F, 4-Cl, 5-OCH$_2$S—⟨phenyl⟩ | 106–108 |
| 66 | " | " | 6-CH$_3$ | 2-F, 4-Cl, 5-OCH=CHCH$_2$COOC$_2$H$_5$ | $n_D^{19.5}$ 1.5975 |

TABLE 1-continued

Structure formula:

$$\begin{array}{c} r^1 \\ r^2 \\ r^3 \\ r^4 \end{array} \underset{X}{\overset{N}{\diagup}} \underset{N}{\overset{}{\diagdown}} \underset{Y}{\overset{}{\diagup}} =N-\underset{}{\bigcirc}(R)n$$

| Compound No. | X | Y | r¹, r², r³, r⁴ | (R)n | Physical Properties m.p. °C. |
|---|---|---|---|---|---|
| 667 | " | " | " | 2-F, 4-Cl, 5-OCHC≡CH (—C₆H₅) | 137–139 |
| 668 | " | " | " | 2-F, 4-Cl, 5-OCHCOOC₂H₅ (—C₆H₅) | 159–160 |
| 669 | " | " | " | 2-F, 4-Cl, 5-OH | 161–163 |
| 670 | " | " | " | 2-F, 4-Cl, 5-OH, 6-I | 58–60 |
| 671 | " | " | " | 2-F, 4-Cl, 5-O—C₆H₅ | 107–109 |
| 672 | —N(C₆H₅)— | " | — | 4-Cl | 250 up |
| 673 | —N(C₂H₅)— | " | — | 4-Cl | 94–97 |
| 674 | —N(CH₃)— | " | — | 2-F, 4-Cl, 5-OCH₂C≡CH | 130–132 |
| 675 | " | " | — | 2-F, 4-Cl, 5-OCH(CH₃)COOC₂H₅ | 75–78 |
| 676 | " | " | — | 2-F, 4-Cl, 5-OCH(CH₃)COOCH₂C≡CH | 138–138.5 |
| 677 | —CH₂S— | " | — | 4-Cl | 120–122 |
| 678 | —CH(CH₃)—S— | " | — | 2-F, 4-Cl | 97–100 |
| 679 | —CH₂CH₂— | " | — | 2-F, 4-Cl, 5-OCH(CH₃)COOC₂H₅ | 79–80.5 |
| 680 | " | " | — | 2-F, 4-Cl, 5-OCH₂COOCH₃ | 101–103 |
| 681 | —CH₂— | " | 6-CH₃ | 2-F, 4-Cl, 5-COOC(CH₃)₂COOCH₃ | 117–119 |
| 682 | —O— | " | " | 2-F, 4-Cl, 5-COOCH(CH₃)COOCH₃ | 173–176 |
| 683 | —CH₂— | " | " | 2-F, 4-Cl, 5-COOCH(CH₃)COOC₂H₅ | 83–84 |
| 684 | " | " | " | 2-F, 4-Cl, 5-COOCH(CH₃)COOCH₃ | 158–160 |

TABLE 1-continued

Structure formula:

$$\begin{array}{c} r^1 \\ r^2 \\ r^3 \\ r^4 \end{array} X \underset{N-Y}{\overset{N}{\bigtriangleup}} = N - \text{Ph}(R)_n$$

| Compound No. | X | Y | r¹, r², r³, r⁴ | (R)n | Physical Properties m.p. °C |
|---|---|---|---|---|---|
| 685 | " | " | " | 2-F, 4-Cl, 5-O-C(=N-N=C(CH₃)-S) (thiadiazole) | 142.5–143.5 |
| 686 | " | " | " | 2-F, 4-Cl, 5-COOCH(CH₃)C≡CH | 115.5–117 |
| 687 | " | " | " | 2-F, 4-Cl, 5-COOCH(COOC₂H₅)₂ | 118–119.5 |
| 688 | " | " | " | 2-F, 4-Cl, 5-OCH₂COOCH₂CH₂O-Ph | |
| 689 | " | " | " | 2-F, 4-Cl, 5-COOC₂H₄(OC₂H₄)₆OCH₃ | $n_D^{20.5}$ 1.5429 |
| 690 | —O— | " | " | 2-F, 4-Cl, 5-COOC(CH₃)₂CN | 173–175 |
| 691 | " | " | " | 2-F, 4-Cl, 5-COOCH(CH₃)CH=CHCOOC₂H₅ | $n_D^{21.5}$ 1.5767 |
| 692 | " | " | " | 2-F, 4-Cl, 5-COO$^t$C₄H₉ | 124–126 |
| 693 | —CH₂— | " | " | 2-F, 4-Cl, 5-O-(2-pyridyl) | 145–146.5 |
| 694 | " | " | " | 2-F, 4-Cl, 5-COOCH₂CH=CHCOOC₂H₅ | 115–116 |
| 695 | " | " | " | 2-F, 4-Cl, 5-COOC₃H₆COOC₂H₅ | 52–53 |
| 696 | CH₂ | " | " | 2-F, 4-Cl, 5-O-(5-chloro-2-(methylamino)pyrimidin-4-yl) | 199.5–201 |
| 697 | —CH₂CH₂— | " | — | 2-F, 4-Cl, 5-OC₂H₄O-Ph | 111–112 |
| 698 | —C(COOC₂H₅)(OH)— | " | 6,6-(CH₃)₂ | 2-F, 4-Cl, 5-OCH₂COOCH₃ | 108.5–109 |
| 699 | —CH₂— | " | " | 2-F, 4-Cl, 5-OC₂H₄O-(6-methyl-2-pyridyl) | 124–125 |
| 700 | —O— | " | " | 2-F, 4-Cl, 5-OCH₂O-Ph | $n_D^{18.5}$ 1.6119 |

TABLE 1-continued

Structure formula

| Compound No. | X | Y | r¹, r², r³, r⁴ | (R)n | Physical Properties m.p. °C. |
|---|---|---|---|---|---|
| 701 | —CH$_2$— | " | " | 2-F, 4-Cl, 5-OC$_2$H$_4$O—⬡ | 96–99 |
| 702 | " | " | " | 2-F, 4-Cl, 5-OC$_2$H$_4$O—(thiazole) | 121.5–122.5 |
| 703 | —O— | " | " | 2-F, 4-Cl, 5-O—(thiazole) | 118–120 |
| 704 | " | " | " | 2-F, 4-Cl, 5-OCH$_2$OCH$_2$C≡CH | 72–73 |
| 705 | —CH$_2$— | " | " | 2-F, 4-Cl, 5-OCH=CHCOOC$_2$H$_5$ | 72–73 |
| 706 | " | " | " | 2-F, 4-Cl, 5-OCH$_2$SCH$_3$ | $n_D^{24.5}$ 1.6135 |
| 707 | " | " | " | 2-F, 4-Cl, 5-SCH$_2$COO$^i$C$_3$H$_7$ | 79–82 |
| 708 | " | " | " | 2,4-F$_2$, 3-OCH$_2$C≡CH | $n_D^{24.5}$ 1.5936 |
| 709 | " | " | " | 2-F, 4-Cl, 5-OCH$_2$OCH$_2$OCH$_3$ | $n_D^{26}$ 1.5840 |
| 710 | " | " | " | 2,4-F$_2$, 3-COOC$_2$H$_5$ | |
| 711 | " | " | " | 2-F, 4-Cl, 5-OCH$_2$OC(CH$_3$)$_2$C≡CH | 135–137 |
| 712 | " | " | " | 2-F, 4-Cl, 5-OCH$_2$OCH$_2$CH=CH$_2$ | 42–43 |
| 713 | " | " | " | 2-F, 4-Cl, 5-CF$_3$ | 80–81 |
| 714 | " | " | " | 2-F, 4-Cl, 5-OC(CH$_3$)$_2$C≡CH | 45–50 |
| 715 | " | " | " | 2-F, 4-Cl, 5-OCH$_2$COOC$_2$H$_4$O—⬡ | |
| 716 | " | " | " | 2-F, 4-Cl, 5-COCH$_3$ | 93–94 |
| 717 | " | " | " | 2-F, 4-Cl, 5-COOCH(CH$_3$)COOC$_2$H$_5$ | $n_D^{24.5}$ 1.5605 |
| 718 | " | " | " | 2-F, 4-Cl, 5-COOCH(CH$_3$)COO$^i$C$_4$H$_9$ | 89–93 |
| 719 | " | " | " | 2-F, 4-Cl, 5-COOCH(CH$_3$)COO$^i$C$_3$H$_7$ | 92–96 |
| 720 | " | " | " | 2-F, 4-Cl, 5-COOCH(CH$_3$)COOC$_3$H$_7$ | $n_D^{23.5}$ 1.5608 |
| 721 | " | " | " | 2-F, 5-COOC(CH$_3$)$_2$CN | 114–115 |
| 722 | " | " | " | 2-F, 4-Cl, 5-C(CH$_3$)=NOH | 158–170 |

TABLE 1-continued

Structure formula:

$$\begin{array}{c} r^1 \\ r^2 \\ r^3 \\ r^4 \end{array} \diagdown N \diagup \begin{array}{c} \\ \\ X \end{array} \diagdown \begin{array}{c} \\ N \\ Y \end{array} = N - \bigcirc (R)n$$

| Compound No. | X | Y | $r^1, r^2, r^3, r^4$ | (R)n | Physical Properties m.p. °C. |
|---|---|---|---|---|---|
| 723 | " | " | " | 2-F, 4-Cl, 5-C(=NOCH$_2$COOCH$_3$)CH$_3$ | $n_D^{24.5}$ 1.5685 |
| 724 | " | " | " | 2-F, 5-COOH | 213–214 |
| 725 | " | " | " | 2-F, 5-COO$^i$C$_4$H$_9$ | 113–114.5 |
| 726 | —O— | " | " | 2-F, 4-Cl, 5-CN | 136–138 |
| 727 | —CH$_2$— | " | " | 2-F, 4-Cl, 5-CN | 167.5–169 |
| 728 | " | " | " | 2-F, 4-Cl, 5-COS$^i$C$_3$H$_7$ | $n_D^{25.5}$ 1.6195 |
| 729 | " | " | " | 2-F, 4-Cl, 5-COCH(OCH$_3$)$_2$ | 89–90.5 |
| 730 | —O— | " | " | 2-F, 4-Cl, 5-O—(tetrahydropyran-2-yl) | $n_D^{24.5}$ 1.5647 |
| 731 | —CH$_2$— | " | " | 2-F, 4-Cl, 5-OCH(CH$_3$)OCH$_3$ | $n_D^{24.5}$ 1.5900 |
| 732 | " | " | " | 2-F, 4-Cl, 5-OCH(CH$_3$)OC$_2$H$_5$ | 74–76 |
| 733 | " | " | " | 2-F, 5-O—C$_6$H$_4$—OCH(CH$_3$)COOC$_2$H$_5$ | $n_D^{24}$ 1.6080 |
| 734 | —O— | " | " | 4-Cl, 5-O—C$_6$H$_4$—OCH(CH$_3$)COOC$_2$H$_5$ | $n_D^{24}$ 1.5850 |
| 735 | —CH$_2$— | " | " | 4-Cl, 5-C$_6$H$_5$ | $n_D^{24}$ 1.6530 |
| 736 | —Oab,4 | " | " | 4-Cl, 5-C$_6$H$_5$ | 153–154 |
| 737 | —CH$_2$— | " | 2-F, 4-Cl, 5-NHCH(CH$_3$)CON(CH$_3$)$_2$ | 106 |  |
| 738 | " | " | " | 2-F, 4-Cl, 5-OCH$_2$S$^i$C$_3$H$_7$ | 66.5–67 |
| 739 | —O— | " | " | 2-F, 4-Cl, 5-OCH$_2$S$^i$C$_3$H$_7$ | 64–65 |
| 740 | —CH$_2$— | " | " | 2-F, 4-Cl, 5-SCH$_2$COOH | *1 |
| 741 | —CH$_2$S— | " | 6=CH$_2$ | 2-F, 4-Cl, 5-OCH$_2$C≡CH | *2 |
| 742 | —CH$_2$— | " | 6-CH$_3$ | 2-F, 4-Cl, 5-SO$_2$N(CH$_3$)$_2$ | 111–113 |
| 743 | " | " | " | 2-F, 4-Cl, 5-SCH(CH$_3$)COOCH$_3$ | $n_D^{28}$ 1.6000 |

*1 $^1$H—NMR (90 MHz) (in CDCl$_3$) δ 1.3 (3H, d), 2.1–2.6 (1H, m), 2.7–3.2 (2H, m), 3.2–3.6 (1H, m), 3.9–4.2 (1H, m), 3.65 (2H, s ), 6.8 (1H, d), 7.1 (1H, d)
*2 $^2$H—NMR (270 MHz) (in CDCl$_3$) δ 2.60 (1H, t), 3.72 (2H, s), 4.58 (2H, s), 4.75 (2H, d), 5.20 (2H, d), 6.86 (1H, d), 7.22 (1H, d)

As mentioned previously, the compounds possess superior herbicidal activity. The compounds may be applied directly to the soil as pre-emergence treatment or to plant foliage as post-emergence treatment, or they can be mixed intimately with soil. The compounds may be applied to soil or to plant foliage in amount of 1 g or more per 10 are.

A herbicidal composition having a compound of this invention as its active ingredient may be formulated by mixing suitable carriers in a form generally used in agricultural chemicals such as wettable powder, water soluble powder, glanule, emulsifiable concentrate and flowable. As solid carriers, talc, white carbon, bentonite, clay, diatomaceous earth or the like may be used. As liquid carriers, water, alcohol, benzene, xylene, kerosene, mineral oil, cyclohexane, cyclohexanone, dimethylformamide or the like may be used. A surface active agent may, if necessary, be added in order to give a homogeneous and stable formulation.

Compounds can also be applied admixed with other chemicals, which are used in agronomic and horticultural management and which are compatible with such compounds. Such chemicals can be, but are not restricted to, the classes of chemical commonly known as fungicides, insecticides, acaricides, herbicides and plant growth regulators. In particular, by mixing it with the other herbicides, its applied dosage and manpower can be decreased and furthermore, the higher effect by synergetic function of both chemicals can be expected.

For admixture of the compound with known herbicides, the use is recommended of benthiocarb, molinate, MY-93 (S-2,2-dimethylbenzil) 1-piperidinecarbothioate) or other carbamate-type herbicides; thiocarbamate-type herbicides; butachlor, pretilachlor or other acid amide-type herbicides; chlormethoxynil, bifenox or other diphenylether-type herbicides; pyrazolate, pyrazoxyfen or other pyrazole-type herbicides; chlorsulfuron, sulfometuron or other sulfonylurea-type herbicides; MCP, MCPB or other phenoxy alkane carboxylic acid-type herbicides; diclofop-methyl or other phenoxy propionic acid-type herbicides; fluazifopbutyl or other pyridyloxyphenoxypropionic acid-type herbicides; piperophos, dymron, bentazon, oxadiazon, NTN-801 (2-benzothiazole-2-yloxy-N-methyl acetoanilide), naproanilid, HW-52 (4-ethoxymethoxybenzo-2',3'-dichloroanilide), KNW-242 (1-(3-methylphenyl)-5-phenyl-1H-1,2,4-triazole-3-carboxamide), S47 (N-(α,α-dimethylbenzil)-d-bromotertiary butyl acetoamide, sethoxydim, alloxydim-sodium and other cyclohexanedione-type herbicides. These herbicides in various combinations may also be mixed with a vegetable oil or an oil concentrate.

The concentration of the active ingredient in a herbicidal composition may vary according to type of formulation, and the concentration is, for example, in the range of 5–80 weight percent, preferably 30–60 weight percent, in wettable powder; 70–95 weight percent, preferably 80–90 weight percent, in water soluble powder; 5–70 weight percent, preferably 10–40 weight percent, in emulsifiable concentrate; 10–70 weight percent, preferably 20–50 weight percent, in flowable; 0.5–10 weight percent, preferably 1–5 weight percent, in glanule.

A wettable powder, a water soluble powder or an emulsifiable concentrate thus produced may be diluted with water to a specified concentration and used as a liquid suspension or a liquid emulsion for treating soils or plant foliage. Further, a flowable and a glanule may be directly used for soil or foliage treatment, otherwise, it may be diluted with water to a specified concentration and used as a liquid suspension for treating soils or plant foliage.

Non-limiting examples of herbicidal composition are illustrated by the following tests:

| Example 21 Wettable powder | |
|---|---|
| | parts by weight |
| Compound No. 683 | 50 |

| Example 21 Wettable powder | |
|---|---|
| | parts by weight |
| White carbon | 12 |
| Diatomaceoua earth | 30 |
| Sodium alkylsulfate | 8 |

These are mixed homogeneously and reduced to fine particles to provide a wettable powder containing 50% of active ingredient. In use, it is diluted to a desired concentration with water, and is sprayed as suspension.

| Example 22 Emulsifiable concentrace | |
|---|---|
| | parts by weight |
| Compound No. 430 | 40 |
| Xylene | 35 |
| Dimethylformamide | 15 |
| Polyoxyethylene phenyl ether | 10 |

These are mixed and dissolved to provide an emulsifiable concentrate containing 40% of active ingredient. In use, it is diluted to a desired concentration with water, and sprayed as an emulsion.

| Example 23 Flowable | |
|---|---|
| | parts by weight |
| Compound No. 609 | 30 |
| Sun spray-7N (commercial product of Sun Oil Co., Ltd.) | 60 |
| Polyoxyethylene alkylether | 5 |
| Sorbitan alkylate | 5 |

These are mixed homogeneously to provide a flowable containing 30% of active ingredient.

| Example 24 Glanule | |
|---|---|
| | parts by weight |
| Compound No. 197 | 3 |
| Talc | 40 |
| Clay | 40 |
| Bentonite | 10 |
| Sodium alkyl sulfate | 7 |

These are mixed homogeneously to provide a glanule containing 3% of active ingredient.

The herbicidal effects of compounds are illustrated by the following tests:

Test 1

Paddy field test

Seeds of barnyardgrass (*Echinochloa crus-galli*), ducktongue weed (*Monochoria vaginalis*), bulrush (Scirpus Hotarui) and small-flower umbrella plant (*Cyperus difformis*) were planted 0.2–0.5 cm in depth in plastic pots (15 cm depth and 14 cm diameter) containing paddy field soil, and two rice plants (variety: Nihonbare) at 2–3 leaf stage were transplanted. Next day pots were watered 2–3 cm in depth. Immediately granules of each compounds of this invention were applied at the dosage described in the table. The pots were kept in a greenhouse.

Three weeks after treatment, the degree of damage of the each plants was observed and evaluated on the scale of value of 0–10, which has the following meanings.

| Index | Degree of damage |
|---|---|
| 0 | 0% |
| 2 | 20-29% |
| 4 | 40-49% |
| 6 | 60-69% |
| 8 | 80-89% |
| 10 | 100 |

Index 1, 3, 5, 7 and 9 mean the intermediate degree between 0 and 2, 2 and 4, 4 and 6, 6 and 8, 8 and 10 respectively.

Degree of damage (%) =

$$\frac{\left(\begin{array}{c}\text{Fresh weight}\\ \text{in untreated plot}\end{array}\right) - \left(\begin{array}{c}\text{Fresh weight}\\ \text{in treated plot}\end{array}\right)}{\text{Fresh weight in untreated plot}} \times 100$$

The results are shown in Table 2.

TABLE 2

| | Application Rate of Active Ingredient (g/10 a) | Degree of Damage | | | | |
|---|---|---|---|---|---|---|
| | | Rice plant | B.G.*1 | D.T.W.*2 | B.R.*3 | S.U.P.*4 |
| Compound No. | | | | | | |
| 10 | 50 | 1 | 4 | 10 | 10 | 10 |
| 13 | 50 | 1 | 10 | 10 | 10 | 10 |
| 15 | 50 | 1 | 0 | 10 | 10 | 10 |
| 28 | 50 | 0 | 5 | 10 | 10 | 10 |
| 54 | 50 | 0 | 3 | 10 | 9 | 8 |
| 73 | 50 | 0 | 0 | 10 | 10 | 9 |
| 106 | 50 | 0 | 10 | 10 | 10 | 10 |
| 115 | 50 | 0 | 9 | 10 | 10 | 10 |
| 117 | 50 | 0 | 9 | 10 | 10 | 10 |
| 119 | 25 | 0 | 10 | 10 | 10 | 10 |
| 123 | 50 | 0 | 10 | 10 | 10 | 10 |
| 127 | 25 | 0 | 10 | 10 | 10 | 10 |
| 133 | 50 | 0 | 10 | 10 | 10 | 10 |
| 134 | 50 | 0 | 9 | 10 | 10 | 10 |
| 138 | 50 | 1 | 8 | 10 | 8 | 10 |
| 142 | 50 | 0 | 3 | 10 | 10 | 10 |
| 151 | 50 | 3 | 9 | 10 | 9 | 10 |
| 182 | 50 | 0 | 4 | 10 | 10 | 10 |
| 188 | 50 | 0 | 6 | 10 | 9 | 10 |
| 194 | 25 | 1 | 10 | 10 | 10 | 10 |
| 196 | 50 | 0 | 10 | 10 | 10 | 10 |
| 197 | 50 | 0 | 10 | 10 | 10 | 10 |
| 199 | 50 | 0 | 9 | 10 | 10 | 10 |
| 202 | 50 | 0 | 4 | 10 | 10 | 10 |
| 205 | 50 | 0 | 10 | 10 | 10 | 10 |
| 207 | 25 | 0 | 9 | 10 | 10 | 10 |
| 209 | 50 | 1 | 9 | 10 | 10 | 10 |
| 212 | 25 | 0 | 0 | 10 | 10 | 10 |
| 213 | 50 | 1 | 10 | 10 | 10 | 10 |
| 214 | 50 | 1 | 10 | 10 | 10 | 10 |
| 216 | 50 | 1 | 9 | 10 | 10 | 10 |
| 219 | 50 | 0 | 10 | 10 | 9 | 10 |
| 220 | 50 | 0 | 3 | 10 | 10 | 10 |
| 223 | 50 | 0 | 8 | 10 | 7 | 9 |
| 224 | 50 | 0 | 10 | 10 | 10 | 10 |
| 227 | 25 | 0 | 4 | 10 | 10 | 10 |
| 231 | 50 | 1 | 9 | 10 | 10 | 10 |
| 234 | 50 | 0 | 0 | 10 | 10 | 10 |
| 239 | 25 | 0 | 7 | 10 | 10 | 9 |
| 241 | 50 | 0 | 10 | 10 | 10 | 10 |
| 251 | 50 | 0 | 3 | 10 | 10 | 9 |
| 256 | 50 | 0 | 9 | 10 | 10 | 10 |
| 258 | 25 | 0 | 3 | 10 | 10 | 8 |
| 263 | 50 | 0 | 10 | 10 | 7 | 10 |
| 270 | 50 | 1 | 8 | 10 | 10 | 10 |
| 292 | 50 | 0 | 2 | 10 | 5 | 8 |
| 304 | 50 | 2 | 3 | 10 | 9 | 7 |
| 309 | 50 | 0 | 1 | 10 | 10 | 10 |
| 316 | 50 | 1 | 10 | 10 | 10 | 10 |
| 318 | 50 | 0 | 10 | 10 | 10 | 10 |
| 328 | 50 | 0 | 10 | 10 | 10 | 10 |
| 331 | 50 | 0 | 0 | 10 | 10 | 10 |
| 335 | 50 | 0 | 10 | 10 | 10 | 10 |
| 341 | 50 | 0 | 3 | 10 | 10 | 10 |
| 345 | 25 | 0 | 2 | 10 | 10 | 10 |
| 350 | 50 | 0 | 10 | 10 | 10 | 10 |
| 361 | 50 | 0 | 6 | 10 | 10 | 10 |
| 368 | 25 | 0 | 0 | 10 | 10 | 10 |
| 378 | 50 | 1 | 7 | 10 | 10 | 10 |
| 381 | 50 | 0 | 0 | 10 | 9 | 10 |
| 386 | 50 | 2 | 9 | 10 | 3 | 10 |
| 396 | 50 | 1 | 8 | 10 | 10 | 10 |
| 398 | 50 | 1 | 4 | 10 | 10 | 10 |
| 409 | 50 | 0 | 2 | 10 | 9 | 9 |
| 415 | 50 | 0 | 7 | 10 | 10 | 10 |
| 418 | 50 | 0 | 2 | 10 | 10 | 10 |
| 421 | 50 | 2 | 7 | 10 | 10 | 10 |
| 430 | 25 | 1 | 10 | 10 | 10 | 10 |
| 438 | 25 | 1 | 10 | 10 | 10 | 10 |
| 439 | 25 | 0 | 5 | 10 | 10 | 10 |
| 444 | 25 | 0 | 10 | 10 | 10 | 10 |
| 458 | 50 | 0 | 10 | 10 | 7 | 10 |
| 461 | 50 | 0 | 10 | 10 | 10 | 10 |
| 465 | 50 | 1 | 10 | 10 | 10 | 10 |
| 483 | 50 | 2 | 10 | 10 | 10 | 10 |
| 487 | 25 | 0 | 0 | 9 | 3 | 9 |
| 494 | 50 | 0 | 10 | 10 | 8 | 10 |
| 505 | 50 | 0 | 10 | 10 | 5 | 10 |
| 511 | 50 | 0 | 3 | 10 | 10 | 10 |
| 514 | 50 | 0 | 2 | 10 | 10 | 10 |
| 527 | 50 | 0 | 4 | 10 | 8 | 9 |
| 565 | 50 | 2 | 10 | 10 | 10 | 10 |
| 574 | 50 | 1 | 10 | 10 | 10 | 10 |
| 580 | 50 | 0 | 10 | 10 | 10 | 10 |
| 584 | 50 | 0 | 10 | 10 | 4 | 10 |
| 589 | 50 | 1 | 3 | 10 | 10 | 10 |
| 616 | 50 | 1 | 10 | 10 | 10 | 10 |
| 618 | 50 | 0 | 10 | 10 | 10 | 10 |
| 623 | 50 | 1 | 10 | 10 | 10 | 10 |
| 629 | 50 | 0 | 3 | 10 | 10 | 10 |
| 636 | 50 | 1 | 10 | 10 | 8 | 10 |
| 663 | 50 | 0 | 4 | 10 | 7 | 10 |
| 668 | 50 | 0 | 8 | 10 | 5 | 10 |
| 674 | 50 | 0 | 5 | 10 | 10 | 10 |
| 693 | 50 | 0 | 10 | 10 | 8 | 10 |
| 697 | 50 | 0 | 10 | 10 | 3 | 10 |
| 711 | 50 | 0 | 10 | 10 | 6 | 10 |
| 716 | 50 | 0 | 7 | 10 | 9 | 10 |
| 730 | 50 | 0 | 4 | 10 | 3 | 10 |
| Comparative Compound | | | | | | |
| *(1) | 100 | 0 | 4 | 8 | 4 | 1 |

TABLE 2-continued

| | Application Rate of Active Ingredient (g/10 a) | Rice plant | Degree of Damage | | | |
|---|---|---|---|---|---|---|
| | | | B.G.*1 | D.T.W.*2 | B.R.*3 | S.U.P.*4 |
| (2) | 100 | 0 | 1 | 2 | 1 | 2 |

*1: B.G.—barnyardgrass
*2: D.T.W.—duck-tongue weed
*3: B.R.—bulrush
*4: S.U.P.—small-flower umbrella plant
*(1)

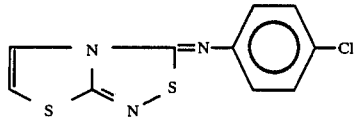

(2)

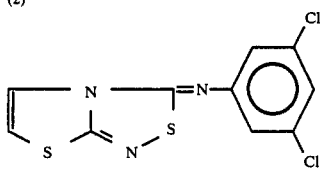

Test 2

Postemergence treatment test

Seeds of lambsquarter (*Chenopodium album*), pigweed (*Amaranthus retroflexus*), sedge (*Cyperus microiria*) and soybean were planted in clay pots (12 cm depth and 16 cm diameter) containing clay loam soil and were allowed to grow in greenhouse. When the plants were grown to a 3–10 cm height, aqueous suspensions, prepared by diluting an emulsifiable concentrate with water to specified concentration (500 ppm) were sprayed on the foliage of the plants at a rate of 100 1/10 a by using a micro-sprayer. Three weeks after treatment the degree of damage of the each plants was observed and evaluated on the same scale as in Test 1. The results are shown in Table 3.

TABLE 3

| Compound No. | Application Rate of Active Ingredient (g/10 a) | Degree of Damage | | |
|---|---|---|---|---|
| | | Soybean | L.Q.*5 | P.W.*6 | S.D.*7 |
| 11 | 50 | 5 | 10 | 10 | 10 |
| 14 | 25 | 3 | 10 | 10 | 10 |
| 124 | 25 | 2 | 10 | 9 | 10 |
| 125 | 50 | 3 | 10 | 10 | 10 |
| 139 | 50 | 1 | 10 | 10 | 10 |
| 140 | 25 | 1 | 10 | 7 | 10 |
| 150 | 25 | 2 | 9 | 10 | 10 |
| 152 | 25 | 4 | 10 | 8 | 8 |
| 153 | 25 | 1 | 7 | 8 | 7 |
| 157 | 50 | 2 | 10 | 9 | 7 |
| 161 | 25 | 2 | 9 | 9 | 8 |
| 171 | 25 | 1 | 10 | 10 | 9 |
| 173 | 50 | 5 | 10 | 10 | 10 |
| 175 | 50 | 3 | 10 | 9 | 10 |
| 176 | 50 | 2 | 10 | 10 | 10 |
| 183 | 25 | 1 | 8 | 9 | 8 |
| 190 | 25 | 2 | 9 | 7 | 7 |
| 243 | 50 | 5 | 9 | 10 | 10 |
| 245 | 25 | 1 | 5 | 9 | 8 |
| 266 | 25 | 3 | 10 | 10 | 10 |
| 269 | 25 | 6 | 10 | 10 | 10 |
| 272 | 25 | 4 | 10 | 10 | 10 |
| 274 | 50 | 4 | 10 | 10 | 10 |
| 277 | 25 | 1 | 7 | 10 | 9 |
| 279 | 25 | 2 | 10 | 10 | 10 |
| 281 | 25 | 3 | 10 | 9 | 10 |
| 282 | 50 | 5 | 10 | 10 | 10 |
| 320 | 50 | 2 | 9 | 10 | 10 |
| 325 | 25 | 3 | 10 | 10 | 10 |
| 330 | 25 | 3 | 10 | 10 | 10 |
| 353 | 25 | 4 | 10 | 10 | 10 |
| 356 | 25 | 5 | 8 | 10 | 9 |
| 358 | 25 | 1 | 8 | 10 | 8 |
| 360 | 50 | 2 | 10 | 10 | 10 |
| 365 | 50 | 3 | 10 | 10 | 10 |
| 366 | 25 | 3 | 10 | 10 | 10 |
| 369 | 25 | 4 | 10 | 10 | 10 |
| 374 | 25 | 3 | 10 | 10 | 10 |
| 376 | 25 | 4 | 10 | 9 | 9 |
| 379 | 50 | 5 | 10 | 10 | 10 |
| 387 | 25 | 4 | 10 | 10 | 10 |
| 390 | 25 | 2 | 9 | 9 | 9 |
| 391 | 25 | 2 | 9 | 10 | 9 |
| 393 | 50 | 4 | 10 | 10 | 10 |
| 394 | 25 | 1 | 9 | 8 | 8 |
| 399 | 25 | 6 | 10 | 7 | 8 |
| 404 | 25 | 5 | 10 | 10 | 10 |
| 410 | 50 | 4 | 10 | 7 | 9 |
| 411 | 25 | 2 | 9 | 9 | 8 |
| 419 | 25 | 5 | 10 | 10 | 7 |
| 420 | 25 | 7 | 10 | 10 | 10 |
| 449 | 50 | 6 | 10 | 10 | 10 |
| 456 | 25 | 9 | 9 | 10 | 9 |
| 477 | 25 | 3 | 8 | 8 | 5 |
| 480 | 50 | 6 | 10 | 10 | 10 |
| 492 | 25 | 4 | 10 | 10 | 10 |
| 510 | 25 | 3 | 10 | 10 | 10 |
| 522 | 50 | 3 | 10 | 10 | 10 |
| 532 | 50 | 4 | 10 | 10 | 10 |
| 533 | 50 | 2 | 10 | 10 | 10 |
| 535 | 50 | 7 | 10 | 10 | 10 |
| 536 | 25 | 2 | 10 | 10 | 10 |
| 537 | 50 | 4 | 10 | 10 | 10 |
| 544 | 50 | 4 | 10 | 10 | 10 |
| 545 | 50 | 4 | 10 | 10 | 10 |
| 546 | 50 | 2 | 10 | 10 | 10 |
| 550 | 50 | 7 | 10 | 10 | 10 |
| 555 | 50 | 3 | 10 | 10 | 10 |
| 561 | 50 | 4 | 10 | 10 | 10 |
| 562 | 50 | 2 | 10 | 10 | 10 |
| 568 | 50 | 4 | 10 | 10 | 10 |
| 569 | 50 | 3 | 10 | 10 | 10 |
| 571 | 50 | 4 | 10 | 10 | 10 |
| 572 | 50 | 2 | 10 | 10 | 10 |
| 591 | 50 | 1 | 10 | 10 | 10 |
| 592 | 50 | 2 | 7 | 6 | 5 |
| 593 | 25 | 2 | 9 | 9 | 8 |
| 595 | 25 | 5 | 10 | 10 | 10 |
| 597 | 25 | 3 | 10 | 10 | 10 |
| 598 | 25 | 4 | 10 | 10 | 10 |
| 604 | 25 | 4 | 10 | 10 | 10 |
| 605 | 25 | 4 | 10 | 10 | 10 |
| 606 | 25 | 2 | 10 | 10 | 10 |
| 607 | 50 | 6 | 10 | 10 | 10 |
| 608 | 25 | 5 | 10 | 9 | 9 |
| 609 | 25 | 1 | 10 | 10 | 10 |
| 610 | 25 | 5 | 10 | 9 | 9 |
| 611 | 25 | 5 | 10 | 10 | 10 |
| 612 | 50 | 3 | 10 | 10 | 10 |
| 613 | 50 | 2 | 10 | 10 | 10 |
| 626 | 50 | 6 | 10 | 10 | 10 |
| 632 | 25 | 7 | 10 | 10 | 10 |
| 635 | 50 | 8 | 10 | 10 | 10 |
| 638 | 25 | 4 | 10 | 10 | 10 |
| 641 | 50 | 7 | 10 | 10 | 10 |
| 646 | 50 | 7 | 10 | 10 | 10 |
| 650 | 50 | 2 | 10 | 10 | 10 |
| 653 | 50 | 1 | 10 | 10 | 10 |
| 659 | 50 | 1 | 10 | 10 | 10 |
| 660 | 50 | 5 | 10 | 10 | 10 |
| 665 | 25 | 6 | 9 | 8 | 9 |
| 683 | 25 | 2 | 10 | 10 | 10 |
| 686 | 50 | 10 | 10 | 10 | 10 |
| 689 | 50 | 8 | 10 | 10 | 10 |
| 690 | 50 | 8 | 10 | 10 | 10 |
| 691 | 50 | 10 | 10 | 10 | 10 |
| 694 | 50 | 3 | 10 | 10 | 10 |
| 707 | 25 | 1 | 10 | 10 | 10 |
| 718 | 50 | 6 | 10 | 10 | 10 |

TABLE 3-continued

| | | | | | |
|---|---|---|---|---|---|
| 719 | 25 | 2 | 10 | 10 | 10 |
| 720 | 25 | 2 | 10 | 10 | 10 |
| 721 | 50 | 3 | 10 | 10 | 10 |
| 725 | 50 | 1 | 6 | 9 | 7 |
| 728 | 50 | 6 | 10 | 10 | 10 |
| 730 | 50 | 9 | 10 | 10 | 10 |
| 733 | 50 | 8 | 10 | 10 | 10 |
| Comparative Compound | | | | | |
| *(1) | 400 | 4 | 3 | 3 | 4 |
| (2) | 400 | 3 | 0 | 1 | 2 |

*[5]L.Q. . . . lambsquater
*[6]P.W. . . . pigweed
*[7]S.D. . . . sedge

*(1) ⎫
*(2) ⎭ The same compound as shown in Table 2

What we claim is:

1. A compound having the formula

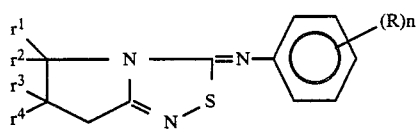

wherein
each of $r^1$, $r^2$, $r^3$ and $R^4$ represents hydrogen, $C_{1-4}$ alkyl which may be substituted by $C_{1-3}$ alkoxy, phenyl or methylthio, or phenyl which may be substituted by halogen or methyl, and such $r^1$, $r^2$, $r^3$ and $r^4$ may form alkylidene, and at least two of $r^1$, $r^2$, $r^3$ and $r^4$ are hydrogen; and
R represents same or different substituent(s) selected from the group consisting of halogen, nitro, cyano, $-G-R^1$,

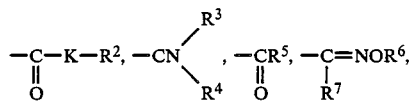

dimethyl sulfamoyl and —L; and
n represents an integer of 1 to 5; and
wherein
G represents —O—, —S—,

in which $r^{10}$ represents hydrogen or $C_{2-3}$ alkynyl; and $R^1$ represents hydrogen,

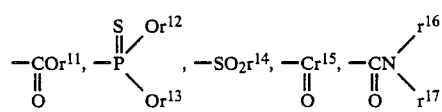

quinoxalinyl which may be substituted by halogen, thiadiazolyl which may be substituted by methyl, pyridyl, 1,3,5-triazinyl,
which may be substituted by halogen or methylamino, thiazolyl, tetrahydropyranyl, or
—T; and
K represents oxygen or sulfur; and $R^2$ represents hydrogen, metal corresponding to one valency, $C_{1-3}$ alkylidene amino or —U; and
each of $R^3$ and $R^4$ represents hydrogen, $C_{1-3}$ alkyl, $C_{2-3}$ alkynyl or $C_{1-2}$ alkoxy; and
$R^5$ represents phenyl or $C_{1-3}$ alkyl which may be substituted by methoxy; and
$R^6$ represents hydrogen, or $C_{1-2}$ alkyl, which may be substituted by $C_{1-2}$ alkoxycarbonyl; and
$R^7$ represents hydrogen or methyl; and
—L represents phenyl which may be substituted by methyl, $C_{2-3}$ alkenyl which may be substituted by

$C_{2-5}$ alkynyl, or $C_{1-3}$ alkyl which may be substituted by halogen, hydroxy, cyano,

methoxy, acetyloxy or

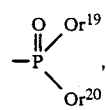

and
wherein
$r^{11}$ represents methyl; and
each of $r^{12}$ and $r^{13}$ represents $C_{1-2}$ alkyl; and
$r^{14}$ represents $C_{1-3}$ alkyl or phenyl which may be substituted by methyl; and
$r^{15}$ represents $C_{1-3}$ alkyl which may be substituted by halogen or
$C_{1-2}$ alkoxycarbonyl or phenyl which may be substituted by halogen; and each of $r^{16}$ and $r^{17}$ represents hydrogen or $C_{1-2}$ alkyl; and —T represents $C_{1-12}$ alkyl which may be substituted by halogen, $C_{3-6}$ cycloalkyl (which may be substituted by halogen), cyano, phenyl (which may be substituted by halogen, nitro, cyano, methyl or methoxy), $-Q-r^{21}$, acethyloxy, trimethylsilyl, $$-CWr^{22},\ -CN\genfrac{}{}{0pt}{}{r^{23}}{Z\ r^{24}},\ -C-r^{25},\ -C=NOr^{26},$$
     ‖           ‖          ‖         |
     O           Z          O         $r^{27}$ $-(OC_2H_4-)_2OCH_3$, $-(OC_2H_4-)_3OCH_3$ isoxazolyl (which may be substituted by methyl), oxadiazolyl (which may be substituted by $C_{1-3}$ alkyl), pyrazolyl, or pyrydyl, $C_{3-6}$ cycloalkyl which may be substituted by propargyl or halogen, $C_{3-4}$ alkenyl which may be substituted by halogen or ethoxycarbonyl, $C_{3-8}$ alkynyl which may be substituted by halogen or phenyl, or phenyl which may be substituted by halogen, trifluoromethyl or ethoxycarbonylethoxy; and
—U represents $C_{1-8}$ alkyl which may be substituted by cyclopropyl, halocyclopropyl, cyano, $C_{1-4}$ alkoxycarbonyl, methoxy, phenoxy, phenylthio, trimethylsilyl or $-O(CH_2)_{gh}-Or^{28}$, $C_{2-4}$ alkenyl which may be substituted by $C_{1-3}$ alkoxycarbonyl or propargyl which may be substituted by phenyl; and $r^{18}$ represents hydrogen, metal corresponding to one valency, $C_{1-7}$ alkyl or propargyl; and wherein Q represents —O— or —S(O)$_k$—(k=0, 1 or 2); and $r^{21}$ represents hydrogen, $C_{1-2}$ alkyl, which may be substituted by phenyl, methoxy or phenoxy, $C_{1-2}$ alkoxycarbonyl, vinyl, phenyl which may be substituted by halogen, nitro, methoxy, methyl, trifluoromethyl or methylendioxy, naphthyl, pyrydyl which may be substituted by methyl or methylcarbamoyl; and W represents oxygen or sulfur; and $r^{22}$ represents hydrogen, metal corresponding to one valency, $C_{1-3}$ alkylidene amino, allyl, $C_{3-5}$ alkynyl, phenyl or $C_{1-10}$ alkyl which may be substituted by halogen, $C_{1-3}$ alkoxy $C_{2-3}$ alkenyloxy, benzyloxy, phenyl which may be substituted by methoxy, methylthio, phenoxy, allylthio, benzylthio or phenylthio, $C_{1-2}$ alkoxycarbonyl, methoxycarbonylmethylthio, furyl, isoxazolyl which may be substituted by methyl, trimethylsilyl or cyano; and Z represents oxygen or sulfur; and each of $r^{23}$ and $r^{24}$ represents hydrogen, ethoxy, allyloxy, cyclohexylcarbamoyl, $C_{1-4}$ alkyl radical which may be substituted by $C_{1-2}$ alkoxy phenyl or $C_{1-2}$ alkoxycarbonyl, allyl, propargyl, cyclohexyl or phenyl; and $r^{25}$ represents methyl, phenyl or morpholino; and $r^{26}$ represents hydrogen, allyl or acetyl which may be substituted by halogen; and $r^{27}$ represents amino, methyl or phenyl; and g represents an integer of 1 to 3; and h represents an integer of 2 to 7; and $r^{28}$ represents methyl;

or a salt thereof with an organic or inorganic acid.

2. A herbicidal composition comprising an inert carrier and an effective amount of a compound of claim 1.

3. A process for the control of the weeds comprising applying to the locus to be protected an effective amount of a compound of claim 1.

* * * * *